United States Patent
Mycek et al.

(10) Patent No.: US 8,234,078 B2
(45) Date of Patent: *Jul. 31, 2012

(54) MULTIMODAL SPECTROSCOPIC SYSTEMS AND METHODS FOR CLASSIFYING BIOLOGICAL TISSUE

(75) Inventors: Mary-Ann Mycek, Ann Arbor, MI (US); Malavika Chandra, Lansdale, PA (US); James Scheiman, Sup Township, MI (US); Robert H. Wilson, Ann Arbor, MI (US); Diane Simeone, Ann Arbor, MI (US); Barbara McKenna, Ann Arbor, MI (US); Julianne Purdy, Ann Arbor, MI (US); Jeremy Taylor, Ann Arbor, MI (US); Oliver Lee, Ann Arbor, MI (US)

(73) Assignee: The Regents of the University of Michigan, Ann Arbor, MI (US)

(*) Notice: Subject to any disclaimer, the term of this patent is extended or adjusted under 35 U.S.C. 154(b) by 0 days.

This patent is subject to a terminal disclaimer.

(21) Appl. No.: 12/882,131

(22) Filed: Sep. 14, 2010

(65) Prior Publication Data

US 2010/0330611 A1 Dec. 30, 2010

Related U.S. Application Data

(63) Continuation-in-part of application No. 12/479,600, filed on Jun. 5, 2009.

(60) Provisional application No. 61/242,126, filed on Sep. 14, 2009, provisional application No. 61/058,966, filed on Jun. 5, 2008.

(51) Int. Cl.
*G01N 33/48* (2006.01)
*G06F 7/60* (2006.01)
*G06G 7/58* (2006.01)

(52) U.S. Cl. ............... 702/19; 702/20; 703/2; 703/11

(58) Field of Classification Search ............... None
See application file for complete search history.

(56) References Cited

U.S. PATENT DOCUMENTS 5,601,087 A 2/1997 Gunderson et al.
6,174,291 B1 1/2001 McMahon et al.

OTHER PUBLICATIONS

Volynskaya et al., "Diagnosing breast cancer using diffuse reflectance spectroscopy and intrinsic fluorescence spectroscopy", Journal of Biomedical Optics, Mar./Apr. 2008, pp. 024012-1 to 9, vol. 13(2).
Chandra et al., "Pancreatic tissue assessment using fluorescence and reflectance spectroscopy", Proc. of SPIE-OSA Biomedical Optics, 2007, pp. 66281R-1 to 8, SPIE vol. 6628.
Wilson et al., "Photon-tissue interaction model enables quantitative optical analysis of human pancreatic tissues", Optical Society of America, 2010.
Koninger et al., "Overexpressed Decorin in Pancreatic Cancer: Potential Tumor Growth Inhibition and Attenuation of Chemotherapeutic Action", Clin, Cancer Res., Jul. 15, 2004, pp. 4776-4783, vol. 10.
Hruban et al., "An Illustrated Consensus on the Classification of Pancreatic Intraepithelial Neoplasia and Intraductal Papillary Mucinous Neoplasms," Am. J. Surg. Pathol., Aug. 2004, pp. 977-987, vol. 28, No. 8.
Wilson et al., "Optical spectroscopy detects histological hallmarks of pancreatic cancer", Manuscript submitted to Optics Express, Apr. 27, 2009.
Saidi et al., "Mie and Rayleigh modeling of visible-light scattering in neonatal skin", Applied Optics, Nov. 1, 1995, pp. 7410-7418, Vo. 34, No. 31.
Van Veen et al., "Diffuse-reflectance spectroscopy from 500 to 1060 nm by correction for inhomogeneously distributed absorbers", Optics Letters, Feb. 15, 2002, pp. 246-248, vol. 27, No. 4.
Chandra et al., "Probing pancreatic disease using tissue optical spectroscopy", Journal of Biomedical Optics, Nov./Dec. 2007, pp. 060501-1 to 3, vol. 12(6).
Vishwanath et al., "Do fluorescence decays remitted from tissues accurately reflect intrinsic fluorophore lifetimes?", Optics Letters, Jul. 1, 2004, pp. 1512-1514, vol. 29, No. 13.
Zonios et al., "Comparative evaluation of two simple diffuse reflectance models for biological tissue applications", Applied Optics, Sep. 20, 2008, pp. 4965-4973, vol. 47, No. 27.
Reif et al., "Analysis of changes in reflectance measurements on biological tissues subjected to different probe pressures", Journal of Biomedical Optics, Jan./Feb. 2008, pp. 010502-1 to 3, vol. 13(1).
Wang et al., "MCML—Monte Carlo modeling of light transport in multi-layered tissues", Computer Methods and Programs in Biomedicine 47, 1995, pp. 131-146.
Cohen et al., "Pancreatic Adenocarcinoma: Regression Analysis to Identify Improved Cytologic Criteria", Diagnostic Cytopathology, 1991, pp. 341-345, vol. 7, No. 4.
Chandra et al., "Quantitative molecular sensing in biological tissues: an approach to non-invasive optical characterization", Optics Express, Jun. 26, 2006, pp. 6157-6171, vol. 14, No. 13.
Hillemanns et al., Lymph node metastasis detection of ovarian cancer by porphyrin fluorescence photodetection: case report, Lasers Med. Sci., 2007, pp. 131-135, vol. 22.
Finlay et al., "Hemoglobin oxygen saturations in phantoms and in vivo from measurements of steady-state diffuse reflectance at a single, short source-detector separation", Medical Physics, Jul. 2004, pp. 1949-1959, vol. 31, No. 7.
Perelman et al., "Observation of Periodic Fine Structure in Reflectance from Biological Tissue: A New Technique for Measuring Nuclear Size Distribution", Physical Review Letters, Jan. 19, 1998, pp. 627-630, vol. 80, No. 3.
Sears et al., "Image Cytometry as a Discriminatory Tool for Cytologic Specimens Obtained by Endoscopic Retrograde Cholangiopancreatography", Cancer Cytopathology, Apr. 25, 1998, pp. 119-126, vol. 84, No. 2.

(Continued)

*Primary Examiner* — Shubo Zhou
(74) *Attorney, Agent, or Firm* — Howard & Howard Attorneys PLLC

(57) ABSTRACT

Multimodal optical spectroscopy systems and methods produce a spectroscopic event to obtain spectroscopic response data from biological tissue and compare the response data with an empirical equation configured to correlate the measured response data and the most probable attributes of the tissue, thus facilitating classification of the tissue based on those attributes for subsequent biopsy or remedial measures as necessary.

18 Claims, 18 Drawing Sheets

OTHER PUBLICATIONS

Palmer et al., "Monte-Carlo-based model for the extraction of intrinsic fluorescence from turbid media", Journal of Biomedical Optics, Mar./Apr. 2008, pp. 024017-1 to 9, vol. 13(2).

Imamura et al., "Quantitative Analysis of Collagen and Collagen Subtypes I, III, and V in Human Pancreatic Cancer, Tumor-Associated Chronic Pancreatitis, and Alcoholic Chronic Pancreatitis", Pancreas, 1995, pp. 357-364, vol. 11, No. 4.

Chandra et al., "Spectral areas and ratios classifier algorithm for pancreatic tissue classification using optical spectroscopy", Journal of Biomedical Optics, Jan./Feb. 2010, pp. 010514-1 to 3, vol. 15(1).

Fox et al., "Formaldehyde Fixation", The Journal of Histochemistry & Cytochemistry, 1985, pp. 845-853, vol. 33, No. 8.

Vishwanath et al., "Time-resolved photon migration in bi-layered tissue models", Optics Express, Sep. 19, 2005, pp. 7466-7482, vol. 13, No. 19.

Joshi et al., "Improving PET receptor binding estimates from Logan plots using principal component analysis", Journal of Cerebral Blood Flow & Metabolism, 2008, pp. 852-865, vol. 28.

Sefkow et al., "Method for Measuring Cellular Optical Absorption and Scattering Evaluated Using Dilute Cell Suspension Phantoms", Applied Spectroscopy, 2001, vol. 55, No. 11.

Zonios et al., "Diffuse reflectance spectroscopy of human adenomatous colon polyps in vivo", Applied Optics, Nov. 1, 1999, pp. 6628-6637, vol. 38, No. 31.

Ge et al., "Identification of Colonic Dysplasi and Neoplasia by Diffuse Reflectance Spectroscopy and Pattern Recognition Techniques", Applied Spectroscopy, 1998, pp. 833-839, vol. 52, No. 6.

Lin et al., "Cytologic Criteria for Well Differentiated Adenocarcinoma of the Pancreas in Fine-Needle Aspiration Biopsy Specimens", Cancer Cytopathology, Feb. 25, 2003, pp. 44-50, vol. 99, No. 1.

Muller et al., "Intrinsic fluorescence spectroscopy in turbid media: disentangling effects of scattering and absorption", Applied Optics, Sep. 1, 2001, pp. 4633-4646, vol. 40, No. 25.

Reif et al., "Analytical model of light reflectance for extraction of the optical properties in small volumes of turbid media", Applied Optics, Oct. 10, 2007, pp. 7317-7328, vol. 46, No. 29.

Hruban et al., "Pancreatic Intraepithelial Neoplasia", The American Journal of Surgical Pathology, 2001, pp. 579-586, vol. 25, No. 5.

Backman et al., "Polarized Light Scattering Spectroscopy for Quantitative Measurement of Epithelial Cellular Structures in Situ", IEEE Journal of Selected Topics in Quantum Electronics, Jul./Aug. 1999, pp. 1019-1999, vol. 5, No. 4.

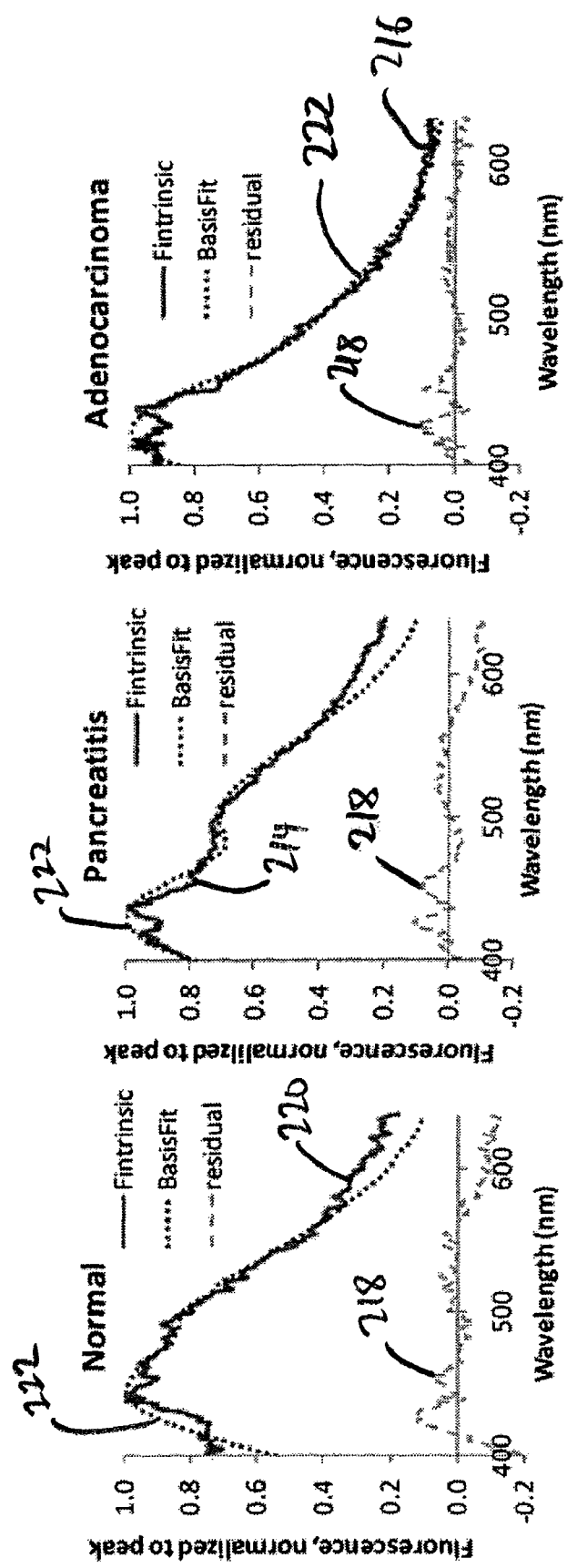

MULTIMODAL SPECTROSCOPIC SYSTEMS AND METHODS FOR CLASSIFYING BIOLOGICAL TISSUE

CROSS-REFERENCE TO RELATED APPLICATION

The instant application claims priority to U.S. Provisional Patent Application Ser. No. 61/058,966, filed Jun. 5, 2008, U.S. Provisional Patent Application Ser. No. 61/242,126 filed Sep. 14, 2009, and as a continuation in part of U.S. Non-Provisional patent application Ser. No. 12/479,600, filed Jun. 5, 2009, the entire disclosures of which are expressly incorporated herein by reference.

STATEMENT REGARDING FEDERALLY SPONSORED RESEARCH OR DEVELOPMENT

The invention was supported, in whole or in part, by a grant NIH CA-114542 from the National Institutes for Health. The Government has certain rights in the invention.

FIELD OF THE INVENTION

The present invention generally relates to medical imaging systems and in particular, to employing multimodal spectroscopy in the diagnosis of biological tissue.

BACKGROUND OF THE INVENTION

The following description of the background of the invention is provided to aid in understanding the invention, but is not admitted to describe or constitute prior art to the invention. The contents of the articles, patents, and patent applications, and all other documents and electronically available information mentioned or cited in this application, are hereby incorporated by reference in their entirety to the same extent as if each individual publication was specifically and individually indicated to be incorporated by reference, including any references cited in the articles, patents, patent applications and documents cited herein. Applicants reserve the right to physically incorporate into this application any and all materials and information from any such articles, patents, patent applications, or other documents.

Pancreatic adenocarcinoma has a five-year survival rate of only 6%, making it the fourth-leading cause of cancer death in the United States. "Cancer Statistics 2010," (website: cancer.org) Current diagnostic procedures are unable to diagnose the disease in its early stages. T. P. Yeo, et al., "Pancreatic cancer," Current Problems in Cancer 26, 176-275 (2002). In addition, diagnosis is compromised due to an overlap of symptoms with pancreatitis (inflammation of the pancreas). As a result, endoscopic ultrasound-guided fine needle aspiration (EUS-FNA), an established method for the diagnosis of pancreatic adenocarcinoma, has only 54% sensitivity for cancer in the setting of pancreatitis.

A. Fritscher-Ravens et al "Comparison of endoscopic ultrasound-guided fine needle aspiration for focal pancreatic lesions in patients with normal parenchyma and chronic pancreatitis," Am. J. Gastroenterol. 97, 2768-2775 (2002). As many as 9% of patients undergo complicated Whipple surgery to remove a significant portion of their pancreas, only to reveal absence of the disease during pathological examination of the resected specimen. S. C. Abraham et al., "Pancreaticoduodenectomy (Whipple Resections) in Patients Without Malignancy: Are They All 'Chronic Pancreatitis'?," The American Journal of Surgical Pathology 27, 110-120 (2003).

Clearly, the detection of the disease in its early stages and its distinction from pancreatitis would greatly reduce the instances of unnecessary surgery, and more importantly, improve the chances of patient survival.

Multiple studies over the years have employed optical techniques as a means for minimally invasive detection of breast, cervical, colon, and esophageal cancer, among other things. Z. Volynskaya et al., "Diagnosing breast cancer using diffuse reflectance spectroscopy and intrinsic fluorescence spectroscopy," J Biomed Opt 13, 024012 (2008); G. Zonios et al., "Diffuse reflectance spectroscopy of human adenomatous colon polyps in vivo," Applied Optics 38, 6628-6637 (1999); S. K. Chang et al., "Model-based analysis of clinical fluorescence spectroscopy for in vivo detection of cervical intraepithelial dysplasia," J Biomed Opt 11, -(2006); and I. Georgakoudi and M. S. Feld, "The combined use of fluorescence, reflectance, and light-scattering spectroscopy for evaluating dysplasia in Barrett's esophagus," Gastrointestinal Endoscopy Clinics of North America 14, 519-537 (2004).

However, there is little support for applying optical methods for pancreatic cancer detection, possibly owing to the relatively inaccessibility of the pancreas.

Recently, it is understood that Optical Coherence Tomography (OCT) has been applied to both in vivo and ex vivo detection of pancreatic cancer. P. A. Testoni et al., "Intraductal optical coherence tomography for investigating main pancreatic duct strictures," Am J Gastroenterol 102, 269-274 (2007); P. A. Testoni et al., "Optical coherence tomography to detect epithelial lesions of the main pancreatic duct: an Ex Vivo study," Am J Gastroenterol 100, 2777-2783 (2005).

Furthermore, Near-Infrared Spectroscopy and Partial-wave microscopic spectroscopy have also been applied in ex vivo studies. V. R. Kondepati et al., "Near-infrared fiber optic spectroscopy as a novel diagnostic tool for the detection of pancreatic cancer," J Biomed Opt 10, -(2005); H. Subramanian et al., "Partial-wave microscopic spectroscopy detects subwavelength refractive index fluctuations: an application to cancer diagnosis," Opt Lett 34, 518-520 (2009).

In the latter, pancreatic cancer cells on microscopic slides were studied. Four-dimensional elastic light-scattering spectroscopy, and low-coherence enhanced backscattering spectroscopy have been employed for the ex vivo study of duodenal tissue based on a field effect hypothesis that predicts changes in the duodenum owing to the presence of cancer in the pancreas. V. Turzhitsky et al., "Investigating population risk factors of pancreatic cancer by evaluation of optical markers in the duodenal mucosa," Dis Markers 25, 313-321 (2008); Y. Liu et al., "Optical markers in duodenal mucosa predict the presence of pancreatic cancer," Clin Cancer Res 13, 4392-4399 (2007).

A number of chemometric and statistical techniques have been used in the literature to develop tissue classification algorithms employing optical spectroscopy data. These include, multiple linear regression analysis, linear discriminant analysis, backpropagating neural network analysis, principal component analysis, logistic discrimination, partial least squares, multivariate linear regression, and support vector machine. N. Ramanujam et al., "Development of a multivariate statistical algorithm to analyze human cervical tissue fluorescence spectra acquired in vivo," Lasers in Surgery and Medicine 19, 46-62 (1996); Z. F. Ge et al., "Identification of colonic dysplasia and neoplasia by diffuse reflectance spectroscopy and pattern recognition techniques," Applied Spectroscopy 52, 833-839 (1998); G. M. Palmer et al., "Comparison of Multiexcitation Fluoroescence and Diffuse Reflectance Spectroscopy for the Diagnosis of Breast Cancer," Ieee T Bio-Med Eng 50, 1233-1242 (2003); S. K. Chang et al., "Combined reflectance and fluorescence spectroscopy for in vivo detection of cervical pre-cancer," J Biomed Opt 10, 024031 (2005); A. Dhar et al., "Elastic scattering spectroscopy for the diagnosis of colonic lesions: initial results of a novel optical biopsy technique," Gastrointest Endosc 63, 257-261 (2006); S. C. Chu et al., "Comparison of the performance of linear multivariate analysis methods for normal and dyplasia tissues differentiation using autofluorescence spectroscopy," Ieee T Bio-Med Eng 53, 2265-2273 (2006); and G. Salomon et al., "The Feasibility of Prostate Cancer Detection by Triple Spectroscopy," Eur Urol, (2008). Additionally, quantitative photon-tissue interaction models of reflectance and fluorescence have been utilized in optical methods for detecting breast cancer Z. Volynskaya, et al., "Diagnosing breast cancer using diffuse reflectance and intrinsic fluorescence spectroscopy," J. Biomed. Opt. 13, 024012 (2008), colon cancer G. Zonios, et al., "Diffuse reflectance spectroscopy of adenomatous colon polyps in vivo," Appl. Opt. 38, 6628-6637 (1999), cervical cancer S. K. Chang, et al., "Model-based analysis of clinical fluorescence spectroscopy for in vivo detection of cervical intraepithelial dysplasia," J. Biomed. Opt. 11, 024008 (2006), and Barrett's esophagus I. Georgakoudi and M. S. Feld, "The combined use of fluorescence, reflectance, and light-scattering spectroscopy for evaluating dysplasia in Barrett's esophagus," Gastroint. Endosc. Clin. N. Am. 14, 519-537 (2004). Recently, photon-tissue interaction modeling was incorporated into an optical study of murine tumors consisting of human pancreatic cancer cells, in order to quantitatively distinguish different tumor regions V. Krishnaswamy, et al., "Quantitative imaging of scattering changes associated with epithelial proliferation, necrosis, and fibrosis in tumors using microsampling reflectance spectroscopy," J. Biomed. Opt. 14, 014004 (2009).

SUMMARY OF THE INVENTION

The invention is generally directed to systems and methods configured for, among other things, directing electromagnetic radiation or light of a plurality of wavelengths onto biological tissue to produce a measurable spectroscopic event; collecting a plurality of spectroscopic response data regarding the biological tissue, which may include fluorescence and reflectance spectra, time-resolved spectroscopy, time-resolved fluorescence spectroscopy or decay measurements; comparing the response data with preset criteria that correlates the collected data with tissue attributes which facilitate a tissue classification, that is, attributes which may be indicative of a particular condition (for example, the presence of a tumor or disease) and/or probative of the relative health of the tissue (for example, normal or abnormal); determining which, if any, of the preset criteria are satisfied; and classifying the tissue based on the tissue attributes identified by the preset criteria satisfied.

The systems and methods described herein are well-suited to be used in conjunction with or as a substitute for random biopsies, since the optical systems and methods are non-invasive, do not require tissue removal, and can be performed in-vivo. Moreover, they are fast (can be applied in real time), are relatively non-expensive, are able to work on microscopic scale, and thus can find very small sites for tissue diagnosis, which may be missed by random biopsies. The systems and methods herein are also well-suited to be used in endoscopic ultrasound-guided procedures and apparatus, or delivered through an endoscope or needle by a trained professional.

In some embodiments, the invention is directed to a method of employing multimodal spectroscopy to classify tissue which includes: illuminating a biological tissue sample to produce a measurable spectroscopic event; collecting spectroscopic response data from the spectroscopic event, wherein the response data includes measurements derived from fluorescence and reflectance signals associated with the tissue sample; comparing the response data with an empirical equation for the reflectance as a function of the tissue and probe properties to determine one or more attributes of the tissue sample, wherein each attribute is at least partially indicative of a tissue classification; and classifying the tissue sample according to the one or more attributes determined.

In some embodiments of the aforementioned method, the step of illuminating the biological tissue sample is configured to produce a plurality of measurable spectroscopic events. The illuminating step may consist of a spectroscopic event including illumination wavelengths of about 400 nm to about 750 nm to facilitate collecting reflectance signal measurements and a spectroscopic event including illumination wavelengths of about 355 to facilitate collecting fluorescence signal measurements.

In some embodiments, the measurements derived from fluorescence and reflectance signals include reflectance, fluorescence, time-resolved spectroscopic measurements, and/or time-resolved fluorescence decay.

In some embodiments, the attributes of the tissue sample include one or more histological features. In some embodiments, the step of classifying the tissue sample further includes classifying the tissue as either normal or abnormal.

In some embodiments, the comparison relates the deviation between the collected spectroscopic response data at a plurality of wavelengths for the tissue sample and spectroscopic response data at the plurality of wavelengths for normal tissue with one or more histological features associated with the tissue sample.

In some embodiments, the attributes of the tissue sample include the nuclear size of cells associated with the tissue sample, the collagen content associated with the tissue sample, the nicotinamide adenine dinucleotide (NADH) content associated with the tissue sample, and the flavin adenine dinucleotide (FAD) content associated with the tissue sample.

In some embodiments, the attributes of the tissue sample further include the refractive index of the cell nuclei.

In some embodiments, the attributes of the tissue sample further include the concentration of oxyhemoglobin, deoxyhemoglobin, and beta carotene, and a pigment packaging factor.

In some embodiments, the attributes of the tissue sample include the nuclear size of cells associated with the tissue sample, the collagen content associated with the tissue sample, the nicotinamide adenine dinucleotide (NADH) content associated with the tissue sample, and the flavin adenine dinucleotide (FAD) content associated with the tissue sample.

Some embodiments of the invention are directed to a system for classifying biological tissue using multimodal optical spectroscopy, which includes: a light source for generating light to illuminate a biological tissue sample; a probe configured for directing the light generated by the light source onto the tissue sample to illuminate the tissue sample and generate a measurable spectroscopic event; one or more detectors configured for collecting spectroscopic response data, wherein the spectroscopic response data includes measurements derived from fluorescence and reflectance signals associated with the tissue sample; and a data processor configured for analyzing the collected spectroscopic response data, comparing the response data with an empirical equation for the reflectance as a function of the tissue and probe properties to determine one or more attributes of the tissue sample, wherein each attribute is at least partially indicative of a tissue classification; and classifying the tissue sample according to the one or more attributes determined.

In some embodiments of the aforementioned system, the probe further includes a plurality of optical fibers. The plurality of optical fibers may be configured for directing light onto the tissue sample, receiving fluorescence and reflectance signals from the tissue sample and directing the received fluorescence and reflectance signals to the one or more detectors, among other things.

In some embodiments, the probe includes a first optical fiber configured for delivering reflectance illumination to the tissue sample, a second optical fiber configured for delivering fluorescence illumination to the tissue sample and a third optical fiber configured for detecting emitted reflectance and fluorescence from the tissue sample. The first, second and third optical fibers may be disposed in a generally triangular cross-sectional arrangement. The system may also include a device or feature which is configured for alternately covering one or more of the optical fibers while leaving others uncovered during the application of light onto the tissue sample.

The detectors in some embodiments of the invention may be configured to derive a variety of measurements from the fluorescence and reflectance signals, such as reflectance, fluorescence and time-resolved fluorescence spectroscopy associated with the tissue sample.

In some embodiments, the light source further includes a light source configured for generating light at wavelengths of about 400 nm to about 750 nm to facilitate collecting reflectance signal measurements and a light source configured for generating light at wavelengths of about 355 to facilitate collecting fluorescence signal measurements.

Some embodiments of the invention are directed to a method employing multimodal optical spectroscopy to classify pancreatic tissue, which includes the steps of: illuminating a pancreatic tissue sample to produce a measurable spectroscopic event; collecting spectroscopic response data from the spectroscopic event, wherein the response data includes measurements derived from fluorescence and reflectance signals associated with the tissue sample; comparing the response data with an empirical equation for the reflectance as a function of the tissue and probe properties to determine one or more histological features associated with the pancreatic tissue sample, wherein the histological features are indicative of a tissue classification of either normal pancreatic tissue, adenocarcinoma or pancreatitis; and classifying the tissue sample as either normal, adenocarcinoma or pancreatitis based on the one or more histological features based on the one or more attributes determined.

The step of comparing the response data in some embodiments of the aforementioned method may further include comparing the response data at wavelengths ranging between about 360 nm to about 750 nm. Also, in some embodiments, the measurements derived from fluorescence and reflectance signals associated with the tissue sample include fluorescence, reflectance and time-resolved fluorescence decay spectroscopic measurements, or any other complementary spectroscopic measurements.

These and other aspects of the invention will become more readily apparent to those of ordinary skill in the art from the following detailed description when considered in connection with the accompanying figures.

BRIEF DESCRIPTION OF THE DRAWINGS

FIGS. 3A, 3B and 3C provide graphs illustrating intrinsic fluorescence spectra of normal pancreatic tissue (FIG. 3A), pancreatitis (FIG. 3B), and pancreatic adenocarcinoma (FIG. 3C), shown with a representative fit to a linear combination of measured and blue-shifted collagen, NADH, and FAD basis spectra;

DETAILED DESCRIPTION OF INVENTION

Figures 1A, 1B:
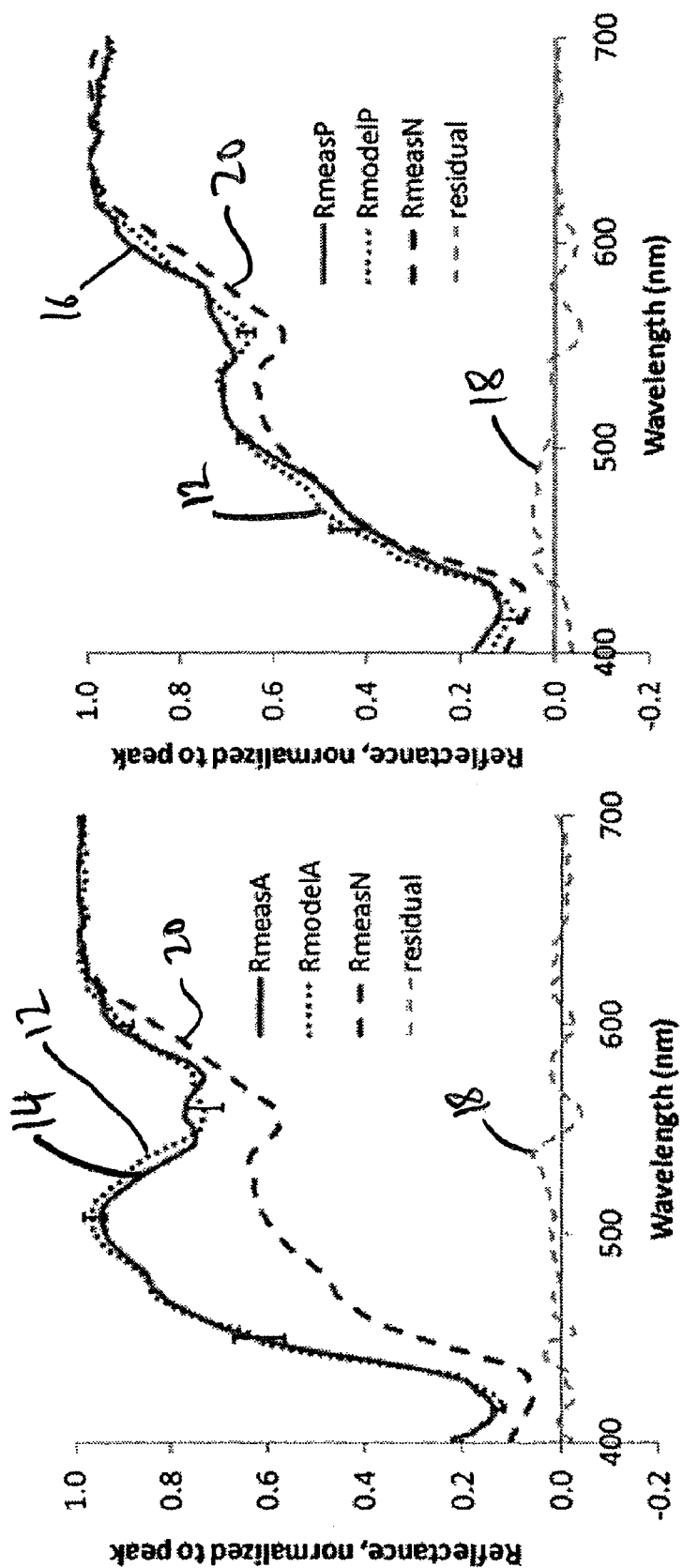
FIGS. 1A and 1B provide graphs illustrating a representative fit of a mathematical model, formed according to some embodiments of the invention, versus average measured result for reflectance spectra of pancreatic adenocarcinoma (FIG. 1A) and pancreatitis (FIG. 1B), with residuals.

Some embodiments of the invention employ multimodal optical spectroscopic systems and methods to obtain data from biological tissue and compare the data with preset criteria configured to aid in the diagnosis of the tissue health or condition, wherein the preset criteria relates the data with the most probable attributes of the tissue. The multimodal spectroscopic systems employed may include fluorescence spectroscopy, reflectance spectroscopy and time-resolved spectroscopy, among others.

In some embodiments, data obtained through multimodal optical spectroscopy is correlated with the results of a microscopic histological examination of a normal tissue sample to develop the preset criteria by which further tissue samples are to be assessed. In particular, the preset criteria may be based on a relationship between spectral data and the histological aspects of the tissue which are most likely to be indicative of a specific attribute so as to lead to a unique classification of the tissue. For example, the preset criteria may ultimately be used to provide attributes such as the NADH content, FAD content, collagen content and/or nuclear size values associated with the tissue, or any other characteristics which are probative of tissue health, indicative of certain conditions, or otherwise provide insight into the relative health of the tissue.

Thus, systems and methods of the invention can be used to facilitate real-time (or near real-time) diagnosis of further tissue samples and may be employed with excised tissue or in vivo. Systems and methods of the invention may be used to ascertain tissue conditions and classify tissue during a surgical procedure. The systems and methods discussed herein may be utilized to guide a biopsy procedure. For example, systems and methods of the invention may be incorporated for a variety of fiber probe configurations through any kind of endoscope or needle in a clinic or other facility or with endoscopic ultrasound-guided fine needle aspiration (EUS-FNA) procedures.

As mentioned above, the preset criteria relate measured data to tissue attributes in a manner which facilitates a tissue classification. Depending on the application, tissue classifications may include normal, abnormal, inflammation, disease or adenocarcinoma, for example. In some embodiments, the measured data may linked by the preset criteria to histological features which are hallmarks of particular tissue conditions such as adenocarcinoma. In this manner, some embodiments of the invention utilize the measured data to quantitatively distinguish between normal and abnormal tissue conditions.

Systems and methods of the invention employ multimodal optical spectroscopy, and may include exposing biological tissue to a source of electromagnetic radiation to produce a spectral event, collecting spectral response data regarding the tissue at a plurality of wavelengths, correlating the spectral response data with the histology of the tissue based on preset criteria, and classifying the tissue condition based on the preset criteria satisfied. In some embodiments, the spectral response data collected includes fluorescence, reflectance and time-resolved fluorescence decay information, but may include any combination of parameters derived from the spectral event or response data that are likely to provide complementary information about the biochemical, architectural and morphological state of the tissue of interest.

The preset criteria may be derived by a variety of methods, such as the empirical data collection and mathematical modeling techniques discussed herein with respect to pancreatic tissue. Although the illustrations and examples herein focus on pancreatic tissues, it should be readily apparent that the invention is not to be limited to pancreatic tissues, and mathematical models of the invention are also of potential use for optical diagnostic applications in other biological tissues. It should be understood that the embodiments of the invention may be useful for various applications and procedures throughout the medical arts. Thus, the techniques and embodiments discussed herein should not be construed as limiting, as analyzing pancreatic tissue to differentiate between normal pancreatic tissue, pancreatitis, and adenocarcinoma is merely an example of a suitable application for the embodiments of the invention.

Illustration I

1. Introduction

Systems and methods discussed herein advantageously provide the ability to quantitatively explain prominent disease-related changes to human pancreatic tissue in terms of biologically meaningful parameters based on spectral data consisting of collected fluorescence and reflectance spectra. The systems and methods of the invention further provide the ability to classify pancreatic tissue as normal, pancreatic or adenocarcinoma. In some embodiments, the preset criteria is derived from mathematical modeling of experimentally measured spectral data used to quantitatively describe differences in the reflectance and fluorescence spectra of normal pancreatic tissue, pancreatic adenocarcinoma, and pancreatitis.

For example, it has been found that pancreatic adenocarcinoma has larger nuclei than benign pancreatic tissue, and both adenocarcinoma and chronic pancreatitis have more collagenous stroma than normal pancreatic tissue. The mathematical model of reflectance quantitatively linked increased nuclear size in adenocarcinoma to changes in the measured reflectance spectra, particularly within the range from about 455 nm to about 525 nm. The fluorescence model quantitatively linked increased collagen content in pancreatitis and adenocarcinoma to changes in the composition of the measured fluorescence spectra. Fitting the reflectance model to the experimental data also enabled the extraction of values for the optical absorption and scattering coefficients of human pancreatic tissues.

The mathematical model of some embodiments provided a quantitative link between optical spectroscopy and tissue histology as shown in Table 1, suggesting a potential clinical application of optical spectroscopy and modeling to minimally invasive early cancer diagnostics in the pancreas.

TABLE 1

Key histological features of pancreatic tissues detected by optical spectroscopy

| Pancreatic tissue | Key histological features (relative to normal pancreatic tissue) | Optical signature found in |
|---|---|---|
| Adenocarcinoma | Increased nuclear size | Reflectance spectra |
| | Greater stromal collagen content | Fluorescence spectra |
| Pancreatitis | Greater stromal collagen content | Fluorescence spectra |

2. Clinical Measurements of Tissue Optical Spectra

In this embodiment, a Reflectance and Fluorescence Lifetime Spectrometer (RFLS) was used to obtain reflectance and fluorescence measurements of human pancreatic tissue within about 15 minutes of removal via Whipple resection at the University of Michigan Medical Center. Reflectance measurements were acquired by using a CW tungsten halogen lamp (e.g., HL 2000FHSA, Ocean Optics, Dunedin, Fla.) to deliver white light (about 400 to about 750 nm wavelength) to the tissue; fluorescence measurements utilized a 355 nm pulsed excitation source (e.g., PNV001525-140, JDS Uniphase, San Jose, Calif.). A spectrograph (e.g., MS 125, Oriel Instruments, Stratford, Conn.) and an intensified charge-coupled device (ICCD) camera (e.g., ICCD 2063, Andor Technology, Belfast, Northern Ireland) were used to detect tissue reflectance (about 400 to about 750 nm) and fluorescence (about 360 to about 700 nm) spectra. The light from the lamp and the laser was delivered to the tissue via two separate optical fibers with core diameters of 600 µm. The reflected or emitted fluorescence photons from the tissue were collected and transported to the detectors by a third identical fiber.

Measurements were taken at five sites on each tissue specimen. One pancreatectomy specimen was evaluated from each of two different patients. Each measured site was biopsied under the supervision of a clinical pathologist, and the biopsied samples were evaluated histologically. For the first patient, two of the sites were histologically normal and three were pancreatitis, while for the second patient, all five sites sampled were adenocarcinoma. There were noticeable differences in both the reflectance and fluorescence spectra of the three tissue types, most notably around 500 nm for the reflectance spectra and near 400 nm for the fluorescence spectra.

3. Mathematical Model of Reflectance Spectra: Theory and Results 3.1 Modeling Scattering and Absorption Coefficients of Pancreatic Tissues The lineshapes of reflectance spectra from biological tissues are known to be primarily dependent on the absorption and scattering coefficients of the media. Absorbers such as blood will attenuate the light, while scatterers such as cell nuclei and collagen fibers will change the paths of the photons, eventually leading some of them back to the tissue surface. Mie theory was used to describe the scattering coefficient $\mu_s$, as a function of wavelength, in terms of the size and density of the scatterers in the tissue. A. Sefkow, et al., "Method for Measuring Cellular Optical Absorption and Scattering Evaluated Using Dilute Cell Suspension Phantoms," Appl. Spectrosc. 55, 1495-1501 (2001); C. F. Bohren and D. R. Huffman, *Absorption and Scattering of Light by Small Particles* (Wiley, 1983); L. T. Perelman, et al., "Observation of Periodic Fine Structure in Reflectance from Biological Tissue: A New Technique for Measuring Nuclear Size Distribution," Phys. Rev. Lett. 80, 627-630 (1998); and I. S. Saidi, et al. "Mie and Rayleigh modeling of visible-light scattering in neonatal skin," Appl. Opt. 34, 7410-7418 (1995).

Two Mie theory terms were used: one for spherical scatterers (cell nuclei) and another for cylindrical scatterers (collagen fibers). For the spherical Mie scattering term, the Van de Hulst approximation was used:

$$\mu_s(\lambda) = \frac{1}{2}\pi N_s L^2 \left[1 - \frac{\sin(2\delta/\lambda)}{(\delta/\lambda)} + \left(\frac{\sin(\delta/\lambda)}{(\delta/\lambda)}\right)^2\right]; \quad (1)$$

$$\delta = \pi L(n_s - n_m).$$

In Eq. (1), Lo is the scatterer diameter, Ns is the number of scatterers per unit volume, and $n_s$ ($n_m$) is the index of refraction of the scatterer (surrounding medium). The wavelength $\lambda$ is defined as $\lambda_{vac}/n_m$, where $\lambda_{vac}$ is the wavelength of the incident light in vacuum. For all pancreatic tissue types in this study, $n_m$ was assumed to be 1.33 (for water), while $n_s$ was set as a free parameter. The values of L and $N_s$ were estimated from histology to be 9 µm and $7 \times 10^7$ cm$^{-3}$, respectively. The parameter $N_s$ was kept constant for all tissue types. For both pancreatitis and adenocarcinoma, a dilation factor $L_d/L_o$ was applied to the nuclear diameter. The cylindrical scattering term was modeled by a combination of Bessel functions, in which the diameter and refractive index of the collagen fibers were 3 µm and 1.35, respectively. The spherical and cylindrical Mie scattering terms were chosen over the commonly-used approximation $\mu_s = A\lambda^{-b}$ because they are explicit functions of scatterer size. The absorption coefficient $\mu_a$ was modeled as a linear combination of the extinction coefficients of oxy- and deoxy-hemoglobin, weighted according to their concentrations in the tissue:

$$\mu_a(\lambda) = [Hb]\epsilon_{Hb} + [HbO_2]\epsilon_{HbO_2}. \quad (2)$$

G. Zonios, et al., "Diffuse reflectance spectroscopy of adenomatous colon polyps in vivo," Appl. Opt. 38, 6628-6637 (1999).

3.2 Modeling Key Features in Reflectance Spectra of Pancreatitis and Adenocarcinoma The key diagnostic feature of the measured reflectance was increased amplitude between 455 nm and 525 nm in the adenocarcinoma spectra, relative to normal pancreatic tissue spectra. An empirical model, previously shown to be accurate in the case of small source-detector separations, was used to model this feature by describing the reflectance spectra $R_i^{EMP}(\lambda)$ as functions of tissue absorption and scattering:

$$R_i^{EMP}(\lambda) = a\mu_s'(\lambda)\exp\left(-\frac{C_{corr}(\lambda)\mu_a(\lambda)b}{[C_{corr}(\lambda)\mu_a(\lambda)\mu_s'(\lambda)]^c}\right). \quad (3)$$

R. Reif, et al., "Analysis of changes in reflectance measurements on biological tissues subjected to different probe pressures," J. Biomed. Opt. 13, 010502 (2008); R. Reif, et al., "Analytical model of light reflectance for extraction of the optical properties in small volumes of turbid media," Appl. Opt. 46, 7317-7328 (2007).

In Eq. (3), $\mu_s'(\lambda)$ is the reduced scattering coefficient, equal to $\mu_s(1-g)$, where g is the anisotropy of the tissue (set to 0.9 for all $\lambda$). The factor $C_{corr}(\lambda)$ describes the confinement of oxy- and deoxy-hemoglobin to cylindrical blood vessels. R. L. P. van Veen et al., "Diffuse-reflectance spectroscopy from 500 to 1060 nm by correction of inhomogeneously distributed absorbers," Opt. Lett. 27, 246-248 (2002). The parameters a, b, and c are fitting constants (related to probe design) whose respective values were estimated to be 0.11, 0.22, and 0.2. These values do not vary significantly when the tissue-probe refractive index mismatch is changed. The value of b is somewhat dependent on probe source-detector separation, but changing b by as much as 50% was found to have very little effect on the modeled pancreatic tissue spectra. Since the reflectance model (Eq. (4)) employed in this study only utilizes ratios (and not raw values) of $R_i^{EMP}$ for different tissue types, it was considered reasonable to approximate a, b, and c as 0.11, 0.22, and 0.2 in Eq. (3). For the remainder of the text, the subscript i in Eq. (3) will be denoted as N for normal pancreatic tissue, P for pancreatitis, or A for pancreatic adenocarcinoma.

To model the reflectance spectra of diseased pancreatic tissue, Eq. (3) was used to generate a wavelength-resolved scaling factor to transform the experimentally measured reflectance spectrum $R^{MEAS}_N(\lambda)$ of normal pancreatic tissue into an accurate model for the adenocarcinoma reflectance spectrum $R^{MODEL}_A(\lambda)$ and the pancreatitis reflectance spectrum $R^{MODEL}_P(\lambda)$, according to the equations:

$$R_A^{MODEL}(\lambda)=R_N^{MEAS}(\lambda)(R_A^{EMP}(\lambda)/R_N^{EMP}(\lambda)); \quad (4)$$

$$R_P^{MODEL}(\lambda)=R_N^{MEAS}(\lambda)(R_P^{EMP}(\lambda)/R_N^{EMP}(\lambda)). \quad (5)$$

Optimal fits of Eqs. (4) and (5) to the respective measured adenocarcinoma and pancreatitis reflectance spectra were determined via minimization of a cost function $C_R$, which was equal to the average magnitude of the difference between the reflectance model and measured reflectance spectrum over the 400-700 nm wavelength range. For each tissue type, every individual measured spectrum was first normalized to peak intensity, then these spectra were averaged and the result was normalized to peak intensity again. All of the modeled reflectance spectra were also normalized to peak intensity.

In the fitting procedure described above, the nuclear dilation factor $L_d/L_o$ for diseased pancreatic tissue (adenocarcinoma and pancreatitis) was varied from 1.0 to 1.9 in steps of 0.1, and the nuclear refractive index $n_{sd}$ of diseased pancreatic tissue was varied from 1.370 to 1.400, in steps of 0.005. The total hemoglobin concentration [Hb]tot was varied from 15 µM to 25 µM for normal pancreatic tissue and 2.5 µM to 25 µM for diseased tissue (in steps of 2.5 µM for all tissue types). The blood oxygen saturation $SO_2$ was varied from 0.1 to 0.9 (in steps of 0.2) for all tissue types. The fitting procedure described above was performed for each of three different values of the nuclear refractive index nsn of normal pancreatic tissue: 1.370, 1.375, and 1.380. This range and these values were identified in part because of the results of studies conducted on freshly excised diseased and normal human tissues [V. Backman, R. Gurjar, K. Badizadegan, L. Itzkan, R. R. Dasari, L. T. Perelman, and M. S. Feld, "Polarized light scattering spectroscopy for quantitative measurement of epithelial cellular structures in situ," IEEE J. Sel. Top. Quantum Electron. 5(4), 1019-1026 (1999)], and in part because we observed that the algorithm extracted physically reasonable values of both $L_d/L_o$ and $n_{sd}$ that did not vary much as $n_{sn}$ was changed. The set of free parameter values that minimized $C_R$ was extracted from each fit, as reported below. The fitting method described here was compared with a nonlinear least-squares method, and t-tests demonstrated that there were no statistically significant differences (p>0.25) between the tissue parameters extracted from the two fitting methods.

In the diagnostically important wavelength range between about 455 and about 525 nm, where the adenocarcinoma reflectance spectra differed significantly from both the normal and pancreatitis spectra, the error in fit between the adenocarcinoma model and measured adenocarcinoma data was less than 5%.

FIGS. 1A and 1B illustrates an aspect of an embodiment of the invention and provides a representative fit of a mathematical model 12 (dotted lines) versus average measured result for reflectance spectra (solid lines) of pancreatic adenocarcinoma (FIG. 1A) 14 and pancreatitis (FIG. 1B) 16, with residuals (small dotted lines) 18. The experimentally obtained reflectance spectrum for normal pancreatic tissue (dashed lines) 20 is shown on both plots for comparison.

The optimal fits between the predicted and measured adenocarcinoma reflectance spectra extracted a (mean±standard deviation) value of $L_d/Lo=1.33\pm0.06$ for the nuclear dilation factor and a value of $n_{sd}=1.375$ for the nuclear refractive index. The optimal fits between the predicted and measured pancreatitis reflectance spectra extracted a (mean±standard deviation) value of $L_d/Lo=1.03\pm0.06$ for the nuclear dilation factor and $n_{sd}=1.372\pm0.003$ for the nuclear refractive index. The model revealed that differences in the reflectance spectra of normal pancreatic tissue, pancreatitis, and adenocarcinoma could be quantitatively linked to an increase in nuclear size for adenocarcinoma relative to pancreatitis and normal tissue, a result that is supported by histology [F. Lin, and G. Staerkel, "Cytologic criteria for well differentiated adenocarcinoma of the pancreas in fine-needle aspiration biopsy specimens," Cancer 99(1), 44-50 (2003).; M. B. Cohen, D. P. Egerter, E. A. Holly, D. K. Ahn, and T. R. Miller, "Pancreatic adenocarcinoma: regression analysis to identify improved cytologic criteria," Diagn. Cytopathol. 7(4), 341-345 (1991).; R. J. Sears, C. W. Duckworth, C. Decaestecker, N. Bourgeois, T. Ledent, J. Deviere, I. Salmon, R. Kiss, and P. Yeaton, "Image cytometry as a discriminatory tool for cytologic specimens obtained by endoscopic retrograde cholangiopancreatography," Cancer 84(2), 119-126 (1998).].

These choices of parameters were in good agreement with results from histology and previous literature. M. Chandra, et al., "Probing pancreatic disease using tissue optical spectroscopy," J. Biomed. Opt. 12, 060501 (2007); M. Chandra, et al., "Pancreatic tissue assessment using fluorescence and diffuse reflectance spectroscopy," Proc. SPIE 6628, 66281R (2007), 8 pgs; T. Imamura, et al., "Quantitative analysis of collagen and collagen subtypes I, III, and V in human pancreatic cancer, tumor-associated chronic pancreatitis, and alcoholic chronic pancreatitis," Pancreas 11, 357-364 (1995). The model revealed that differences in the reflectance spectra of normal pancreatic tissue, pancreatitis, and adenocarcinoma were largely due to an increase in nuclear size for adenocarcinoma relative to pancreatitis and normal tissue.

The spectra from FIGS. 1A and 1B were also compared with a previously published reflectance spectrum taken in vivo from a pancreatic adenocarcinoma xenograft created by injecting human pancreatic cancer cells into the pancreas of a Non-Obese Diabetic/Severe Combined Immunodeficiency (NOD/SCID) mouse. Due to the suppressed immune response in SCID mice, the xenograft had a very low amount of collagen relative to cells. The xenograft also contained more blood than the ex vivo-obtained human pancreatic tissue samples. In spite of these differences, the reflectance spectrum of the xenograft was similar to that of freshly excised human adenocarcinoma from 400-475 nm, a result attributed to the increased size of the cell nuclei in both the xenograft and the ex vivo-obtained adenocarcinoma tissue samples.

3.3 Extracting Scattering and Absorption Coefficients from Reflectance Data

Model fits to experimental data were employed to extract wavelength-resolved absorption and scattering coefficients for each tissue type via Eqs. (1) and (2) and the formula for Mie scattering from cylinders. The results shown in FIGS. 2A and 2B represent a measurement of absorption and scattering coefficients of human pancreatic tissues.

Figures 2A, 2B:
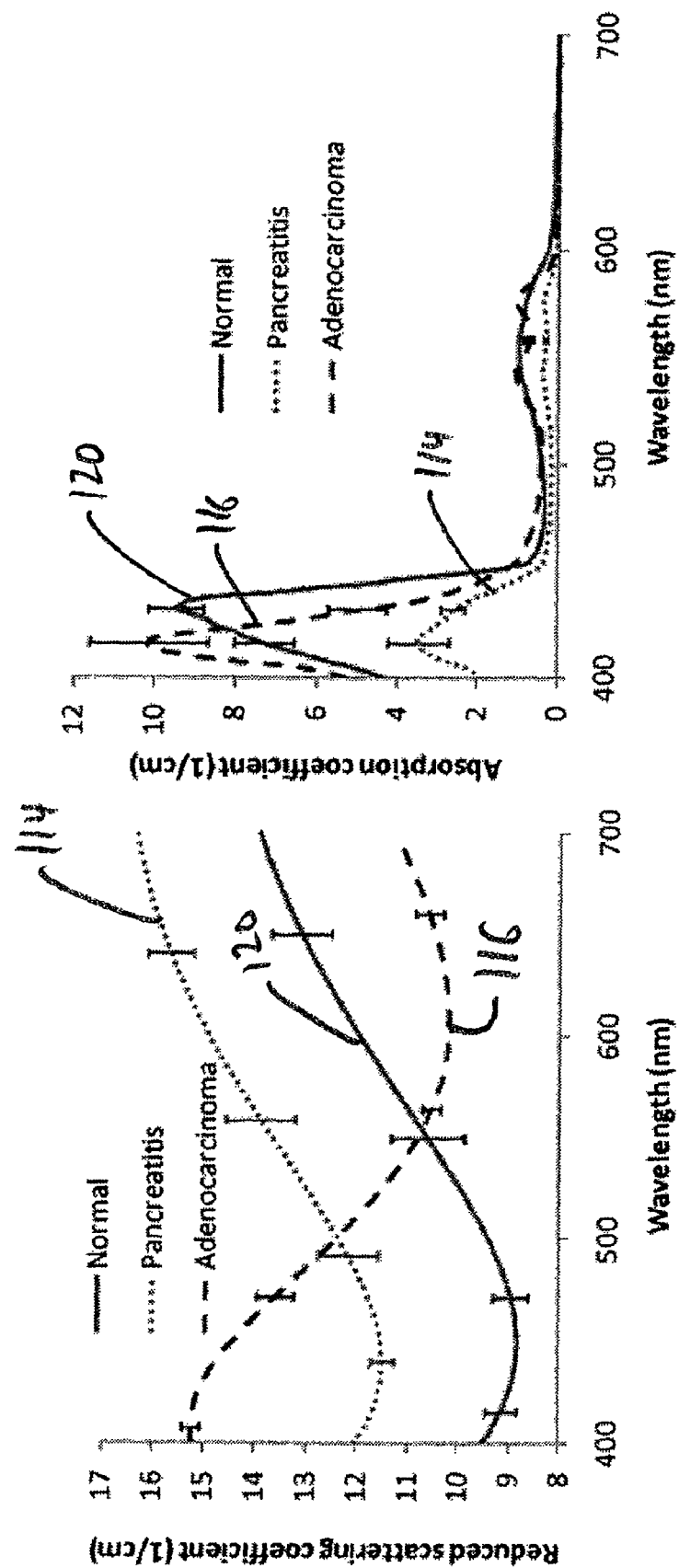
FIGS. 2A and 2B provide graphs illustrating wavelength-resolved scattering (FIG. 2A) and absorption (FIG. 2B) coefficients of normal pancreatic tissue, pancreatic adenocarcinoma, and pancreatitis, extracted from representative fits of experimental data to the reflectance model.

As shown in FIGS. 2A and 2B, wavelength-resolved scattering (FIG. 2A) and absorption (FIG. 2B) coefficients of normal pancreatic tissue (solid lines) 120, pancreatic adenocarcinoma (dashed lines) 116, and pancreatitis (dotted lines) 114, extracted from representative fits of experimental data to the reflectance model. The difference in shape of the adenocarcinoma scattering coefficient can be attributed to the modeling of the adenocarcinoma cellular nuclear diameter and refractive index as being different from those of normal pancreatic tissue and pancreatitis.

The values of the coefficients in FIGS. 2A and 2B are in the range expected for gastrointestinal tissue. K. Vishwanath and M.-A. Mycek, "Do fluorescence decays remitted from tissues accurately reflect intrinsic fluorophore lifetimes?" Opt. Lett. 29, 1512-1514 (2004). Since the absorption coefficient can yield quantitative information about the blood content of the tissue, the mathematical model has the potential to be useful for in vivo studies, in which the presence of blood will likely be more significant.

4. Extracting and Modeling Intrinsic Fluorescence: Theory and Results 4.1 Correcting Fluorescence Data for Scattering- and Absorption-related Artifacts Once the fits of the reflectance model to the adenocarcinoma and pancreatitis data were obtained, the extracted wavelength-resolved scattering coefficients $\mu_s(\lambda)$ (FIG. 2A) were then used to remove artifacts of scattering and absorption from the measured fluorescence spectra of normal, pancreatitis and adenocarcinoma tissue. To perform this task, a separate Beer-Lambert attenuation factor was constructed for each tissue type by using the extracted $\mu_s(\lambda)$ and $\mu_a(\lambda)$ values specific to that tissue type. The intrinsic fluorescence spectrum $F_{INTRINSIC}(\lambda)$ was then extracted according to the equation:

$$F_{INTRINSIC}(\lambda)=F_{MEAS}(\lambda)\exp([\mu_a(\lambda)+\mu_s(\lambda)]z). \quad (6)$$

The variable z represents the average depth that photons will travel in the tissue, and it was estimated from time-resolved Monte Carlo simulations [K. Vishwanath, and M.-A. Mycek, "Time-resolved photon migration in bi-layered tissue models," Opt. Express 13(19), 7466-7482 (2005).] to be 0.064 cm for all tissue types. To obtain this value, time-resolved Monte Carlo simulations were run for pancreatic tissue models whose absorption and scattering coefficients were representative of those shown in FIGS. 2A and 2B. The average depth of photon travel was determined by finding the time at which the greatest number of simulated photons exited the tissue, multiplying that by the speed of light in the medium, and dividing by two to account for the photons' travel back to the surface once they reached their point of greatest depth in the tissue.

4.2 Fitting Intrinsic Fluorescence to Endogenous Fluorophore Component Spectra

Once the intrinsic fluorescence spectra were obtained for each tissue type, their lineshapes could be decomposed into the component spectra of collagen, NADH, and FAD, three principal contributors to tissue autofluorescence in the 400-700 nm wavelength range. For each tissue type, the intrinsic fluorescence spectrum was fit to a linear combination (BasisFit($\lambda$)) of experimentally measured basis spectra of collagen, NADH, and FAD:

$$\text{BasisFit}(\lambda)=C_{COLLAGEN}F_{COLLAGEN}(\lambda)+C_{NADH}F_{NADH}(\lambda)+C_{FAD}F_{FAD}(\lambda). \quad (7)$$

To fit the intrinsic fluorescence spectra (FIGS. 3A, 3B and 3C) to Eq. (7), each of the basis spectra ($F_{COLLAGEN}(\lambda)$, $F_{NADH}(\lambda)$, and $F_{FAD}(\lambda)$) was blue-shifted by about 12 nm, which accounted for the fact that the component spectra were measured in various chemical solvents and not within a biological tissue environment.

FIGS. 3A, 3B and 3C illustrate intrinsic fluorescence spectra (solid lines) of normal pancreatic tissue 220 (FIG. 3A), pancreatitis (FIG. 3B) 214, and pancreatic adenocarcinoma 216 (FIG. 3C), shown with a representative fit to a linear combination 222 (dotted lines) with residuals 218 (small dotted line) of measured and blue-shifted collagen, NADH, and FAD basis spectra.

The deviation of the basis fits to the intrinsic fluorescence spectra of normal pancreatic tissue and pancreatitis around 600 nm may be attributed to the fact that the model does not include porphyrin fluorescence, which is known to peak around 635 nm when excited with 380-440 nm light. P. Hillemanns, et al., "Lymph node metastasis detection of ovarian cancer by porphyrin fluorescence photodetection: case report," Lasers Med. Sci. 22, 131-135 (2007).

The purpose of the fluorescence model was not to obtain an exact fit to every point on the intrinsic fluorescence spectra, but rather to interpret key features of the fluorescence from normal pancreatic tissue, pancreatitis, and pancreatic adenocarcinoma. Since the spectra were normalized to the peak, the intrinsic fluorescence between 500 and 550 nm (where intracellular NADH and FAD emit prominently) is expected to decrease in pancreatitis and adenocarcinoma, where there is increased extracellular stromal collagen content. In this diagnostically-relevant region, the error in fit between Eq. (7) and the intrinsic fluorescence was less than 4% for normal pancreatic tissue and pancreatitis, and less than 8% for adenocarcinoma.

The data from FIGS. 3A, 3B and 3C shows that the mathematical model of intrinsic fluorescence agreed well with histology of tissue samples from patients involved in the study and described in Table 1. The values of the collagen fit coefficients $C_{COLLAGEN}$ (Table 2) correlated well with the amount of collagen incursion amidst the cells in the tissue samples examined via histology.

TABLE 2

Fit coefficients Ci (percentage contributions) for collagen, NADH, and FAD basis spectra to intrinsic fluorescence spectra of normal pancreatic tissue, pancreatitis, and pancreatic adenocarcinoma.

|  | Normal | Pancreatitis | Adenocarcinoma |
| --- | --- | --- | --- |
| $C_{COLLAGEN}$ | 0.6 (35%) | 0.9 (56%) | 0.9 (82%) |
| $C_{NADH}$ | 0.8 (47%) | 0.3 (19%) | 0.1 (9%) |
| $C_{FAD}$ | 0.3 (18%) | 0.4 (25%) | 0.1 (9%) |

The data in FIGS. 3A, 3B and 3C were also compared to the intrinsic fluorescence extracted from a fluorescence spectrum obtained in vivo from a pancreatic adenocarcinoma xenograft in a NOD/SCID mouse. M. Chandra, et al., "Probing pancreatic disease using tissue optical spectroscopy," J. Biomed. Opt. 12, 060501 (2007). Mathematical modeling showed that the xenograft fluorescence could be mostly attributed to intracellular components, a conclusion that made sense given that the xenograft tumor was predominantly comprised of cells.

5. Discussion and Conclusions

5.1 Overview of Mathematical Models Developed

In this illustration of embodiments of the invention, mathematical models of reflectance and intrinsic fluorescence were developed and employed to quantitatively describe the effects of key histologically-observed tissue parameters on the measured optical spectra of pancreatitis and pancreatic adenocarcinoma (relative to normal pancreatic tissue). An empirical mathematical model of reflectance was able to fit the prominent feature in the adenocarcinoma spectrum (increased amplitude from about 455 to about 525 nm, relative to normal pancreatic tissue) with less than 6% error. Fitting the reflectance model to the measured optical spectra enabled the extraction of wavelength-resolved absorption and scattering coefficients of human pancreatic tissues. Obtaining values for the optical coefficients is an important result, because knowledge of these coefficients is essential for accurate computational studies of photon migration in pancreatic tissue models. For example, one such computational method is Monte Carlo simulation, which is accurate throughout optical parameter space for modeling photon transport in biological tissue. L. Wang, et al., "MCML—Monte Carlo modeling of light transport in multi-layered tissues," Computer Methods and Programs in Biomedicine 47, 131-146 (1995); K. Vishwanath and M.-A. Mycek, "Time-resolved photon migration in bi-layered tissue models," Opt. Expr. 13, 7466-7482 (2005).

The optical scattering coefficients extracted from the reflectance fits were used to correct the measured fluorescence spectra in an algorithm that removed tissue absorption and scattering artifacts. The resulting "intrinsic" endogenous fluorescence spectra were fit to a linear combination of basis spectra from native tissue fluorophores (collagen, NADH, FAD) to obtain the relative contributions from both extracellular (collagen, about 400 to about 450 nm emission peak) and intracellular (NADH and FAD, about 500 nm to about 600 nm emission peak) autofluorescence for each tissue type. The relative contribution of collagen was found to be greater in the intrinsic fluorescence spectra of pancreatitis and adenocarcinoma. Since the spectra were normalized to the peak, the pancreatitis and adenocarcinoma spectra exhibited a decrease in amplitude in the about 500 to about 550 nm range, where NADH and FAD emission are prominent. These results were consistent with the increased collagen fibrosis seen in histology of pancreatitis and adenocarcinoma. T. Imamura, et al., "Quantitative analysis of collagen and collagen subtypes I, III, and V in human pancreatic cancer, tumor-associated chronic pancreatitis, and alcoholic chronic pancreatitis," Pancreas 11, 357-364 (1995); J. Köninger, et al., "Overexpressed Decorin in Pancreatic Cancer: Potential Tumor Growth Inhibition and Attenuation of Chemotherapeutic Action," Clin. Cancer Res. 10, 4776-4783 (2004).

5.2 Correlation of Optical Tissue Models with Histology

As seen in FIGS. 1A and 1B, FIGS. 3A, 3B and 3C, and Table 3, empirical models of reflectance and intrinsic fluorescence were able to quantitatively describe the differences between normal pancreatic tissue, adenocarcinoma, and pancreatitis in terms of histologically observed changes in biologically meaningful parameters. The reflectance spectra of cancerous tissue differed most noticeably from normal pancreatic tissue at around 500 nm, a change that could be quantitatively linked, via spherical Mie scattering, to larger cell nuclei in pancreatic adenocarcinoma. Subtle differences in the reflectance spectra at around 400 nm to about 425 nm and about 450 nm to about 550 nm were also found, via modeling of cylindrical Mie scattering, to correlate with the increased number of collagen fibers in both pancreatitis and cancer. These results agree with histology in that both pancreatitis and pancreatic adenocarcinoma are marked by greater collagen content than normal pancreatic tissue, but only adenocarcinoma is characterized by larger cell nuclei. R. H. Hruban, et al., "Pancreatic Intraepithelial Neoplasia: A New Nomenclature and Classification System for Pancreatic Duct Lesions," Am. J. Surg. Path. 25, 579-86 (2001); R. H. Hruban, et al., "An Illustrated Consensus on the Classification of Pancreatic Intraepithelial Neoplasia and Intraductal Papillary Mucinous Neoplasms," Am. J. Surg. Path. 28, 977-87 (2004).

TABLE 3

Prominent disease-related changes in histology features and measured optical spectra of pancreatic tissues, along with corresponding changes made to mathematical models of reflectance and fluorescence.

| Pancreatic tissue | Adenocarcinoma | Pancreatitis |
| --- | --- | --- |
| Key histological features (relative to normal pancreatic tissue) | Increased nuclear size Greater stromal collagen content | Greater stromal collagen content |
| Optical signature (relative to normal pancreatic tissue) | Increased amplitude of reflectance spectrum from 455 to 525 nm<br>Spectral lineshape change in intrinsic fluorescence spectrum from 500 to 550 nm | Spectral lineshape change in intrinsic fluorescence spectrum from 500 to 550 nm |
| Mathematically modeled by | Multiplying spherical scatterer diameter $L_o$ by 1.33 for reflectance model<br>Increasing percentage contribution of collagen basis spectrum from 35% to 82% in fit to intrinsic fluorescence | Increasing percentage contribution of collagen basis spectrum from 35% to 56% in fit to intrinsic fluorescence |
| Mean error in fit of model to experimentally measured data in diagnostically relevant region | Less than 6% from 455 to 525 nm for adenocarcinoma reflectance model<br>Less than 8% from 500 to 550 nm for all intrinsic fluorescence models | Less than 4% from 500 to 550 nm for all intrinsic fluorescence models |

The intrinsic fluorescence model showed that for both pancreatitis and adenocarcinoma, there was an increased contribution from the collagen in the stroma, relative to normal pancreatic tissues. This result is consistent with the histological observation that the change from normal pancreatic tissue to both pancreatitis and adenocarcinoma is characterized by increased collagen amidst the cells. However, the intrinsic fluorescence spectra of pancreatitis and cancer were also shown to be different from each other. Whereas the reflectance model was most useful for discriminating pancreatic adenocarcinoma from pancreatitis, the intrinsic fluorescence model was more effective at distinguishing between all three tissue types. In any case, the use of the reflectance data to extract the intrinsic fluorescence lends credence to the idea that combining reflectance and fluorescence spectroscopy has a diagnostic advantage over using just one of these modalities to detect pancreatic cancer.

5.3 Comparison of Empirical Reflectance Model with Diffusion Approximation

The empirical reflectance model was compared with the diffusion approximation, which is often employed to extract tissue absorption and scattering properties from experimentally measured tissue reflectance spectra. G. Zonios, et al., "Comparative evaluation of two simple diffuse reflectance models for biological tissue applications," Appl. Opt. 47, 4965-4973 (2008). When the reflectance fitting procedure was employed with a subset of the hemoglobin concentration and blood oxygen saturation ranges, the diffusion approximation model was noticeably less effective than the empirical model for fitting the adenocarcinoma reflectance spectrum. In the diagnostically-relevant wavelength range of 455-525 nm, the error in fit to the measured adenocarcinoma spectrum was less than 6% for the empirical model, but it rose to as high as 13% with the diffusion approximation model. These results were not surprising because the fiber-optic probe in this study had a source-detector separation of only about 660 μm. Using the scattering coefficients $\mu_s$ from FIGS. 1A and 1B and a value of 0.9 for the tissue anisotropy g, it can be shown that the source-detector separation of the probe was often smaller than $1/\mu_s(1-g)$. This condition causes the diffusion approximation to break down [30], but the empirical model is accurate in this regime. R. Reif, et al., "Analytical model of light reflectance for extraction of the optical properties in small volumes of turbid media," Appl. Opt. 46, 7317-7328 (2007).

5.4 Potential of Optical Spectroscopy to Fulfill Unmet Clinical Need

Current methods to detect pancreatic adenocarcinoma are highly invasive and fail to find the disease early or to distinguish it from inflammation (pancreatitis). Hence, there is great biomedical need for an endoscopic screening procedure for early detection of pancreatic adenocarcinoma. Bimodal reflectance and fluorescence spectroscopy is a potential inroad into addressing this unmet clinical need. In this study, mathematical models of measured reflectance and fluorescence spectra were employed to quantitatively describe differences between normal pancreatic tissue, pancreatic adenocarcinoma, and pancreatitis. By using biomedically relevant parameters, the model provided a link between the results of optical spectroscopy and histology. Features in the reflectance spectra were quantitatively linked to larger cell nuclei in cancer and increased collagen content in both cancer and pancreatitis. The intrinsic fluorescence spectra were fit to a linear combination of collagen, NADH, and FAD basis spectra to show quantitative differences in the contribution of collagen to the measured fluorescence from normal pancreatic tissue, pancreatic adenocarcinoma, and pancreatitis.

Translation to an in vivo setting is feasible because the model can extract the optical absorption coefficient from increased blood content in the tissues. Challenges associated with obtaining an accurate reflectance fit near 425 and 550 nm (where hemoglobin absorption is noticeable) can be resolved by fitting each individual reflectance spectrum to an empirical equation, a photon migration model, or the $P_3$ approximation. M. Muller, et al., "Intrinsic fluorescence spectroscopy in turbid media: disentangling effects of scattering and absorption," Appl. Opt. 40, 4633-4646 (2001); G. M. Palmer and N. Ramanujam, "Monte-Carlo-based model for the extraction of intrinsic fluorescence from turbid media," J. Biomed. Opt. 13, 024017 (2008); J. C. Finlay and T. H. Foster, "Hemoglobin oxygen saturations in phantoms and in vivo from measurements of steady-state diffuse reflectance at a single, short source-detector separation," Med. Phys. 31, 1949-1959 (2004). Another test of the model could involve comparing the intrinsic fluorescence extracted via a Beer-Lambert factor (Eq. (6)) with that obtained with a more detailed photon migration model.

5.5 Illustration 1 Conclusions

The mathematical models of reflectance and fluorescence as discussed herein are useful tools for pancreatic cancer diagnostics because of their ability to quantitatively link the experimental results of optical spectroscopy with those of histopathology. The mathematical model of reflectance is able to quantitatively describe the reflectance spectra of normal pancreatic tissue, pancreatitis, and pancreatic adenocarcinoma in terms of biomedically relevant parameters. The algorithm to model the reflectance was rapid, taking only several seconds to execute. Furthermore, the concept of scaling an average measured normal pancreatic tissue reflectance spectrum to obtain the pancreatitis and adenocarcinoma spectra was found to be helpful with data interpretation due to its intuitive nature. FIGS. 2A and 2B show, among other things, the capability of the reflectance model to extract absorption and scattering coefficients of the aforementioned human pancreatic tissue types. When the fluorescence was corrected for attenuation artifacts (as shown in FIGS. 3A, 3B and 3C), the resulting intrinsic fluorescence spectra revealed differences in collagen content that correlated with histology as shown in Table 2. The, rapid, intuitive, and biomedically relevant nature of these mathematical models suggests that the data analysis procedure outlined herein may be of potential use not only for pancreatic cancer detection, but also for other optical diagnostic applications involving a wider range of biological tissues.

Illustration II

1. Introduction

In other embodiments, four tissue classification algorithms were developed to employ reflectance and fluorescence spectroscopy for differentiating between human pancreatic adenocarcinoma and pancreatitis tissue.

The first approach employed the ratio of measured reflectance at 470 nm to that at 650 nm and wavelength integrated fluorescence intensity (i.e., area under the curve) for tissue classification (i.e., SpARC—Spectral areas and ratios classifier) using Linear Discriminant Analysis (LDA), among other things.

The second was a chemometric approach that employed Principal Component Analysis (PCA) and Linear Discriminant analysis (LDA). In some embodiments, PCA was used to identify the diagnostic features in the spectra and then LDA was employed to classify the data based on these features.

The third method employed a photon-tissue interaction (PTI) model of photon transport in pancreatic tissue, previously developed by the inventors. R. H. Wilson, M. Chandra, J. Scheiman, D. Simeone, B. McKenna, J. Purdy, and M. A. Mycek, "Optical spectroscopy detects histological hallmarks of pancreatic cancer," Opt. Express 17, 17502-17516 (2009). The PTI model has been shown to be a relatively accurate means of quantitatively describing key changes in the reflectance and fluorescence spectra of adenocarcinoma and pancreatitis (relative to normal pancreatic tissue). In some embodiments, the quantitative parameters extracted from the model were used to classify tissue using LDA.

The fourth approach was a hybrid model that employed a combination of the chemometric, PTI model and SpARC algorithms.

For purposes of illustrating embodiments of the invention, further exemplary systems and methods of the invention are discussed herein below.

2. Methods

2.1 Human Studies

Reflectance and fluorescence spectra were measured from freshly excised pancreatic tissue obtained during Whipple procedures. Multiple sites were measured on tissues obtained from 12 patients within 30 minutes of excision. A total of 90 sites were measured from all the patients and two measurements were made on each site. After data acquisition from each measurement site, a portion of tissue was removed to link optical measurements with histological analysis.

2.2 Instrumentation

As in the prior example, a clinically compatible, fiber-optic coupled Reflectance and Fluorescence Lifetime Spectrometer (RFLS) was employed for data acquisition. M. Chandra, et al., "Probing pancreatic disease using tissue optical spectroscopy," J Biomed Opt 12, 060501 (2007); M. Chandra, et al., "Quantitative molecular sensing in biological tissues: an approach to non-invasive optical characterization," Optics Express 14, 6157-6171 (2006).

Figures 5, 6:
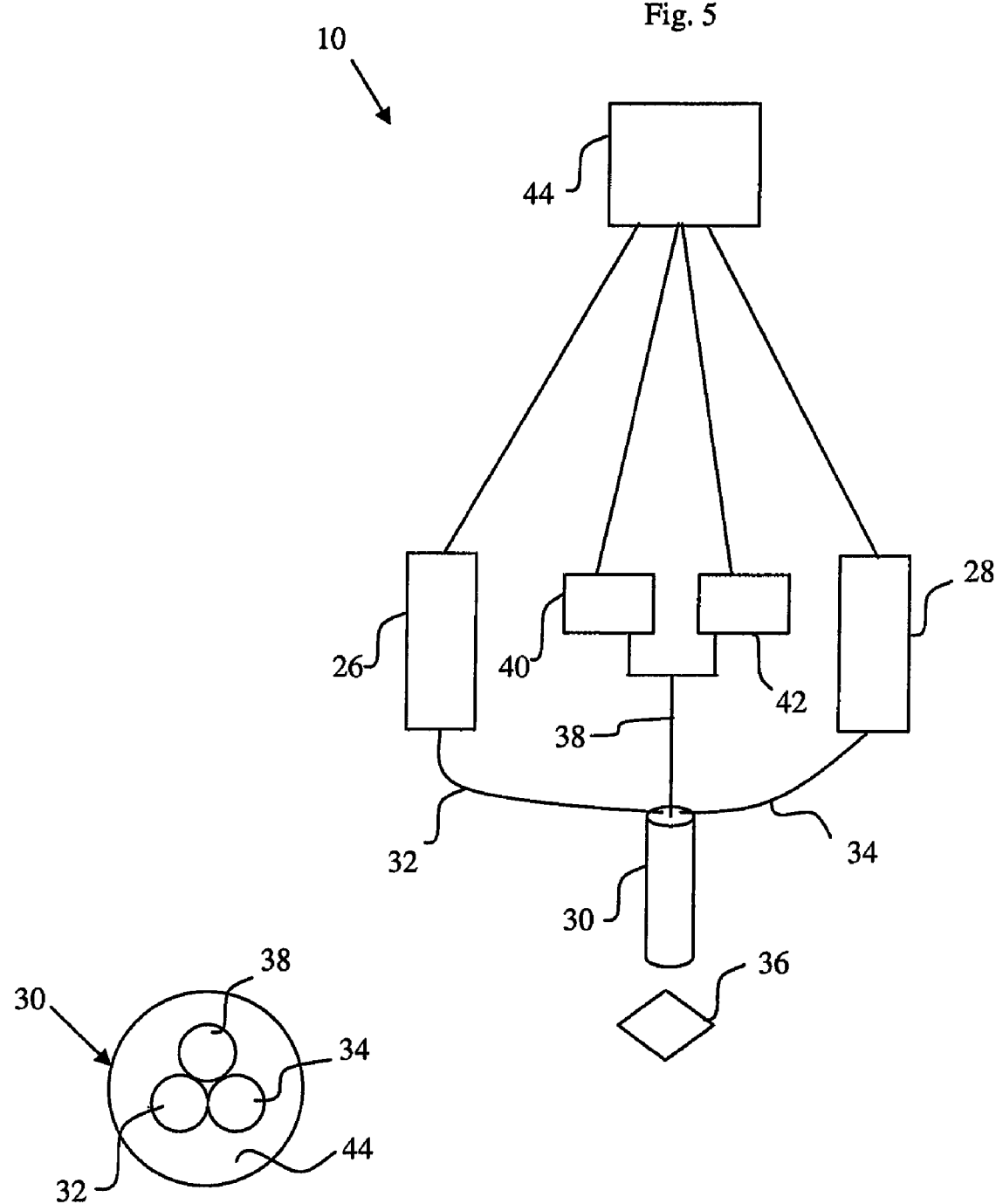
FIG. 5 is a schematic diagram of a system constructed in accordance with some embodiments of the invention.
FIG. 6 is a cross sectional view of optical fibers at the distal end of an exemplary probe used with a system constructed in accordance with some embodiments of the invention.

FIG. 5 provides a schematic of a system 10 constructed in accordance with some embodiments of the invention. It should be understood that system 10 components may be separate and in wired or wireless communication with one another. Alternatively, all or most of the components of system 10 may be combined as one instrument. System 10 includes a fluorescence excitation source 26 and a reflectance source 28 which are optically coupled with a probe 30 via independent fibers 32 and 34, respectively, for the communication of light therein. Fluorescence excitation source 26 may be, for example, a pulsed solid state diode laser emitting at 355 nm (e.g., PNV001525-140, JDS Uniphase, San Jose, Calif.) or like device, and reflectance source 28 may be, for example, a tungsten halogen lamp (e.g., HL 2000FHSA, Ocean Optics, Dunedin, Fla.), with a range of 360-2000 nm emission, or like device. Light delivered by fibers 32 and 34 is directed by probe 30 onto tissue 36 to produce one or more measurable spectroscopic responses, which in this embodiment includes reflectance and/or emitted fluorescence photons. Reflectance and emitted fluorescence photons from tissue 36 are delivered via a third fiber 38 disposed in probe 30 and in communication with one or more devices configured for measuring the spectroscopic response. In this embodiment, fiber 38 is in communication with a spectrograph 40 (e.g., MS 125, Oriel Instruments, Stratford, Conn.) or like device for measuring the properties of light and an avalanche photodiode 42 or other photodetector capable of time-resolved spectroscopic measurements, such as time-resolved fluorescence decay. As shown in FIG. 5, fiber 38 is divided so that a first portion of the detected photons is directed to spectrograph 40 and a second portion is directed to avalanche diode 42. In some embodiments, the division of fiber 38 is facilitated by a splitter or filter, such as a neutral density filter.

Spectrograph 40 may also include or be coupled with an intensified charge coupled device (ICCD) camera (e.g., ICCD 2063, Andor Technology, Belfast, Northern Ireland) or like device. Fibers 32, 34 and 36 may comprise 600 μm core optical fibers, although other sized fibers may be used. Alternatively, another material capable of delivering light as described above may be employed. System 10 further includes a data processing system 44 for analyzing the spectral data in accordance with the methods of the invention. For example, the data processing system 44 may be configured to compare the spectral data with the preset criteria, determine whether any preset criteria relating to a condition of tissue 36 is satisfied based on the spectral data, and classify tissue 36 accordingly based on the preset criteria satisfied. Data processing system 44 may also include a display for presenting the results of the analysis, which may be particularly useful when using system 10 during a biopsy or endoscopic procedure.

FIG. 6 illustrates an embodiment of probe 30 according the invention in which fibers 32, 34 and 36 are disposed adjacently in a substantially triangular cross sectional arrangement at distal end 44 of probe 30. It should be readily apparent that more or less fibers in a variety of arrangements may be employed in probe 30. For example, one fiber may be used or a ring of four or more fibers maybe fitted in probe 30. In operation, fluorescence and reflectance excitation of tissue 36 and measurements can be obtained using probe 30 by sequentially blocking light from fiber 32 and 34 using shutters (not shown) or some other apparatus for alternatively covering one fiber at a time while leaving fiber 36 exposed for the detection of tissue fluorescence and reflectance.

Those skilled in the art will readily appreciate that methods and systems of the embodiments of the invention, such as system 10, may include various other elements, such as electrical or optical components, lasers, lamps, oscilloscopes, connectors, connector blocks, relays, pulse conditioners, generators, etc., computer and network related software and hardware, such as programs, operating systems, memory storage devices, input/output devices, processors, servers, data communication links, whether wireless or otherwise, and data transceiving devices. Those skilled in the art will further appreciate that it is within the scope of the invention to include such additional elements and identifying precise types of components is not vital to the full implementation of the systems and methods of the invention.

The acquired fluorescence spectra were corrected for spectral instrument response after background correction. The reflectance spectra were also background subtracted and then scaled by the lamp reflectance spectrum ($R_o$) to obtain the corrected reflectance spectra ($R/R_o$). All spectra were normalized by scaling the peak intensity value to unity.

2.3 Pathology and Inclusion Criterion

Pathology indicated that of the measured sites 17 were adenocarcinoma sites, 22 were pancreatitis sites, and 11 were normal tissue sites. The rest of the sites were either malignant breast cancer that had metastasized to the pancreas (10 sites), intraductal papillary mucinous neoplasm (IPMN—8 sites), pancreatic intraepithelial neoplasia (PanIN—6 sites), serous cyst adenoma (SCA—8 sites), scar or fat tissue or both (5 sites) or a hybrid tissue site having two or more of the above mentioned pathologies (3 sites). These sites were excluded from the data set used for algorithm development. Furthermore, those measurements that were very noisy were also excluded from the data set (4 measurements).

This left a total of 33 adenocarcinoma measurements, 40 pancreatitis measurements, and 22 normal measurements of both fluorescence and reflectance spectra. Tissue algorithm development was undertaken with this set of data of 95 total spectra (Set 1) of both fluorescence and reflectance spectra.

A second set (Set 2) of data was analyzed separately in which six of the pancreatitis sites from patient 10 were also excluded owing to some discrepancy with pathology results. Thus Set 2 comprised of 33 adenocarcinoma measurements, 31 pancreatitis measurements, and 22 normal measurements (86 total spectra) of both fluorescence and reflectance spectra each.

Table 4 shown below indicates the pathology of the measured sites for each patient. The sites with asterisks were included in algorithm development as indicated below while sites without asterisks were excluded.

TABLE 4

Patient-wise histology of the sites from which data was collected

| Patient | N | P | A | PanIN | IPMN | SCA | MBC | Scar/fat/both | P and A[a] | N and A[b] |
|---|---|---|---|---|---|---|---|---|---|---|
| 1 | 2* | 3* | — | — | — | — | — | — | — | — |
| 2 | — | — | 5* | — | — | — | — | — | — | — |
| 3 | — | 5* | — | 1 | — | — | — | 1 | 1 | — |
| 4 | — | 3* | — | — | 1 | — | — | 1 | — | — |
| 5 | — | — | — | — | — | 8 | — | — | — | — |
| 6 | 4* | — | — | 1 | — | — | — | — | — | — |
| 7 | — | — | — | — | 7 | — | — | 1 | — | — |
| 8 | — | 4* | 1* | 1 | — | — | — | — | 1 | 1 |
| 9 | 5* | 1* | 1* | 3 | — | — | — | — | — | — |
| 10 | — | 6** | — | — | — | — | — | 2 | — | — |
| 11 | — | — | 10* | — | — | — | — | — | — | — |
| 12 | — | — | — | — | — | — | 10 | — | — | — |

N: Normal; P: Pancreatitis; A: Adenocarcinoma; PanIN: Pancreatic Intraepithelial Neoplasia; SCA: Serous Cyst Adenoma; MBC: metastatic breast carcinoma case
[a] A hybrid tissue site of chronic pancreatitis and adenocarcinoma;
[b] A hybrid tissue site of focal adenocarcinoma at the edge of mostly normal tissue
*These sites were included in the data.
**These sites were both included and excluded from the data for algorithm development 2.4 Leave-one-out Cross-validation A leave-one-out cross-validation was undertaken to test the performance of each of the proposed tissue classification algorithms. For each algorithm, the data were divided into Training and Test data where each spectrum was considered as Test data one at a time, while the remaining spectra were treated as Training data. Thus, each algorithm was implemented 95 times for Set 1 and 86 times for Set 2. Data sensitivity, specificity, positive predictive value (PPV) and negative predictive value (NPV) were calculated.

2.5 Spectral Areas and Ratios Classifier (SpARC) Algorithm

Preliminary examination of the fluorescence and reflectance spectra from a pilot study conducted by us had suggested the use of the ratio of measured Reflectance at 470 nm to that at 650 nm ($R_{ratio}=R_{470}/R_{650}$) and the wavelength integrated fluorescence (area under the curve) as possible tissue classifiers.

The ratio $R_{ratio}=R_{470}/R_{650}$ was calculated for each measured reflectance spectrum and the wavelength integrated fluorescence ($F_{area}$) was calculated for each of the fluorescence spectra. The test data was classified in a two-step procedure where $R_{ratio}$ was first employed to identify adenocarcinoma using LDA on the training data. If the tissue was classified as not adenocarcinoma then $R_{ratio}$ and $F_{area}$ were both employed to classify the test data as either pancreatitis or normal using LDA. The process was repeated for each of the spectra in data Set 1 and data Set 2 (as discussed in the section above regarding "leave-one-out cross-validation").

For purposes of illustrating some embodiments of the invention, exemplary chemometric analysis of the spectra is discussed in further detail below.

2.6 Chemometric Analysis of the Spectra 2.6.1 Principal Component Analysis (PCA)

PCA was employed to express each spectrum as a linear combination of a set of orthogonal basis vectors (or components). A. D. Joshi, et al., "Improving PET receptor binding estimates from Logan plots using principal component analysis," J Cerebr Blood F Met 28, 852-865 (2008). Of these components, the key-features of the data are captured by only a few vectors with high eigenvalues while the vectors corresponding to lower eigenvalues represent noise in the data. However, not all the key features of the spectra are diagnostically relevant (i.e., enabling differentiation between the tissue types). By identifying the few diagnostically relevant components, the dimensionality of the problem is reduced. The diagnostically relevant components are identified by fitting the principal components to the spectra. The components whose coefficients showed greatest difference between tissue types were identified as diagnostically relevant.

The training data spectra $\bar{s}_i \in R^{n \times 1}$ (i=1 to m) for different tissue types were grouped together and arranged row-wise in a matrix $S \in R^{m \times n}$ as shown below:

$$S = \begin{bmatrix} \bar{s}_1^T \\ \bar{s}_2^T \\ \vdots \\ \bar{s}_m^T \end{bmatrix} = \begin{bmatrix} \bar{s}_1^T \\ \vdots \\ \bar{s}_p^T \\ \vdots \\ \bar{s}_{p+q}^T \\ \vdots \\ \bar{s}_{p+q+r}^T \end{bmatrix}, \quad (8)$$

where, p, q and r (p+q+r=m) are the number of spectra for adenocarcinoma, pancreatitis and normal tissue type respectively. Using PCA, the above shown n dimensional training set (corresponding to the n measured wavelengths) with m total spectra can be represented as a linear combination of n basis vectors as shown below:

$$S^T = CX, \quad (9)$$

where, $^T$ is the transpose operator, $C \in R^{m \times n}$ is the matrix of the n principal components, and X is a matrix of the fit coefficients.

$$X = \begin{bmatrix} x_{11} & x_{12} & \cdots & x_{1m} \\ x_{21} & \ddots & & \vdots \\ \vdots & & \ddots & \\ x_{n1} & \cdots & \cdots & x_{nm} \end{bmatrix}, \quad (10)$$

Where, an element $x_{ji}$ is the fit-coefficient of the $j^{th}$ component for the $i^{th}$ spectrum.

The principal component matrix C was obtained from S by employing the princomp function in MATLAB. The princomp function first calculates matrix $S_0$ by subtracting the column mean vector from each row of S. Then singular value decomposition is used to calculate the principal components as the eigenvectors of the sample covariance matrix $$\left(\frac{1}{m-1}S_0^T S_0\right).$$

The columns of X were estimated by fitting the principal components to the spectra using ordinary least squares. The estimated coefficients vectors for each spectrum (i.e. the columns of X) were then separated into three groups based on the tissue type. The principal components for which the coefficients were significantly different between the tissue types were determined based on pair-wise student's T-test ($p<0.05$). Six such t-tests were performed for the coefficients of each principal component j: The hypothesis tested was that the mean fit-coefficients were significantly different for the jth principal component of (1) Adenocarcinoma and the rest of the tissue types, (2) Normal and the rest of the tissue types, (3) Pancreatitis and the rest of the tissue types, (4) adenocarcinoma and Pancreatitis, (5) Adenocarcinoma and Normal, (6) Pancreatitis and Normal. These principal components were the diagnostically relevant components.

The above analysis was done for both fluorescence (n=492) and reflectance spectra (n=521) separately to determine the components whose coefficients would be used for classification of tissue types in the test data.

Thus, in some embodiments, the steps involved in the algorithm development include: obtaining fluorescence or reflectance spectra at n or a plurality of wavelengths; apply principal component analysis to calculate n or a plurality of components; T-test compares the fit coefficients of each of the n components for each tissue type, that is, tissue with adenocarcinoma, normal tissue or pancreatitis tissue and identifies which components are significant for classifying the tissue types.

2.6.2 Classification of Test Data Using PCA and LDA

Each fluorescence and reflectance spectrum of the test data were then fit to the principal components obtained above (C) and the coefficients of the components that were identified as being diagnostically relevant were used for classifying the test data by employing Linear discriminant analysis (LDA). Z. F. Ge, et al., "Identification of colonic dysplasia and neoplasia by diffuse reflectance spectroscopy and pattern recognition techniques," Applied Spectroscopy 52, 833-839 (1998). The analysis was done by employing the coefficients of a varying number of diagnostically relevant components.

This analysis was repeated for each measured spectrum for leave-one-out cross-validation as described above.

2.8 Hybrid Algorithm: Combination of the Chemometric, PTI Model, and SpARC Algorithms It has been previously shown that a "hybrid" between a pure chemometric model (e.g. PCA) and a physical tissue model can produce increased diagnostic accuracy. Z. Volynskaya, et al., "Diagnosing breast cancer using diffuse reflectance spectroscopy and intrinsic fluorescence spectroscopy," J Biomed Opt 13, 024012 (2008). A hybrid algorithm employing the parameters extracted from the SpARC algorithm, the chemometric approach, and the physical photon-tissue interaction (PTI) model, was used to classify tissue spectra. LDA was employed to this multi-dimensional classification criterion to achieve tissue classification using a leave-one-out cross-validation. The data was divided into Training and Test data using a leave-one-out method. The classifiers corresponding to SpARC, Chemometric and PTI model algorithms were calculated for each of the Training set data and the Test data.

The SpARC algorithm as discussed above was employed to calculate the ratio of reflectance intensities at 470 nm to that at 650 nm ($R_{ratio}=R_{470}/R_{650}$) for each reflectance spectrum and the wavelength integrated fluorescence intensity ($F_{area}$) for each fluorescence spectrum.

The Chemometric algorithm as discussed above was employed to identify the diagnostically relevant principal components (PC) of reflectance and fluorescence spectra in the training set for identifying adenocarcinoma from the rest ($RPC_A$ and $FPC_A$) and for identifying between pancreatitis and normal tissue ($RPC_{P-N}$ and $FPC_{P-N}$).

Once these parameters were extracted, Linear Discriminant Analysis was first employed to classify the Test data as either adenocarcinoma or not adenocarcinoma using all or a subset of L/Lo, $C_{coll}$, $C_{NADH}+C_{FAD}$, $R_{ratio}$, $F_{area}$, and fit-coefficients of $RPC_A$ and $FPC_A$.

Then, if the data was classified as not cancer, LDA employed all or a subset of L/Lo, $C_{coll}$, $C_{NADH}+C_{FAD}$, $R_{ratio}$, $F_{area}$, and fit-coefficients of $RPC_{P-N}$ and $FPC_{P-N}$ to classify the Test data as either pancreatitis or normal tissue type.

This process was repeated in a leave-one-out cross-validation scheme to calculate sensitivity, specificity, PPV and NPV.

2.9 Principal Component Analysis (PCA) of Time-resolved Fluorescence Data

PCA was employed as described above on the time-resolved fluorescence data acquired from adenocarcinoma, pancreatitis, and normal tissue. The acquired decay traces were smoothed and normalized and the principal components were calculated for the training data. The t-test on the fit-coefficients of each principal component indicated that pancreatitis and normal tissue can be discriminated by using the PCA of time-resolved data.

The analysis was done for distinguishing Pancreatitis from Normal tissue using a leave-one-out cross-validation on data Set 1 and data Set 2 excluding patient 11 data. Data from patient 1 to 10 were collected by measuring the entire spectrum. The data from patient 11 onwards was excluded as it was obtained with a long-pass filter (>500 nm) in front of the avalanche photodiode (thus capturing only a portion of the spectrum). The results are discussed herein below.

3. Results 3.1 SpARC Algorithm for Tissue Classification

Classification of data Set 1 and Set 2 was achieved by using either only $R_{ratio}$ as a classifier (Table 5, Table 6), or only $F_{area}$ as a classifier (Table 7, and Table 8) or a combination of the two (Table 9 and Table 10). The tables list the sensitivity, specificity, PPV, and NPV of the SpARC algorithm in classifying (a) adenocarcinoma from pancreatitis and normal tissue, (b) adenocarcinoma from pancreatitis tissue, (c) adenocarcinoma from normal tissue, (d) pancreatitis from normal tissue and adenocarcinoma tissue (e) normal from adenocarcinoma and pancreatitis tissue. The classification in Tables 9 and 10 was undertaken by first employing $R_{ratio}$ to identify adenocarcinoma and then employing $R_{ratio}$ and $F_{area}$ to distinguish between pancreatitis and normal tissue types. $F_{area}$ was not employed for adenocarcinoma classification as it decreased the classification performance of the algorithm.

TABLE 5

Employing only $R_{ratio}$ for data Set 1 classification

| Tissue Type | Sensitivity (%) | Specificity (%) | PPV (%) | NPV (%) |
|---|---|---|---|---|
| A vs. P and N | 84.8 | 85.5 | 75.7 | 91.4 |
| P vs. A and N | 35.0 | 87.3 | 66.7 | 64.9 |
| N vs. A and P | 81.8 | 74.0 | 48.6 | 93.1 |
| A vs. P | 84.8 | 85.0 | 82.4 | 87.2 |
| A vs. N | 87.9 | 95.5 | 96.7 | 84.0 |
| P vs. N | 57.5 | 81.8 | 85.2 | 51.4 |

N: Normal; P: Pancreatitis; A: Adenocarcinoma

TABLE 6

Employing only $R_{ratio}$ for data Set 2 classification

| Tissue Type | Sensitivity (%) | Specificity (%) | PPV (%) | NPV (%) |
|---|---|---|---|---|
| A vs. P and N | 87.9 | 88.7 | 82.9 | 92.2 |
| P vs. A and N | 35.5 | 87.3 | 61.1 | 70.6 |
| N vs. A and P | 72.7 | 73.4 | 48.5 | 88.7 |
| A vs. P | 84.8 | 83.9 | 84.8 | 83.9 |
| A vs. N | 87.9 | 95.5 | 96.7 | 84.0 |
| P vs. N | 51.6 | 72.7 | 72.7 | 51.6 |

N: Normal; P: Pancreatitis; A: Adenocarcinoma

TABLE 7

Employing only $F_{area}$ for data Set 1 classification

| Tissue Type | Sensitivity (%) | Specificity (%) | PPV (%) | NPV (%) |
|---|---|---|---|---|
| A vs. P and N | 66.7 | 62.9 | 48.9 | 78.0 |
| P vs. A and N | 57.5 | 69.1 | 57.5 | 69.1 |
| N vs. A and P | 18.2 | 91.8 | 40.0 | 78.8 |
| A vs. P | 66.7 | 62.5 | 59.5 | 69.4 |
| A vs. N | 51.5 | 59.1 | 65.4 | 44.8 |
| P vs. N | 57.5 | 63.6 | 74.2 | 45.2 |

N: Normal; P: Pancreatitis; A: Adenocarcinoma

TABLE 8

Employing only $F_{area}$ for data Set 2 classification

| Tissue Type | Sensitivity (%) | Specificity (%) | PPV (%) | NPV (%) |
|---|---|---|---|---|
| A vs. P and N | 66.7 | 60.4 | 51.2 | 74.4 |
| P vs. A and N | 54.8 | 67.3 | 48.6 | 72.5 |
| N vs. A and P | 13.6 | 92.2 | 37.5 | 75.6 |
| A vs. P | 66.7 | 58.1 | 62.9 | 62.1 |
| A vs. N | 51.5 | 59.1 | 65.4 | 44.8 |
| P vs. N | 54.8 | 59.1 | 65.4 | 48.1 |

N: Normal; P: Pancreatitis; A: Adenocarcinoma

TABLE 9

Performance of the SpARC algorithm for data Set 1

| Tissue Type | Sensitivity (%) | Specificity (%) | PPV (%) | NPV (%) |
|---|---|---|---|---|
| A vs. P and N | 84.8 | 85.5 | 75.7 | 91.4 |
| P vs. A and N | 50.0 | 83.6 | 69.0 | 69.7 |
| N vs. A and P | 72.7 | 82.2 | 55.2 | 90.9 |
| A vs. P | 84.8 | 85.0 | 82.4 | 87.2 |
| A vs. N | 87.9 | 95.5 | 96.7 | 84.0 |
| P vs. N | 70.0 | 72.7 | 82.4 | 57.1 |

N: Normal; P: Pancreatitis; A: Adenocarcinoma

TABLE 10

Performance of the SpARC algorithm for data Set 2

| Tissue Type | Sensitivity (%) | Specificity (%) | PPV (%) | NPV (%) |
|---|---|---|---|---|
| A vs. P and N | 87.9 | 88.7 | 82.9 | 92.2 |
| P vs. A and N | 51.6 | 87.3 | 69.6 | 76.2 |
| N vs. A and P | 72.7 | 81.3 | 57.1 | 89.7 |
| A vs. P | 84.8 | 83.9 | 84.8 | 83.9 |
| A vs. N | 87.9 | 95.5 | 96.7 | 84.0 |
| P vs. N | 64.5 | 72.7 | 76.9 | 59.3 |

N: Normal; P: Pancreatitis; A: Adenocarcinoma 3.2 Chemometric Classification

The t-tests performed as described above indicated that the principal components of the reflectance and fluorescence spectra that were diagnostically relevant for classifying Adenocarcinoma from Pancreatitis and Normal ($RPC_A$ and $FPC_A$) were not the same as for classifying Pancreatitis from Normal. This indicated that it may be necessary to separate the classification algorithm into a two-step process where first Adenocarcinoma sites are identified in the Test data and then the rest of the data is classified into Normal and Pancreatitis.

3.2.1 Classifying Adenocarcinoma vs. Pancreatitis and Normal Tissue

Four diagnostically relevant principal components, two each from reflectance and fluorescence were identified by finding those components, in the first ten principal components, for which the t-test between adenocarcinoma and the remaining tissue types' fit-coefficents gave a p-value<0.05. LDA was then used to classify the test data into adenocarcinoma or not adenocarcinoma based on the fit-coefficient values for all or a subset of these four principal component values ($RPC_A1$, $RPC_A2$, $FPC_A1$, $FPC_A2$).

If a tissue type was classified as not adenocarcinoma in this part of the algorithm then it was classified as either normal or pancreatitis as described below.

3.2.2 Classifying Pancreatitis vs. Normal Tissue

Four diagnostically relevant principal components, two each from reflectance and fluorescence were identified by finding those components, in the first ten principal components, for which the t-test between normal and pancreatitis fit-coefficents gave a p-value <0.05. LDA was then used to classify test data into normal and pancreatitis based on the fit-coefficient values for all or a subset of these four principal component values ($RPC_{P-N}1$, $RPC_{P-N}2$, $FPC_{P-N}1$, $FPC_{P-N}2$). The chemometric algorithm was validated by employing the leave-one-out technique.

Table 11 and Table 12 list the classification performance of the chemometric algorithm if only the fit-coefficients of diagnostically relevant reflectance principal components are employed for tissue classification ($RPC_A1$, $RPC_A2$, $RPC_{P-N}1$, $RPC_{P-N}2$).

Table 13 and Table 14 list the classification performance of the chemometric algorithm if only the fit-coefficients of diagnostically relevant principal components of the fluorescence spectra are employed for tissue classification ($FPC_A1$, $FPC_A2$, $FPC_{P\_}N1$, $FPC_{P\text{-}N}2$). In Table 14 values are missing due to the absence of any diagnostically relevant, $FPC_{P\text{-}N}1$, $FPC_{P\text{-}N}2$ for distinguishing between normal and pancreatitis for certain Test data. This shows that chemometric analysis of fluorescence spectra could not be used alone for tissue classification.

Table 15 and Table 16 list the classification performance of the chemometric algorithm if the fit-coefficients of all diagnostically relevant principal components of reflectance and fluorescence spectra are employed for tissue classification ($RPC_A1$, $RPC_A2$, $FPC_A1$, $FPC_A2$, $RPC_{P\text{-}N}1$, $RPC_{P\text{-}N}2$, $FPC_{P\text{-}N}1$, and $FPC_{P\text{-}N}2$).

TABLE 11

Performance of the chemometric algorithm using Reflectance spectra only for data Set 1 ($RPC_A1$, $RPC_A2$, $RPC_{P\text{-}N}1$, $RPC_{P\text{-}N}2$)

| Tissue Type | Sensitivity (%) | Specificity (%) | PPV (%) | NPV (%) |
| --- | --- | --- | --- | --- |
| A vs. P and N | 93.9 | 83.9 | 75.6 | 96.3 |
| P vs. A and N | 52.5 | 90.9 | 80.8 | 72.5 |
| N vs. A and P | 77.3 | 84.9 | 60.7 | 92.5 |
| A vs. P | 90.9 | 77.5 | 76.9 | 91.2 |
| A vs. N | 93.9 | 86.4 | 91.2 | 90.5 |
| P vs. N | 70.0 | 77.3 | 84.8 | 58.6 |

N: Normal; P: Pancreatitis; A: Adenocarcinoma

TABLE 12

Performance of the chemometric algorithm using Reflectance spectra only for data Set 2 ($RPC_A1$, $RPC_A2$, $RPC_{P\text{-}N}1$, $RPC_{P\text{-}N}2$)

| Tissue Type | Sensitivity (%) | Specificity (%) | PPV (%) | NPV (%) |
| --- | --- | --- | --- | --- |
| A vs. P and N | 87.9 | 86.8 | 80.6 | 92.0 |
| P vs. A and N | 54.8 | 87.3 | 70.8 | 77.4 |
| N vs. A and P | 68.2 | 82.8 | 57.7 | 88.3 |
| A vs. P | 87.9 | 80.6 | 82.9 | 86.2 |
| A vs. N | 93.9 | 86.4 | 91.2 | 90.5 |
| P vs. N | 74.2 | 68.2 | 76.7 | 65.2 |

N: Normal; P: Pancreatitis; A: Adenocarcinoma

TABLE 13

Performance of the chemometric algorithm using Fluorescence spectra only for data Set 1 ($FPC_A1$, $FPC_A2$, $FPC_{P\text{-}N}1$, $FPC_{P\text{-}N}2$)

| Tissue Type | Sensitivity (%) | Specificity (%) | PPV (%) | NPV (%) |
| --- | --- | --- | --- | --- |
| A vs. P and N | 78.8 | 82.3 | 70.3 | 87.9 |
| P vs. A and N | 32.5 | 78.2 | 52.0 | 61.4 |
| N vs. A and P | 50.0 | 69.9 | 33.3 | 82.3 |
| A vs. P | 78.8 | 80.0 | 76.5 | 82.1 |
| A vs. N | 81.8 | 81.8 | 87.1 | 75.0 |
| P vs. N | 42.5 | 54.5 | 63.0 | 34.3 |

N: Normal; P: Pancreatitis; A: Adenocarcinoma

TABLE 14

Performance of the chemometric algorithm using Fluorescence spectra only for data Set 2 ($FPC_A1$, $FPC_A2$, $FPC_{P\text{-}N}1$, $FPC_{P\text{-}N}2$)

| Tissue Type | Sensitivity (%) | Specificity (%) | PPV (%) | NPV (%) |
| --- | --- | --- | --- | --- |
| A vs. P and N | 69.7 | 81.1 | 69.7 | 81.1 |
| P vs. A and N | * | * | * | * |
| N vs. A and P | * | * | * | * |
| A vs. P | 69.7 | 77.4 | 76.7 | 70.6 |
| A vs. N | 72.7 | 77.3 | 82.8 | 65.4 |
| P vs. N | * | * | * | * |

N: Normal; P: Pancreatitis; A: Adenocarcinoma;
* No significant PC for classification

TABLE 15

Performance of the chemometric algorithm for data Set 1 Employing $RPC_A1$, $RPC_A2$, $FPC_A1$, $FPC_A2$, $RPC_{P\text{-}N}1$, $RPC_{P\text{-}N}2$, $FPC_{P\text{-}N}1$, and $FPC_{P\text{-}N}2$

| Tissue Type | Sensitivity (%) | Specificity (%) | PPV (%) | NPV (%) |
| --- | --- | --- | --- | --- |
| A vs. P and N | 90.9 | 83.9 | 75.0 | 94.5 |
| P vs. A and N | 52.5 | 87.3 | 75.0 | 71.6 |
| N vs. A and P | 63.6 | 82.2 | 51.9 | 88.2 |
| A vs. P | 87.9 | 82.5 | 80.6 | 89.2 |
| A vs. N | 93.9 | 85.7 | 91.2 | 90.0 |
| P vs. N | 67.5 | 63.6 | 77.1 | 51.9 |

N: Normal; P: Pancreatitis; A: Adenocarcinoma

TABLE 16

Performance of the chemometric algorithm for data Set 2 Employing $RPC_A1$, $RPC_A2$, $FPC_A1$, $FPC_A2$, $RPC_{P\text{-}N}1$, $RPC_{P\text{-}N}2$, $FPC_{P\text{-}N}1$, and $FPC_{P\text{-}N}2$

| Tissue Type | Sensitivity (%) | Specificity (%) | PPV (%) | NPV (%) |
| --- | --- | --- | --- | --- |
| A vs. P and N | 87.9 | 88.7 | 82.9 | 92.2 |
| P vs. A and N | 58.1 | 85.5 | 69.2 | 78.3 |
| N vs. A and P | 63.6 | 82.8 | 56.0 | 86.9 |
| A vs. P | 87.9 | 87.1 | 87.9 | 87.1 |
| A vs. N | 93.9 | 86.4 | 91.2 | 90.5 |
| P vs. N | 71.0 | 63.6 | 73.3 | 60.9 |

N: Normal; P: Pancreatitis; A: Adenocarcinoma

Table 17 and Table 18 list the classification performance of the chemometric algorithm if the fit-coefficients of the following diagnostically relevant principal components of reflectance and fluorescence spectra are employed for tissue classification ($RPC_A1$, $RPC_A2$, $FPC_A1$, $RPC_{P\text{-}N}1$, $RPC_{P\text{-}N}2$, $FPC_{P\text{-}N}1$, and $FPC_{P\text{-}N}2$) i.e. $FPC_A2$ was not employed for adenocarcinoma classification. This algorithm showed the best adenocarcinoma classification.

TABLE 17

Performance of the chemometric algorithm for data Set 1 Employing $RPC_A1$, $RPC_A2$, $FPC_A1$, $RPC_{P\text{-}N}1$, $RPC_{P\text{-}N}2$, $FPC_{P\text{-}N}1$, and $FPC_{P\text{-}N}2$

| Tissue Type | Sensitivity (%) | Specificity (%) | PPV (%) | NPV (%) |
| --- | --- | --- | --- | --- |
| A vs. P and N | 93.9 | 85.5 | 77.5 | 96.4 |
| P vs. A and N | 52.5 | 85.5 | 72.4 | 71.2 |
| N vs. A and P | 63.6 | 83.6 | 53.8 | 88.4 |

TABLE 17-continued

Performance of the chemometric algorithm for data Set 1 Employing $RPC_A1$, $RPC_A2$, $FPC_A1$, $RPC_{P-N}1$, $RPC_{P-N}2$, $FPC_{P-N}1$, and $FPC_{P-N}2$

| Tissue Type | Sensitivity (%) | Specificity (%) | PPV (%) | NPV (%) |
|---|---|---|---|---|
| A vs. P | 93.9 | 80.0 | 79.5 | 94.1 |
| A vs. N | 93.9 | 86.4 | 91.2 | 90.5 |
| P vs. N | 67.5 | 63.6 | 77.1 | 51.9 |

N: Normal; P: Pancreatitis; A: Adenocarcinoma

TABLE 18

Performance of the chemometric algorithm for data Set 2 Employing $RPC_A1$, $RPC_A2$, $FPC_A1$, $RPC_{P-N}1$, $RPC_{P-N}2$, $FPC_{P-N}1$, and $FPC_{P-N}2$

| Tissue Type | Sensitivity (%) | Specificity (%) | PPV (%) | NPV (%) |
|---|---|---|---|---|
| A vs. P and N | 93.9 | 88.7 | 83.8 | 95.9 |
| P vs. A and N | 54.8 | 87.3 | 70.8 | 77.4 |
| N vs. A and P | 63.6 | 82.8 | 56.0 | 86.9 |
| A vs. P | 90.9 | 87.1 | 88.2 | 90.0 |
| A vs. N | 93.9 | 86.4 | 91.2 | 90.5 |
| P vs. N | 71.0 | 63.6 | 73.3 | 60.9 |

N: Normal; P: Pancreatitis; A: Adenocarcinoma

3.4 Hybrid Algorithm for Tissue Classification: Combination of Chemometric, PTI Model and SpARC Algorithms The Hybrid algorithm was also a two-step algorithm that first identified a Test data as adenocarcinoma or not. If not, the data was then classified as either pancreatitis or normal.

Figure 7:
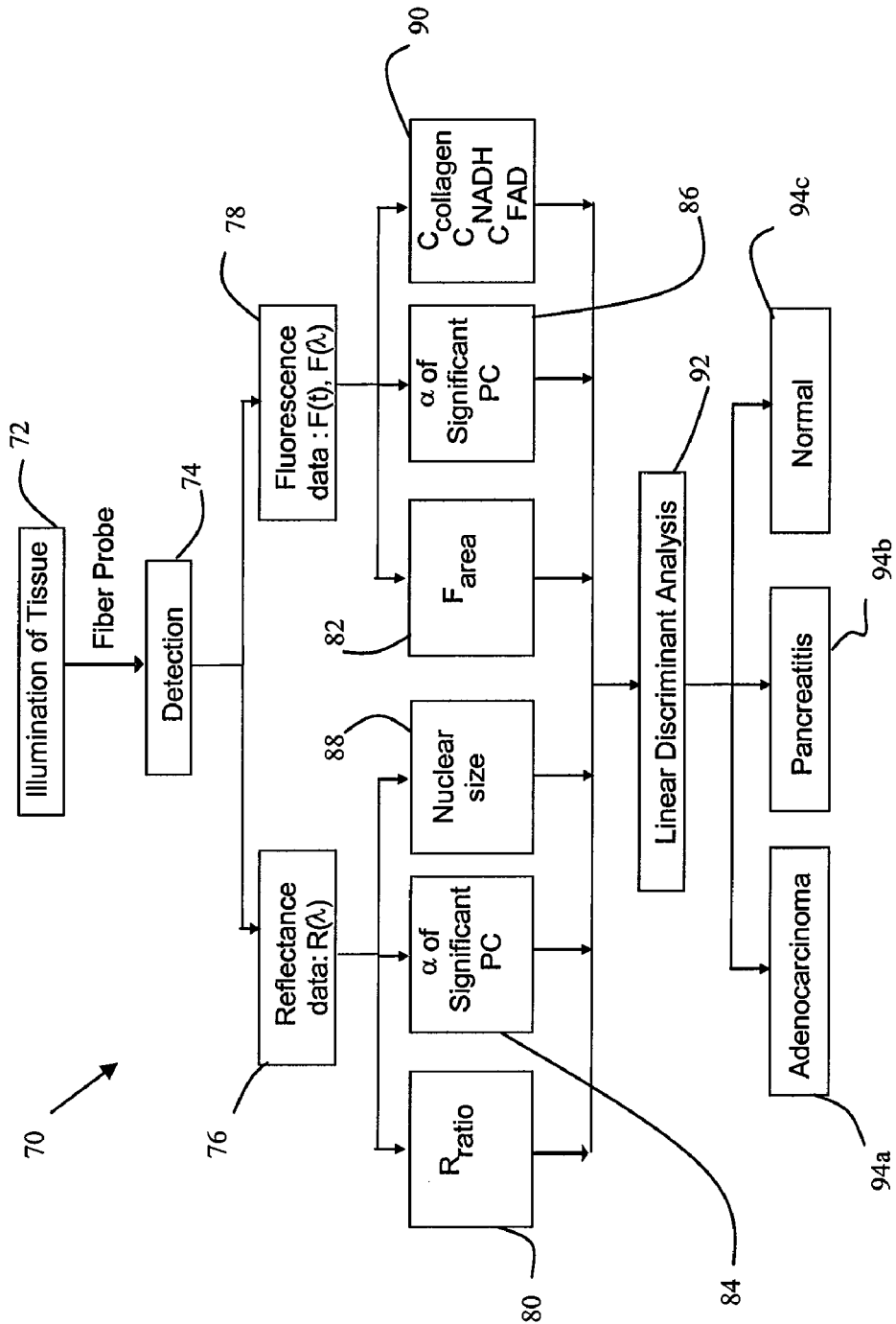
FIG. 7 is a flow chart illustrating the manner in which the hybrid algorithm may be employed in some embodiments to classify a pancreatic tissue site into normal, adenocarcinoma, or pancreatitis.

FIG. 7 provides a flow chart 70 which illustrates, among other things, an example of the manner in which the hybrid algorithm can be employed to classify a pancreatic tissue site into normal, adenocarcinoma, or pancreatitis. In this example, a fiber optic probe, such as the probe discussed previously, delivers excitation light from the fluorescence and reflectance sources to the tissue site to produce a spectroscopic event. The fluorescence and reflectance signals, that is, the emitted reflectance spectrum (R(λ)), fluorescence spectrum (F(λ)), and time-resolved fluorescence decay (F(t)), are then collected by the probe and delivered to the detectors. The SpARC algorithm is employed to calculate the $R_{ratio}(=R_{470}/R_{650})$ for the reflectance spectrum and the wavelength integrated fluorescence intensity ($F_{area}$) for the fluorescence spectrum. The Chemometric algorithm is then employed to calculate the fit-coefficients (α) for the diagnostically significant principal components (PC) of the reflectance and fluorescence spectra and time-resolved fluorescence decay. It should be noted that for each set of measurements of reflectance and fluorescence spectra, the PTI model algorithm extracted the parameters nuclear size(L/Lo), $C_{coll}$, $C_{NADH}$, and $C_{FAD}$. Linear Discriminant Analysis (LDA) is then employed to this multi-dimensional classification criterion to achieve tissue classification using a leave-one-out cross-validation.

Table 25 and Table 26 list the sensitivity, specificity, PPV, and NPV of the Hybrid algorithm in classifying pancreatic tissue (for data Set 1 and Set2). In this case all the classifiers from SpARC($R_{ratio}$ and $F_{area}$) and Chemometric ($RPC_A1$, $RPC_A2$, $FPC_A1$, $FPC_A2$, $RPC_{P-N}1$, $RPC_{P-N}2$, $FPC_{P-N}1$, and $FPC_{P-N}2$), and PTI model (L/Lo, $C_{coll}$, $C_{NADH}$+$C_{FAD}$) algorithms were employed for tissue classification. However, a sub-set of these classifiers could also be used.

TABLE 25

Performance of the Hybrid algorithm for data Set 1 All classifiers from Chemometric, PTI model and SpARC algorithm included

| Tissue Type | Sensitivity (%) | Specificity (%) | PPV (%) | NPV (%) |
|---|---|---|---|---|
| A vs. P and N | 84.8 | 95.2 | 90.3 | 92.2 |
| P vs. A and N | 65.0 | 85.5 | 76.5 | 77.0 |
| N vs. A and P | 72.7 | 80.8 | 53.3 | 90.8 |
| A vs. P | 84.8 | 92.5 | 90.3 | 88.1 |
| A vs. N | 90.9 | 86.4 | 90.9 | 86.4 |
| N vs. P | 72.5 | 72.7 | 82.9 | 59.3 |

N: Normal; P: Pancreatitis; A: Adenocarcinoma

TABLE 26

Performance of the Hybrid algorithm for data Set 2 All classifiers from Chemometric, PTI model and SpARC algorithm included

| Tissue Type | Sensitivity (%) | Specificity (%) | PPV (%) | NPV (%) |
|---|---|---|---|---|
| A vs. P and N | 87.9 | 92.5 | 87.9 | 92.5 |
| P vs. A and N | 48.4 | 87.3 | 68.2 | 75.0 |
| N vs. A and P | 68.2 | 75.0 | 48.4 | 87.3 |
| A vs. P | 84.8 | 87.1 | 87.5 | 84.4 |
| A vs. N | 87.9 | 81.8 | 87.9 | 81.8 |
| N vs. P | 58.1 | 68.2 | 72.0 | 53.6 |

N: Normal; P: Pancreatitis; A: Adenocarcinoma

Figure 4A:
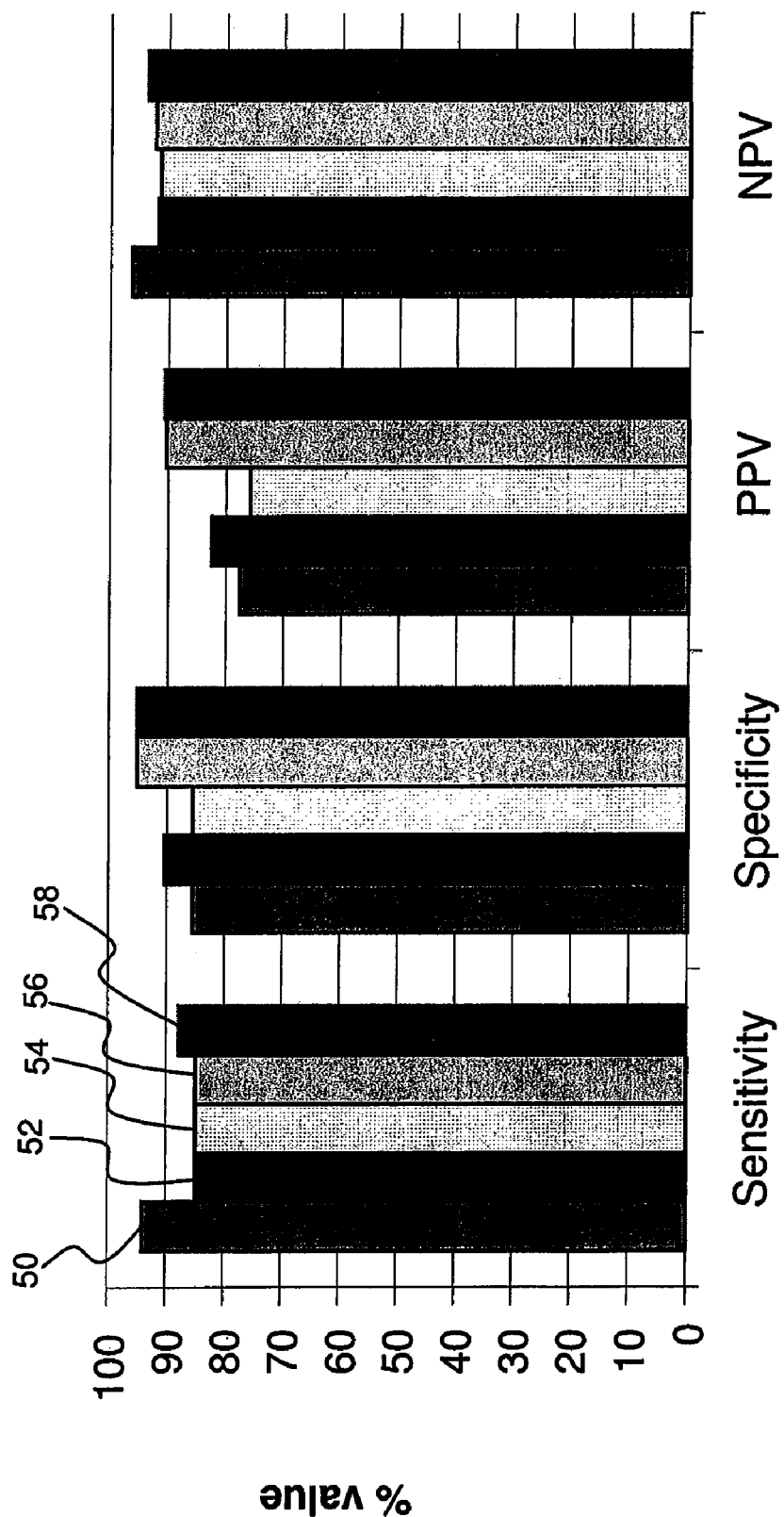
FIGS. 4A and 4B provide bar graphs illustrating the performance of the various modeling methods employed by some embodiments of the invention, namely, chemometric, PTI model, SpARC, and hybrid tissue classification algorithms in identifying adenocarcinoma tissue.
Figure 4B:
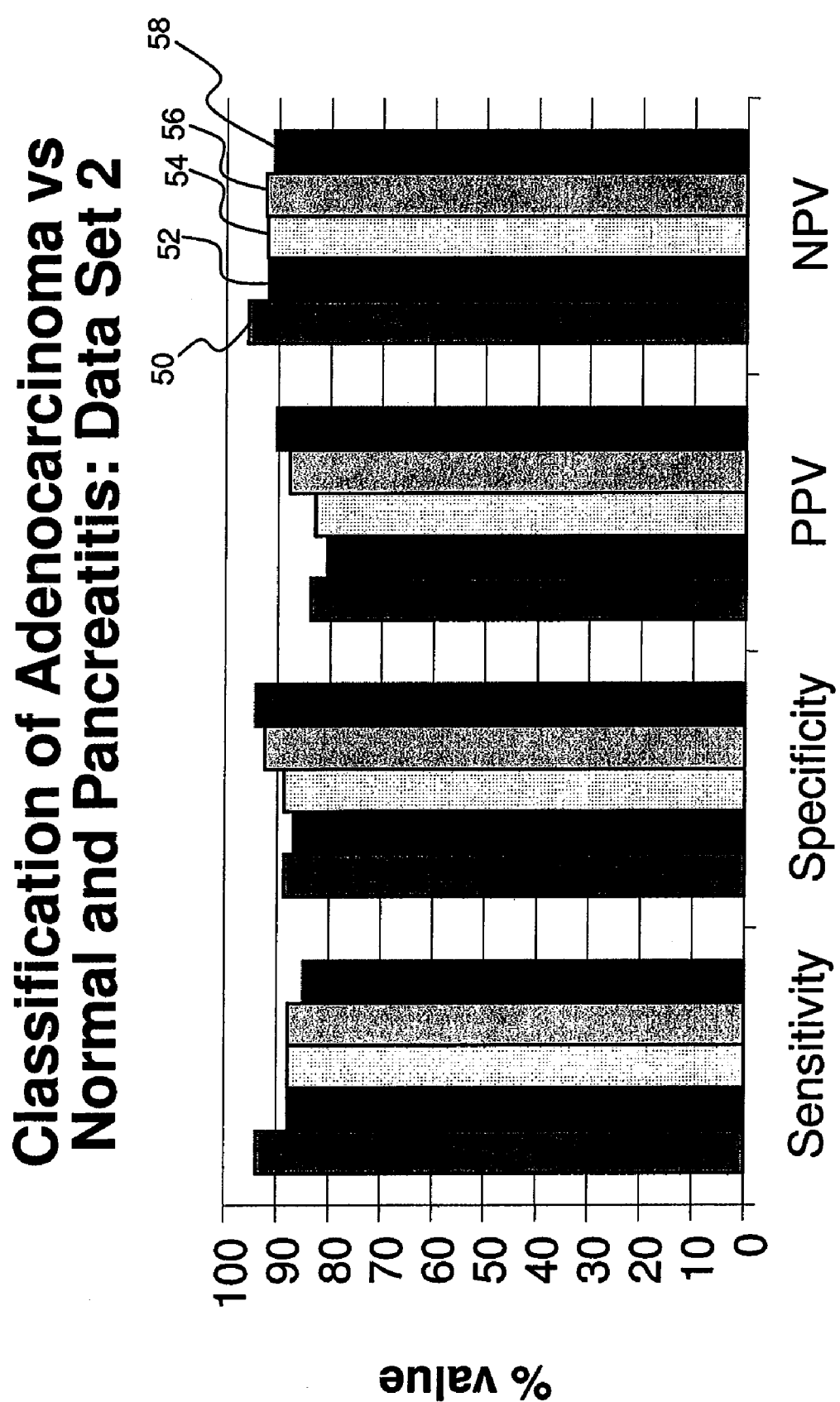

The bar plots in FIGS. 4A and 4B summarize the performance of each of the developed algorithms in identifying adenocarcinoma tissue for data Set 1 and Set 2. The chemometric algorithm represented here as the first column 50 of each grouping of columns employed $RPC_A1$, $RPC_A2$, $FPC_A1$, $RPC_{P-N}1$, $RPC_{P-N}2$, $FPC_{P-N}1$, and $FPC_{P-N}2$ for classification (as shown in Table 17 and Table 18). The PTI model algorithm represented as the second column 52 of each grouping employed L/Lo, $C_{coll}$, and $C_{NADH}$+$C_{FAD}$ for classification (Table 23 and Table 24). The SpARC algorithm represented as the third column 54 of each grouping employed $R_{ratio}$ for adenocarcinoma identification and $R_{ratio}$ and $F_{area}$ for classification of Test data as either pancreatitis or normal tissue (see Table 9 and Table 10). The hybrid algorithm is represented as the fourth column 56 of each grouping of columns. The performance of a second hybrid algorithm employing only a subset of the classifiers is also shown as the fifth column 58 of each grouping. In this case only $R_{ratio}$, $RPC_A1$, $RPC_A2$, $FPC_A1$, L/Lo, $C_{coll}$, and $C_{NADH}$+$C_{FAD}$ were employed for adenocarcinoma classification. For classification of the Test data as either pancreatitis or normal all the classifiers were employed ($R_{ratio}$, $F_{area}$, $RPC_{P-N}1$, $RPC_{P-N}2$, $FPC_{P-N}1$, $FPC_{P-N}2$, L/Lo, $C_{coll}$, and $C_{NADH}$+$C_{FAD}$). The plot shows that a combination of the developed algorithms shows the most promise for pancreatic tissue classification.

3.5 Classifying Pancreatitis vs. Normal Tissue Using PCA and LDA on Time-resolved Fluorescence Data The fit-coefficients of the $1^{st}$ and $7^{th}$ principal components were identified as diagnostically relevant for classifying pancreatitis and normal tissue. LDA was then employed to classify test data into normal and pancreatitis based on these fit-coefficient values for these diagnostically relevant principal component values.

The chemometric algorithm was validated by employing the leave-one-out technique as described above. Table 27 lists sensitivity, specificity, PPV, and NPV of the chemometric algorithm in classifying pancreatitis from normal tissue using time-resolved fluorescence data (Set 1 and Set 2). This algorithm appears to have performed the best amongst the developed algorithm for classifying between normal and pancreatitis tissue but may need further study and/or refinement.

TABLE 27

Performance of the time-resolved fluorescence data chemometric algorithm in classifying pancreatitis and normal tissue

| Data Set* | Sensitivity (%) | Specificity (%) | PPV (%) | NPV (%) |
|---|---|---|---|---|
| Set 1 | 75.0 | 81.8 | 88.2 | 64.3 |
| Set 2 | 71.0 | 81.8 | 84.6 | 66.7 |

*Patient 11 data from both data set 1 and data set 2 were excluded due to difference in data acquisition parameters Time-resolved data will be collected with a long-pass filter (>500 nm) in front of the detector (patient 11 onwards). This will enable us to capture only a portion of the emitted fluorescence spectrum and assess its diagnostic information.

The chemometric analysis of time-resolved fluorescence data shows promise as a possible method of classifying pancreatic tissue data. It may be used in the hybrid algorithm in conjunction with the other developed algorithms for pancreatic tissue classification.

4. Discussion and Conclusion

In all the algorithms the combination of classifiers extracted from both reflectance and fluorescence performed better than using information from either just reflectance or just fluorescence. The performance of the four developed tissue classification algorithms (Chemometric, PTI model, SpARC, and Hybrid) all show promise for pancreatic tissue classification using optical spectroscopy. The sensitivity and specificity of the algorithms for adenocarcinoma identification are comparable and in some cases better than reported literature performance of EUS-FNA which is generally considered the diagnostic standard.

Illustration III

1. Introduction

In this Illustration, Reflectance and Fluorescence spectroscopy were employed to differentiate between human pancreatic adenocarcinoma and chronic pancreatitis tissue using tissue classification algorithms that employed Principal Component Analysis (PCA) and Linear Discriminant analysis (LDA). Principal component analysis was used to identify the diagnostic features in the spectra and then LDA was employed to classify the data based on these features. This Illustration involves the development of a tissue diagnostic algorithm on an enhanced data set. Preliminary PCA analysis was also conducted on time-resolved fluorescence decay measurements from these tissues.

2. Methods 2.1 Human Studies

Reflectance and fluorescence spectra and time-resolved fluorescence decays were measured from freshly excised pancreatic tissue obtained during Whipple procedures. Multiple sites were measured on tissues obtained from 12 patients within 30 minutes of excision. A total of 90 sites were measured from all the patients and two measurements were made on each site. After data acquisition from each measurement site, a portion of tissue was removed to link optical measurements with histological analysis. The study was approved by the Institutional Review Board of the University of Michigan and patient consent was obtained prior to data acquisition.

2.2 Instrumentation

The clinically compatible, fiber-optic coupled RFLS, such as system 10 described herein, was employed for data acquisition.

2.3 Pathology and Inclusion Criterion

Pathology indicated that of the measured sites 17 were adenocarcinoma sites, 22 were chronic pancreatitis sites, and 11 were normal tissue sites. The rest of the sites were either malignant breast cancer that had metastasized to the pancreas (10 sites), intraductal papillary mucinous neoplasm (IPMN—8 sites), pancreatic intraepithelial neoplasia (PanIN—6 sites), serous cyst adenoma (SCA—8 sites), scar or fat tissue or both (5 sites) or a hybrid tissue site having two or more of the above mentioned pathologies (3 sites). These sites were excluded from the data set used for algorithm development. Furthermore, those measurements that were very noisy were also excluded from the data set (4 measurements). This left a total of 33 adenocarcinoma measurements, 40 chronic pancreatitis measurements, and 22 normal measurements of both fluorescence and reflectance spectra. Tissue algorithm development was undertaken with this set of data of 95 total measurements each (Set 1) of both fluorescence and reflectance spectra.

The time-resolved fluorescence data were measured either by detecting all emitted fluorescence photons (pancreatitis=31 measurements, normal=16 measurements, and adenocarcinoma=4 measurements) or by only detecting fluorescence photons emitted at >500 nm wavelength by placing a long-pass filter in front of the APD that cut on at 500 nm (adenocarcinoma=20 measurements).

2.4 Development of the Tissue Classification Algorithm

Figure 8:
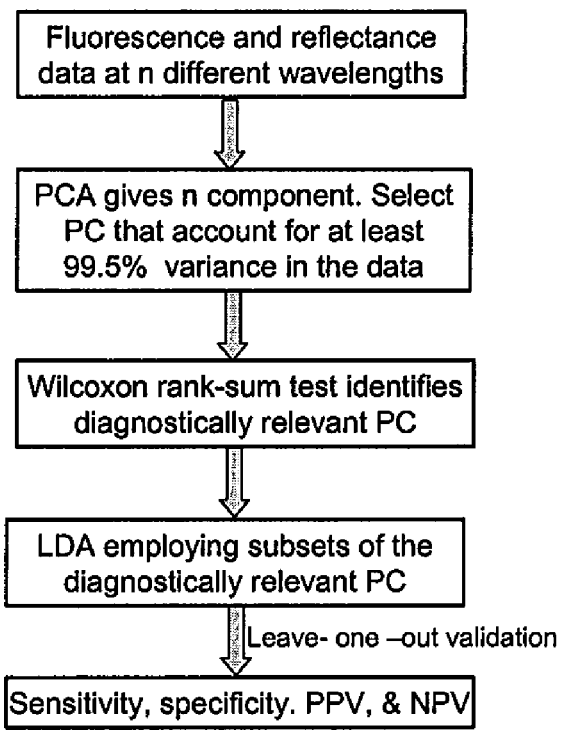
FIG. 8 illustrates a flow chart of steps in the tissue classification algorithm development process according to some embodiments of the invention and in connection with Illustration III.

FIG. 8 illustrates the steps involved in the tissue classification algorithm development process according to some embodiments. The acquired spectra were first analyzed using Principal component analysis (PCA). The Principal components (PC) that accounted of at least 99.5% of the variance in the data were identified. Wilcoxon-rank sum tests were undertaken on the fit-coefficients of these P) for each tissue type to identify the diagnostically relevant PC as described in Section 2.4.1 of this Illustration. Linear Discriminant Analysis (LDA) was then undertaken using various subsets of the diagnostically relevant PC (Section 2.4.2) to classify the spectral data employing a leave-one-out cross validation.

2.4.1. Principal Component Analysis (PCA) of the Spectra

PCA was employed to express each spectrum as a linear combination of a set of orthogonal basis vectors (or components) as discussed in the following: A. D. Joshi, J. A. Fessler, and R. A. Koeppe, "Improving PET receptor binding estimates from Logan plots using principal component analysis," Journal of Cerebral Blood Flow and Metabolism 28, 852-865 (2008). Of these components, the key-features of the data are captured by only a few vectors with high eigenvalues while the vectors corresponding to lower eigenvalues represent noise in the data. However, not all the key features of the spectra are diagnostically relevant (i.e. enabling differentiation between the tissue types). By identifying the few diagnostically relevant components, the dimensionality of the problem is reduced. The diagnostically relevant components were identified by fitting the principal components to the spectra. The components whose coefficients showed difference between tissue types were identified as diagnostically relevant.

The data spectra $\bar{s}_i \in R^{m \times 1}$ (i=1 to m) for different tissue types were grouped together and arranged row-wise in a matrix $S \in R^{m \times n}$ as shown below:

$$S = \begin{bmatrix} \overline{s}_1^T \\ \overline{s}_2^T \\ \vdots \\ \overline{s}_m^T \end{bmatrix} = \begin{bmatrix} \overline{s}_1^T \\ \vdots \\ \overline{s}_p^T \\ \vdots \\ \overline{s}_{p+q}^T \\ \vdots \\ \overline{s}_{p+q+r}^T \end{bmatrix}, \quad (11)$$

where, p, q and r (p+q+r=m) are the number of spectra for adenocarcinoma, chronic pancreatitis and normal tissue type respectively. Using PCA, the above shown n dimensional training set (corresponding to the n measured wavelengths) with m total spectra can be represented as a linear combination of n basis vectors as shown below:

$$S^T = CX, \quad (12)$$

where, $^T$ is the transpose operator, $C \in R^{n \times n}$ is the matrix of the n principal components, and X is a matrix of the fit coefficients.

$$X = \begin{bmatrix} x_{11} & x_{12} & \cdots & x_{1m} \\ x_{21} & \ddots & & \vdots \\ \vdots & & \ddots & \\ x_{n1} & \cdots & \cdots & x_{nm} \end{bmatrix}, \quad (13)$$

Where, an element $x_{ji}$ is the fit-coefficient of the $j^{th}$ component for the $i^{th}$ spectrum.

The principal component matrix C was obtained from S by employing the princomp function in MATLAB, which is incorporated herein by reference. The princomp function first calculates matrix $S_0$ by subtracting the column mean vector from each row of S. Then singular value decomposition is used to calculate the principal components as the eigenvectors of the sample covariance matrix $$\left(\frac{1}{m-1} S_0^T S_0\right).$$

Four Wilcoxon rank-sum tests were performed for the coefficients of the first 10 principal components: The hypothesis tested was that the mean fit-coefficients were significantly different for the principal component of (1) Adenocarcinoma (A) and the rest of the tissue types (2) A and chronic Pancreatitis (P), (3) A and Normal (N), (4) P and N. The principal components for which p-value was <0.05 were considered the diagnostically relevant components. The above analysis was done for both fluorescence (n=492) and reflectance spectra (n=521) separately to determine the principal components whose coefficients would be used for classification of tissue types (RPC: diagnostically relevant Reflectance PC, FPC: diagnostically relevant Fluorescence PC).

2.4.2. Linear Discriminant Analysis

Linear Discriminant Analysis (LDA) was employed using SPSS software, which is incorporated herein by reference, to distinguish between tissue types using the diagnostically relevant RPC and FPC. LDA employed a linear combination of the classification variables to distinguish between different tissue types. The analysis was undertaken by employing three different sets of diagnostically relevant PC variables: reflectance PC only, fluorescence PC only, or a combination of the reflectance and fluorescence PC variables. In the latter case, a stepwise DA was performed using minimization of Wilks' Lambda ($\Lambda$) criterion to assess the discriminating power of the variables and to select the best set of variables from diagnostically relevant RPC and FPC for classification. At each step, variables were considered for the classification algorithm only if the p-value representing the discrimination added by the variable satisfied the P-to-enter significance criterion (set as $\leq 0.05$). Out of those variables, the variable that minimized the $\Lambda$ was selected. At the next step, all variables that had already entered the algorithm were re-assessed to see if any of them no longer sufficiently discriminated between the classification groups (measured by P-to-remove value $\geq 0.25$). This was repeated until no variables satisfied the P-to-enter criterion. The variables retained at the end by the stepwise analysis were then employed to classify the data.

A leave-one-out cross-validation was undertaken to test the performance of each of the proposed tissue classification algorithms. For each algorithm, the data were divided into Training and Test data where each data was considered as Test data one at a time, while the remaining measurements were treated as Training data. The classifiers were then employed to classify the Test data using LDA. Each algorithm was implemented 95 times and sensitivity, specificity, positive predictive value (PPV) and negative predictive value (NPV) were calculated.

2.5. Time-resolved Fluorescence Measurements

Tissue classification using time-resolved fluorescence measurements acquired without a long-pass filter in front of the APD was restricted to normal and pancreatitis tissue measurements. This was because only four of the adenocarcinoma time-resolved fluorescence measurements were acquired without a long-pass filter. PCA was undertaken on the pancreatitis and normal tissue time-resolved fluorescence decays measured without the long-pass filter, with the premise that the shape of the decay curve should reflect changes in decay time for different tissue types, assuming the instrument response is not changing over the measurements. PCA was also carried out on the fluorescence and reflectance spectral data for the same subset of pancreatitis and normal data and LDA was performed to distinguish between pancreatitis and normal tissue sites using either only spectral data PC, or time-resolved data PC, or a combination of the two.

3. Results 3.1. Classification Using Reflectance Parameters

Table 28 lists the sensitivity, specificity, PPV and NPV for classifying tissue types using only the diagnostically relevant reflectance PC. For example, for classifying between Adenocarcinoma and chronic Pancreatitis RPC1, RPC2, RPC7, and RPC8 were employed.

TABLE 28

Classification using Reflectance spectra PC

| Tissue Type | Sensitivity (%) | Specificity (%) | PPV (%) | NPV (%) | Components |
|---|---|---|---|---|---|
| A vs. P & | 94 | 84 | 76 | 96 | RPC1, RPC2 |
| A vs. P | 79 | 88 | 84 | 83 | RPC1, RPC2, RPC7, RPC8 |
| A vs. N | 94 | 86 | 91 | 90 | RPC1, RPC2 |
| P vs. N | 80 | 82 | 89 | 69 | RPC1, RPC3, RPC5, RPC7, |

A: Adenocarcinoma; N: Normal; P: Pancreatitis 3.2. Classification Using Fluorescence Parameters Table 29 lists the sensitivity, specificity, PPV and NPV for classifying tissue types using only the diagnostically relevant fluorescence PC (Table 2). For example, for classifying between Adenocarcinoma and chronic Pancreatitis FPC1, FPC2, FPC6, and FPC11 were employed.

TABLE 29

Classification using Fluorescence spectra PC

| Tissue Type | Sensitivity (%) | Specificity (%) | PPV (%) | NPV (%) | Components |
|---|---|---|---|---|---|
| A vs. P & N | 79 | 79 | 67 | 88 | FPC1, FPC4, FPC6, FPC11 |
| A vs. P | 85 | 70 | 70 | 85 | FPC1, FPC2, FPC6, FPC11 |
| A vs. N | 76 | 91 | 93 | 71 | FPC1, FPC4, FPC8, FPC9 |
| P vs. N | 63 | 68 | 78 | 50 | FPC2, FPC7, FPC8, FPC9 |

A: Adenocarcinoma; N: Normal; P: Pancreatitis 3.3. Classification Using Fluorescence and Reflectance Parameters Table 30 lists the sensitivity, specificity, PPV and NPV for classifying tissue types using both diagnostically relevant fluorescence PC and reflectance PC, where a step-wise LDA was performed (as described in section 2.4.2) to further select classification variables from all the diagnostically relevant fluorescence and reflectance PC. The last column in Table 3 indicates the PCs used for the classification procedure. The results in Table 3 indicate that a combination of reflectance and fluorescence parameters will have a better sensitivity and specificity for identifying adenocarcinoma.

TABLE 30

Classification using Fluorescence and Reflectance spectra PC

| Tissue Type | Sensitivity (%) | Specificity (%) | PPV (%) | NPV (%) | Components |
|---|---|---|---|---|---|
| A vs. P & N | 91 | 90 | 83 | 95 | RPC1, RPC2, FPC1, FPC4, FPC6 |
| A vs. P | 82 | 85 | 82 | 85 | RPC1, RPC2, RPC8, FPC1 |
| A vs. N | 94 | 86 | 91 | 90 | RPC1, RPC2 |
| P vs. N | 83 | 86 | 92 | 73 | RPC1, RPC5, RPC7 |

A: Adenocarcinoma; N: Normal; P: Pancreatitis

Figure 9:
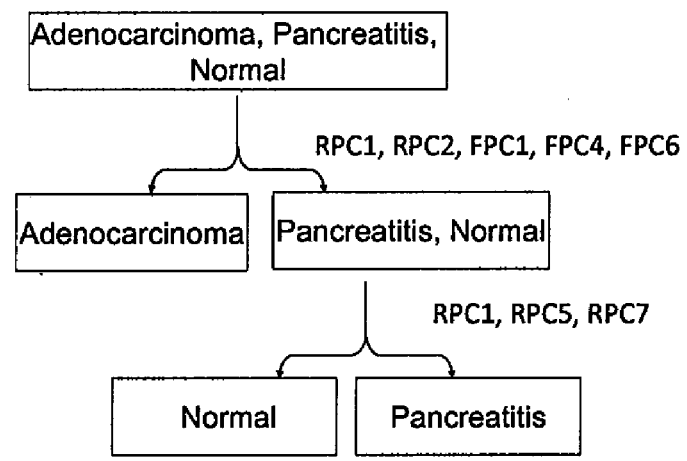
FIG. 9 illustrates a flow chart of a proposed tissue classification algorithm schematic for unknown data in accordance with some embodiments of the invention and in connection with Illustration III.

Based on the results in Table 30, data from an unknown tissue site could be classified in a two-step process where first it could be classified by employing RPC1, RPC2, FPC1, and FPC4, FPC6 into adenocarcinoma or not adenocarcinoma. If the data is classified as not cancer then RPC1, RPC5, and RPC7 could be employed to further classify the data into normal or chronic Pancreatitis as shown in FIG. 9. In a clinical setting, such a classification procedure could be undertaken in a few seconds, giving a quick classification scheme to either guide EUS-FNA or for marin detection during pancreatic surgery.

3.4. Classification Using Time-resolved Fluorescence Data

While the sample size of the adenocarcinoma data was not large enough to draw reliable conclusions, a Wilcoxon rank sum test of the decay times of normal and pancreatitis tissue indicated a difference in the mean decay times of the tissues (p-value=0.0064).

Tale 31 lists the algorithm performance for distinguishing pancreatitis from normal tissue using spectral PC only, time-resolved PC only, or a combination of the two (step-wise LDA; P-to-enter=0.08; P-to-remove=0.1). A combination of both spectral and temporal information improved the classification performance.

The time-resolved data are now being measured for fluorescence photons emitted at >500 nm wavelength as in that region, collagen emission is not dominating the fluorescence. It is thought that this might improve detection of changes in decay time due to cellular autofluorescence (NAD(P)H or FAD) to see if that enhances the difference between the various tissue types. Preliminary results show a difference between the decay times measured from adenocarcinoma with and without the long-pass filter (p-value=0.0021).

TABLE 31

Classification P vs. N using spectral and temporal PC

| Tissue Type | Sensitivity (%) | Specificity (%) | PPV (%) | NPV (%) | Components |
|---|---|---|---|---|---|
| P vs. N | 81 | 81 | 89 | 68 | RPC1, RPC5, RPC7 |
| P vs. N | 71 | 94 | 96 | 63 | TRPC1, TRPC5 |
| P vs. N | 87 | 94 | 96 | 79 | RPC1, RPC5, RPC7, TRPC5 |

N: Normal; P: Pancreatitis

4. Discussions and Conclusion

The combination of classifiers extracted from both reflectance and fluorescence performed better than using information from either just reflectance or just fluorescence. The median (range) of reported performance of EUS-FNA, the current accepted diagnostic standard are sensitivity: 83% (54-95%), specificity: 100% (71-100%), NPV: 72% (16-92%), and PPV: 100 (92-100%) for adenocarcinoma distinction from normal tissue and chronic pancreatitis. Maximum sensitivity, specificity, PPV, and NPV of the developed chemometric tissue classification algorithm for correctly identifying adenocarcinoma were: 91%, 90%, 83%, 95%, respectively. The classification performance of the chemometric algorithm for adenocarcinoma identification is comparable and in some cases better than reported performance of EUS-FNA. We note that the results exceed the NPV for EUS-FNA, which can be unreliable for ruling out malignancy. In the setting of pancreatitis, i.e. when the patient has adenocarcinoma and pancreatitis, the sensitivity of the chemometric algorithm (82%) is well above that of EUS-FNA (54%) for distinguishing adenocarcinoma from pancreatitis, which is an unmet clinical need in pancreatic cancer detection. Thus, the performance of the developed tissue classification algorithms, show promise for pancreatic tissue classification using optical spectroscopy. In a clinical setting such a classification procedure could be undertaken for rapid tissue classification scheme either guide EUS-FNA or for margin detection during pancreatic surgery.

The average fluorescence decay times for normal and pancreatitis tissue were found to differ (p<0.01). Classification algorithms that incorporated time-resolved fluorescence PC along with and reflectance and fluorescence spectral PC had the best classification performance for distinguishing between normal and pancreatitis tissue types indicating that inclusion of time-resolved data in the analysis could potentially improve the classification performance of the developed tissue classification algorithms.

Illustration IV

A photon-tissue interaction (PTI) model was utilized to analyze 96 pairs of diffuse reflectance and fluorescence spectra obtained from freshly excised human pancreatic tissues. For each pair of spectra, the PTI model extracted a nuclear size parameter from the measured reflectance, as well as the relative contributions of native tissue fluorophores (collagen, NADH, FAD) to the measured fluorescence. All four of the aforementioned parameters extracted from the PTI model were shown to be statistically significant for distinguishing pancreatic adenocarcinoma from normal pancreatic tissue and pancreatitis.

Reflectance and fluorescence spectra were measured from 50 pancreatic tissue sites, and after the RFLS measurements took place, a section was taken from each of these sites and sent to histology for diagnosis by a pathologist. Of the 50 sites used in this study, 11 were diagnosed by pathology as histologically normal, 22 were diagnosed as pancreatitis, and 17 were diagnosed as adenocarcinoma. From each of these sites (except for one adenocarcinoma site), two reflectance and two fluorescence spectra were taken. Three of the spectra were removed from the data set due to low SNR, resulting in 96 pairs of reflectance and fluorescence spectra that were individually fit using the PTI algorithm.

The PTI model has been described in detail elsewhere, see R. H. Wilson, M. Chandra, J. Scheiman, D. Simeone, B. McKenna, J. Purdy, and M. A. Mycek, "Optical spectroscopy detects histological hallmarks of pancreatic cancer," Opt. Express 17, 17502-17516 (2009) for example, as well as herein. In short, an empirical model of reflectance as a function of the tissue scattering and absorption coefficients is employed to construct a wavelength-resolved scaling factor to transform an average measured "canonical normal" pancreatic tissue reflectance spectrum. A model spectrum resulting from this transformation was then fit to each individual measured reflectance spectrum via minimization of the cost function $|R_{model(\lambda)} - R_{measured}(\lambda)|$.

In the fitting procedure, the reduced scattering coefficient of the tissue ($\mu_s(1-g)$, where g is the tissue anisotropy) was modeled as the sum of two Mie theory terms: one for spherical scatterers (cell nuclei) and one for cylindrical scatterers (collagen fibers). The cylindrical Mie scattering term was kept constant, but in the spherical Mie scattering term, the ratio L/Lo of the diameter of the cell nuclei in the model to that of normal pancreatic tissue was varied from 1.0 to 1.5 in steps of 0.1. The refractive indices $n_s$ and $n_c$ of the spherical and cylindrical scatterers were also kept constant. The absorption coefficient was modeled as a linear combination of oxy- and deoxy-hemoglobin. The total hemoglobin concentrations of the "canonical normal" reflectance spectrum ($[Hb]_{tot,N}$) and the modeled spectrum ($[Hb]_{tot,model}$) were both varied from 2.5 μM to 25 μM in steps of 2.5 μM. The blood-oxygen saturation of the normal reflectance spectrum ($SO_{2,N}$) and the modeled spectrum ($SO_{2,model}$) were both varied from 0.1 to 0.9 in steps of 0.2. The values of L/Lo, $[Hb]_{tot,N}$, $[Hb]_{tot,model}$, $SO_{2,N}$, and $SO_{2,model}$ that minimized the cost function were extracted from the fit of the reflectance model to each individual measured reflectance spectrum.

Once the model described above was fit to an individual measured reflectance spectrum, the reduced scattering coefficient $\mu_s(1-g)$ extracted from the best fit was put into a Beer-Lambert factor of the form $\exp[(\mu_a + \mu_s(1-g))z]$ to correct the corresponding measured fluorescence spectrum for attenuation artifacts. In this equation, the average path length z of a fluorescent photon in the tissue was taken to be 0.064 cm for all tissue types; this value had been estimated previously from Monte Carlo simulations. In order to avoid undercorrection or over-correction, the values of $[Hb]_{tot,model}$ and $SO_{2,model}$ were allowed to vary in this procedure as well. The resulting "intrinsic" fluorescence spectrum $F_{intrinsic}(\lambda)$ was then fit to a linear combination BasisFit(λ) of the basis spectra of three endogenous tissue fluorophores: collagen, NADH, and FAD. These basis spectra were blue-shifted by 12 nm to account for the fact that they were measured in chemical solvents and not a biological tissue environment. The best fit was determined via minimization of the cost function $|BasisFit(\lambda) - F_{intrinsic}(\lambda)|$ from 400-638 nm [12]. The fit coefficients $C_{coll}$, $C_{nadh}$, and $C_{fad}$ extracted from this fit were then normalized via division by their sum, in order to obtain the percentage contributions % COLL, % NADH, and % FAD from the constituent endogenous fluorophores. These percentages summed to 1 for each measured fluorescence spectrum.

A two-tailed t-test was performed for each parameter, L/Lo, % COLL, % NADH, and % FAD, to see if the differences in the parameter were statistically significant for distinguishing pancreatic adenocarcinoma from normal pancreatic tissue, distinguishing pancreatic adenocarcinoma from pancreatitis, and distinguishing malignant pancreas (adenocarcinoma) from benign pancreas (normal pancreatic tissue and pancreatitis). For each of these three cases, all four parameters were found to be statistically significant ($p<0.05$). When these four parameters were used as inputs to a Linear Discriminant Analysis (LDA) algorithm for classification of the individual tissue spectra as either "adenocarcinoma" or "normal and pancreatitis", 31 of the 33 adenocarcinoma spectra were classified correctly and 52 of the 62 "normal and pancreatitis" spectra were classified correctly. The sensitivity, specificity, positive predictive value, and negative predictive value of the PTI-LDA algorithm were 93.9%, 83.9%, 75.6%, and 96.2%, respectively. These results show the potential of the PTI model to extract diagnostically-relevant biological parameters from measured reflectance and fluorescence spectra of human pancreatic tissues, among other things. The potential of the PTI algorithm to correctly distinguish pancreatic adenocarcinoma from pancreatitis is further illustrated by this Illustration.

Illustration V

1. Introduction

This Illustration provides an assessment of the diagnostic accuracy of algorithms developed for pancreatic tissue classification using data from fiber-optic probe-based bi-modal optical spectroscopy, an approach that would be compatible with minimally-invasive diagnostic procedures for early cancer detection in the pancreas. A total of 95 fluorescence and 95 reflectance spectra were considered from 50 freshly excised tissue sites (including human pancreatic adenocarcinoma, chronic pancreatitis (inflammation), and normal tissues) on 9 patients. Classification algorithms using linear discriminant analysis were developed to distinguish among tissues and leave-one-out cross validation was employed to assess the classifiers' performance. The SpARC (Spectral Areas and Ratios Classifier) algorithm employed a combination of reflectance and fluorescence data and had the best performance, with sensitivity, specificity, negative predictive value, and positive predictive value for correctly identifying adenocarcinoma being 85%, 90%, 92%, and 82%, respectively. These results exceed the performance of EUS-FNA, which is insensitive to distinguishing adenocarcinoma from pancreatitis and is unreliable at ruling out malignancy in the pancreas.

2. Methods 2.1 Human Studies

In this illustration, pancreatic tissue classification algorithms employing fluorescence data alone, reflectance data alone, or a combination of the two, were used to determine whether both reflectance and fluorescence information were necessary for optimal tissue classification. Optical spectra were measured from freshly excised pancreatic tissues obtained during surgery. A system such as system 10 discussed herein was employed to study 50 tissue sites from 9 patients within 30 minutes of tissue excision. After optical data acquisition from each measurement site, tissue at the site was removed for histopathological analysis. The study was approved by the Institutional Review Board of the University of Michigan (U of M) Medical School and patient consent was obtained prior to data acquisition.

2.2 Methods for Classification

Acquired fluorescence spectra in the 360-750 nm range were corrected for spectral instrument response after background correction. Reflectance spectra were background subtracted (R) and then scaled by the lamp reflectance spectrum ($R_o$) to obtain corrected reflectance spectra ($R/R_o$) in the 400-750 nm spectral range. All spectra were then normalized by scaling the peak intensity value to unity. Tissue algorithm development was undertaken with 95 fluorescence measurements and 95 reflectance measurements: 33 fluorescence and reflectance measurements were made on 17 adenocarcinoma sites, 40 were made on 22 pancreatitis sites, and 22 were made on 11 normal sites.

Figure 10:
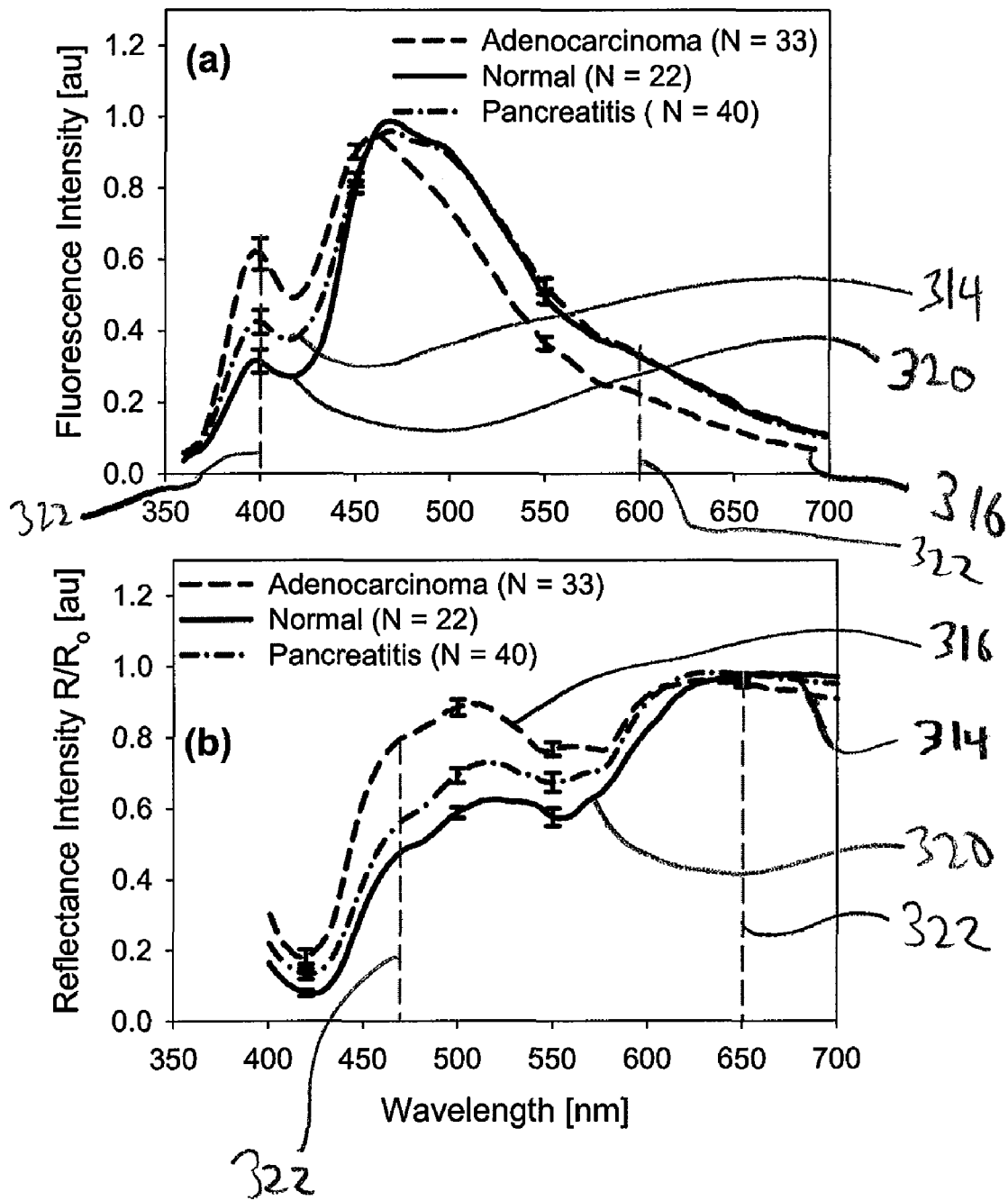
FIGS. 10a and 10b are graphs depicting the mean of normalized measured fluorescence (FIG. 10a) and reflectance (FIG. 10b) and spectra for adenocarcinoma, pancreatitis, and normal pancreatic tissues along with the standard error at select wavelengths in connection with some embodiments of the invention and Illustration IV.

FIGS. 10a,b shows the mean of normalized measured reflectance and fluorescence spectra for adenocarcinoma (dashed line 316), pancreatitis (dot-dashed line 314), and normal (solid line 320) pancreatic tissues along with the standard error at select wavelengths. The adenocarcinoma sites showed a markedly higher reflectance than pancreatitis and normal tissue sites in the 450 to 540 nm range and a higher (lower) fluorescence at around 400 nm (450 to 700 nm range). To classify the tissue spectra based on these apparent differences, the ratio $R_{ratio}=R_{470}/R_{650}$ was calculated for each reflectance spectrum, the wavelength integrated fluorescence ($F_{area}$) was calculated as the area under each normalized fluorescence spectrum, and the ratio $F_{ratio}=F_{400}/F_{600}$, was calculated for each fluorescence spectrum. The vertical dashed lines 322 in FIGS. 10a,b indicate the wavelength at which the ratios $R_{ratio}$ and $F_{ratio}$ were calculated.

Three different sets of these calculated spectral parameters ("classification variables") were employed to develop tissue classification algorithms for distinguishing (a) adenocarcinoma (A) from pancreatitis (P) and normal (N) tissue, (b) A from P tissue, (c) A from N tissue, and (d) P from N tissue. A leave-one-out cross-validation was undertaken to test the performance of the proposed tissue classification algorithms by considering each measured spectrum as the test data and by employing the remaining spectra as training data in the classification algorithm. Linear Discriminant Analysis (LDA) was employed using SPSS software to classify the test data using the three different sets of classification variables. LDA employs a linear combination of the classification variables to classify data. This process was repeated for each spectrum and the sensitivity, specificity, negative predictive value (NPV), and positive predictive value (PPV), of the classification algorithms were calculated.

The first classification algorithm, RSpARC (reflectance spectral areas and ratios classifier), employed $R_{ratio}$ as the sole classification variable for LDA and Table 32 provides the algorithm performance. The second algorithm, FSpARC (fluorescence spectral areas and ratios classifier), employed $F_{area}$ and $F_{ratio}$ as the classification variables for LDA and Table 33 gives that algorithm's performance. In the third algorithm, SpARC (spectral areas and ratios classifier), stepwise LDA was performed using minimization of Wilks' Lambda (Λ) criterion (P-to-enter 0.06; P-to-remove 0.01) to assess the discriminating power of the variables and to select the best set of variables from $R_{ratio}$, $F_{area}$, and $F_{ratio}$ for classification. The variables retained by the stepwise analysis were then employed to classify the data. Table 34 shows the performance of this algorithm along with the variables retained for each classification. For example, classification of A vs. P and N employed $R_{ratio}$ and $F_{ratio}$. The combination of classifiers extracted from both reflectance and fluorescence (Table 34) performed better than using information from either just reflectance (Table 32) or just fluorescence (Table 33), indicating that bi-modal optical spectroscopy with both fluorescence and reflectance is needed for pancreatic tissue classification.

TABLE 32

RSpARC algorithm - reflectance only

| Tissue Type | Sensitivity (%) | Specificity (%) | NPV (%) | PPV (%) |
|---|---|---|---|---|
| A vs. P and N | 85 | 85 | 91 | 76 |
| A vs. P | 85 | 85 | 87 | 82 |
| A vs. N | 88 | 95 | 84 | 97 |
| P vs. N | 58 | 82 | 51 | 85 |

N: Normal; P: Pancreatitis; A: Adenocarcinoma

TABLE 33

FSpARC algorithm - fluorescence only

| Tissue Type | Sensitivity (%) | Specificity (%) | NPV (%) | PPV (%) |
|---|---|---|---|---|
| A vs. P and N | 55 | 87 | 78 | 69 |
| A vs. P | 52 | 85 | 68 | 74 |
| A vs. N | 58 | 91 | 59 | 90 |
| P vs. N | 58 | 64 | 45 | 74 |

N: Normal; P: Pancreatitis; A: Adenocarcinoma

TABLE 34

SpARC algorithm - relectance and fluorescence

| Tissue Type | Sensitivity (%) | Specificity (%) | NPV (%) | PPV (%) |
|---|---|---|---|---|
| A vs. P and N[a,b] | 55 | 87 | 78 | 69 |
| A vs. P[a] | 52 | 85 | 68 | 74 |
| A vs. N[a] | 58 | 91 | 59 | 90 |
| P vs. N[a,c] | 58 | 64 | 45 | 74 |

Classification parameters
[a]$R_{ratio}$;
[b]$F_{ratio}$;
[c]$F_{area}$

Figure 11:
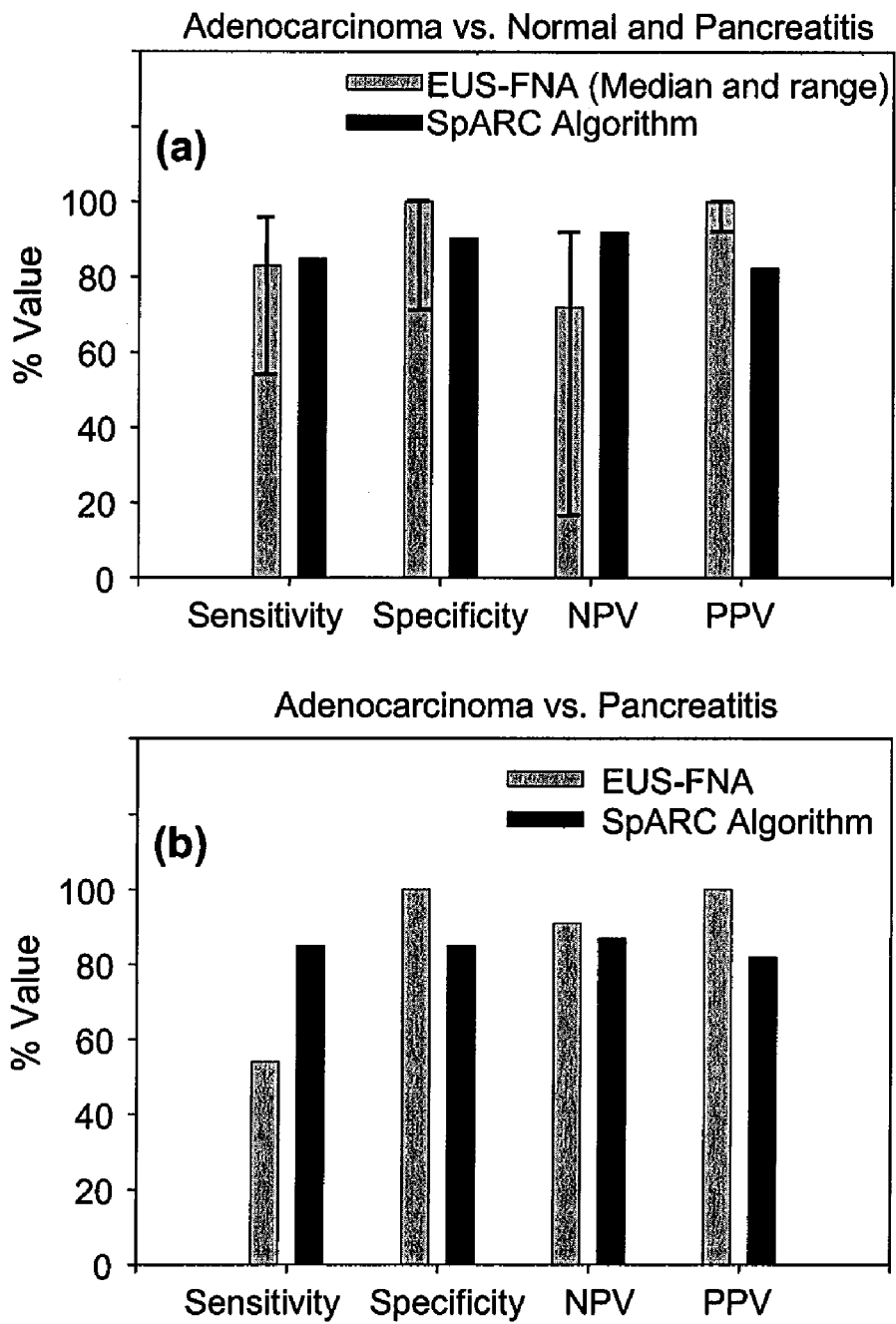
FIG. 11a is a bar graph depicting the median and range of sensitivity, specificity, NPV, and PPV for adenocarcinoma identification using clinical EUS-FNA and the SpARC algorithm
FIG. 11b is a bar graph depicting the performance of EUS-FNA (gray bars) and the SpARC algorithm for distinguishing between adenocarcinoma and pancreatitis in the setting of chronic pancreatitis according to some embodiments of the invention and Illustration IV.

The performance of the SpARC algorithm for adenocarcinoma distinction from normal tissue and chronic pancreatitis is comparable to that of, and in some cases better than, the reported performance of EUS-FNA, the currently accepted diagnostic standard. FIG. 11(a) plots in light gray the median (range) of reported EUS-FNA sensitivity: 83% (54-95%), specificity: 100% (71-100%), NPV: 72% (16-92%), and PPV: 100 (92-100%) for adenocarcinoma distinction from normal tissue and chronic pancreatitis. Plotted in dark gray for comparison is the performance of the SpARC algorithm (first row of Table 34). According to the results, the SpARC results exceed the NPV for EUS-FNA, which can be unreliable for ruling out malignancy.

In the setting of pancreatitis, i.e. when the patient has adenocarcinoma and pancreatitis, the sensitivity of SpARC (85%) is well above that of EUS-FNA (54%) (FIG. 11(b)) for distinguishing adenocarcinoma from pancreatitis, which is an unmet clinical need in pancreatic cancer detection. Based on the results in Table 34, a potential method for classifying an unknown tissue site could employ $R_{ratio}$ and $F_{ratio}$ to classify the data set as adenocarcinoma or not adenocarcinoma using LDA. If the data is classified as not cancer, then $R_{ratio}$ and $F_{area}$ could be employed to classify it as pancreatitis or normal tissue types.

While this Illustration involved an ex vivo setting, the performance of the developed tissue classification algorithm shows promise for clinical pancreatic tissue classification using bi-modal optical spectroscopy. In other embodiments, the methods described herein will also involve data acquisition in vivo, with the aim deploying the fiber-optic probe, as in system 10, through a needle for optically-guided EUS-FNA.

Illustration VI

1. Introduction

As discussed herein, reflectance and fluorescence spectral features could potentially be employed for human pancreatic cancer detection. An empirical PTI model to quantitatively link those spectroscopic measurements to histologically known characteristics of malignant and non-malignant human pancreatic tissues is also provided. The PTI reflectance model incorporated information about light scattering by cell nuclei and collagen fibers, as well as absorption by oxygenated and deoxygenated hemoglobin. The PTI fluorescence model then corrected fluorescence spectra measured at the same site as the reflectance spectra for absorption and scattering artifacts.

This Illustration provides, among other things, a further developed PTI model which is employed to analyze 96 pairs of reflectance and fluorescence spectra from freshly excised human pancreatic tissues. For each pair of spectra, the PTI model extracted a cellular nuclear size parameter from the measured reflectance, and the relative contributions of extracellular and intracellular fluorophores to the intrinsic fluorescence. The results indicated inter alia a statistically significant increase in the nuclear size of adenocarcinoma (relative to both normal pancreatic tissue and chronic pancreatitis) and a statistically significant increase in the extracellular collagen contribution to fluorescence in both adenocarcinoma and chronic pancreatitis (relative to normal pancreatic tissue). This suggests that reflectance and fluorescence spectroscopies have the potential to quantitatively distinguish among pancreatic tissue types, including normal pancreatic tissue, chronic pancreatitis, and pancreatic adenocarcinoma, via biophysical tissue properties extracted from the spectra.

2. Experimental Methods 2.1 Instrumentation

A RFLS device, such as system 10 and the embodiments thereof described herein, measured reflectance and fluorescence from human pancreatic tissue samples. At each tissue site, fluorescence and reflectance measurements were made in sequence by using shutters to block the other light source. Each fluorescence (reflectance) measurement had an associated acquisition time of 2 seconds (2.5 seconds). All measured reflectance and fluorescence spectra were background-corrected and corrected for the instrument response function. Corrected reflectance spectra $R/R_o$ were obtained by background subtraction and then dividing by the reflectance spectrum $R_o$ of the lamp. The lamp spectrum $R_o$ was measured by placing a reflectance standard (SRS-50-010, Labsphere, North Sutton, N.H.) or a neutral density filter (optical density 0.05) at the distal end of the probe and collecting the lamp light that was reflected from the surface of the reflectance standard. Each wavelength-resolved spectrum was normalized to peak intensity.

2.2 Human Studies

Reflectance and fluorescence spectra were measured from human pancreatic tissue samples within 30 minutes of excision, during operative procedures (Whipple procedure or distal pancreatectomy) performed on 9 patients (average age 62±11 years; 7 female, 2 male). The study received approval from the Institutional Review Board of the U of M Medical School. Prior to data acquisition, written consent was obtained from each patient.

Spectra were measured from 50 pancreatic tissue sites. Immediately following optical measurement, a tissue biopsy was taken from each of these sites and used for histopathologic analysis. Of the 50 sites, 11 were diagnosed by pathology as histologically normal, 22 were diagnosed as chronic pancreatitis (inflammation), and 17 were diagnosed as adenocarcinoma. All pancreatic adenocarcinoma spectra in this study were from patients who had concurrent histologic evidence of chronic pancreatitis in addition to pancreatic adenocarcinoma. Two wavelength-resolved reflectance spectra and two wavelength-resolved fluorescence spectra were taken from each tissue site, except for one adenocarcinoma site, from which only one set of these three measurements was taken.

Two pairs of chronic pancreatitis spectra were excluded because the fluorescence spectra had a signal-to-noise ratio (SNR) of less than 25, where SNR was defined to be the mean signal at peak fluorescence divided by the standard deviation of the noise in the measured spectrum. Another pair of chronic pancreatitis spectra was excluded because the intensity of the reflectance signal at 550 nm was less than 1/10 of that at 650 nm. The remaining 96 pairs of reflectance and fluorescence spectra (22 pairs of normal spectra, 41 pairs of chronic pancreatitis spectra, 33 pairs of adenocarcinoma spectra) were individually fit using the PTI model.

3. Photon-tissue Interaction (PTI) Model 3.1 PTI Reflectance Model and Fitting Procedure The PTI model is described in detail herein. Briefly, an empirical model of reflectance $R^{EMP}(\mu_s, \mu_a; \lambda)$ as a function of the tissue scattering coefficient $\mu_s$ (related to the nuclear diameter L and nuclear refractive index $n_s$) and absorption coefficient $\mu_a$ (related to the total hemoglobin concentration $[Hb]_{tot}$ and blood oxygen saturation $SO_2$) was employed to construct a wavelength-resolved scaling factor to transform an average measured "canonical normal" pancreatic tissue reflectance spectrum $R^{MEASURED}_{NORMAL}(\mu_a, \mu_s; \lambda)$ into the PTI model spectrum $R^{PTI}_{UNKNOWN}(\mu_a, \mu_s; \lambda)$ for each of the 96 individual measured reflectance spectra:

$$R^{PTI}_{UNKNOWN}(\mu_a, \mu_s; \lambda) = (R^{MEASURED}_{NORMAL}(\mu_a, \mu_s; \lambda)) \left( \frac{R^{EMP}_{UNKNOWN}(\mu_a, \mu_s; \lambda)}{R^{EMP}_{NORMAL}(\mu_a, \mu_s; \lambda)} \right). \quad (14)$$

The PTI-modeled spectra are denoted "unknown" because the model was blinded to pancreatic tissue type. Each model spectrum $R^{PTI}_{UNKNOWN}(_a, _s;)$ resulting from Eq. (1) was individually fit to the corresponding measured reflectance spectrum $R^{MEASURED}(_a, _s;)$ by varying the nuclear diameter L, total hemoglobin concentration $[Hb]_{tot}$, and blood-oxygen saturation $SO_2$ over biologically reasonable ranges (Table 1) and minimizing the cost function $|R^{PTI}_{UNKNOWN} - R^{MEASURED}|$ over the wavelength range of 400 nm to 700 nm.

TABLE 35

Ranges and step sizes for tissue parameters in the PTI model

| Tissue parameter | Minimum value | Maximum value | Step size |
|---|---|---|---|
| L | 9 m | 13.5 m | 0.9 m |
| $[Hb]_{tot}$ | 2.5 M | 25 M | 2.5 M |
| $SO_2$ | 0.1 | 0.9 | 0.2 |

The fitting procedure in this study was identical to those discussed herein and in R. H. Wilson, M. Chandra, J. Scheiman, D. Simeone, B. McKenna, J. Purdy, and M. A. Mycek, "Optical spectroscopy detects histological hallmarks of pancreatic cancer," Opt. Express 17, 17502-17516 (2009)., except for four changes: (1) The measured "canonical normal" spectrum was taken to be an average of all 22 measured normal spectra. (Each normal reflectance spectrum was first normalized to its peak value in the 400-700 nm wavelength range, then all 22 of these spectra were averaged, and, finally, the resulting spectrum was normalized to the peak again to create the "canonical normal" spectrum.). (2) The concentration of collagen fibers (cylindrical scatterers) for all unknown reflectance spectra was set to three times that of the canonical normal (motivated by previous work demonstrating that the mean collagen content of both pancreatic cancer and tumor-associated chronic pancreatitis was roughly three times as high as that of normal pancreatic tissue). This approximation was not expected to have a significant effect on the fitting procedure, because the key disease-related changes in the reflectance spectra were expected to be captured by changes in the variable L. (3) The refractive index of cell nuclei for all tissue types was set to a constant value of 1.375, which was in good agreement with the previous results. (4) The nuclear diameter L was varied from 9 μm to 13.5 μm, which contains the anticipated range for the pancreatic tissue types examined in this study.

Thus, the parameters extracted from the best fit of each "unknown" reflectance spectrum to the PTI model were the mean diameter L of the cell nuclei, as well as the total hemoglobin concentration and blood-oxygen saturation. The value of L from each "unknown" reflectance spectrum was compared to the value $L_o$ (set to 9 μm) that had been input into the PTI model for the mean cellular nuclear diameter of the "canonical normal" tissue. The ratio of $L/L_o$, termed the nuclear dilation factor, was calculated for each "unknown" reflectance spectrum. The tissue scattering properties extracted from the PTI model were then employed to correct the corresponding fluorescence spectra for attenuation artifacts, as described in the following Section 3.2 of this Illustration.

3.2 PTI Fluorescence Model and Fitting Procedure

Once the model described above was fit to an individual measured reflectance spectrum, the corresponding measured fluorescence spectrum $F_{MEASURED}(\lambda)$ was corrected for scattering and absorption attenuation artifacts with a Beer-Lambert factor, where the scattering coefficient was obtained from fitting the reflectance spectrum, as discussed above in Section 3.1. The resulting "intrinsic" fluorescence spectrum $F_{INTRINSIC}(\lambda)$ was fit to a linear combination of the basis spectra from three endogenous tissue fluorophores: extracellular collagen, intracellular NADH, and intracellular FAD, as described previously:

$$F_{INTRINSIC}(\lambda) = C_{COLL}F_{COLL}(\lambda) + C_{NADH}F_{NADH}(\lambda) + C_{FAD}F_{FAD}(\lambda). \quad (15)$$

The extracted fit coefficients $C_{COLL}$, $C_{NADH}$, and $C_{FAD}$ were then normalized via division by their sum, in order to obtain the percentage contributions % COLL, % NADH, and % FAD from the constituent endogenous tissue fluorophores. These percentages summed to 100% for each measured fluorescence spectrum.

4. Results 4.1 Measured Reflectance and Fluorescence Spectra from Human Pancreatic Tissues FIGS. 12a,b shows representative reflectance and fluorescence spectra measured from normal pancreatic tissue (solid line 420), chronic pancreatitis (dotted line 414), and pancreatic adenocarcinoma (dashed line 416). As reported previously, there are noticeable differences between the spectra of the different tissue types. From 450 nm to 530 nm, there is a significant increase in the amplitude of the adenocarcinoma reflectance spectrum (relative to normal and chronic pancreatitis), attributed to the increased size of cell nuclei in adenocarcinoma. Near 400 nm, there are notable increases in the amplitude of the adenocarcinoma and chronic pancreatitis fluorescence spectra (relative to normal), attributed to the increased extracellular collagen content in adenocarcinoma and chronic pancreatitis.

4.2 Fits of PTI Model to Reflectance and Fluorescence Spectra

Figure 12:
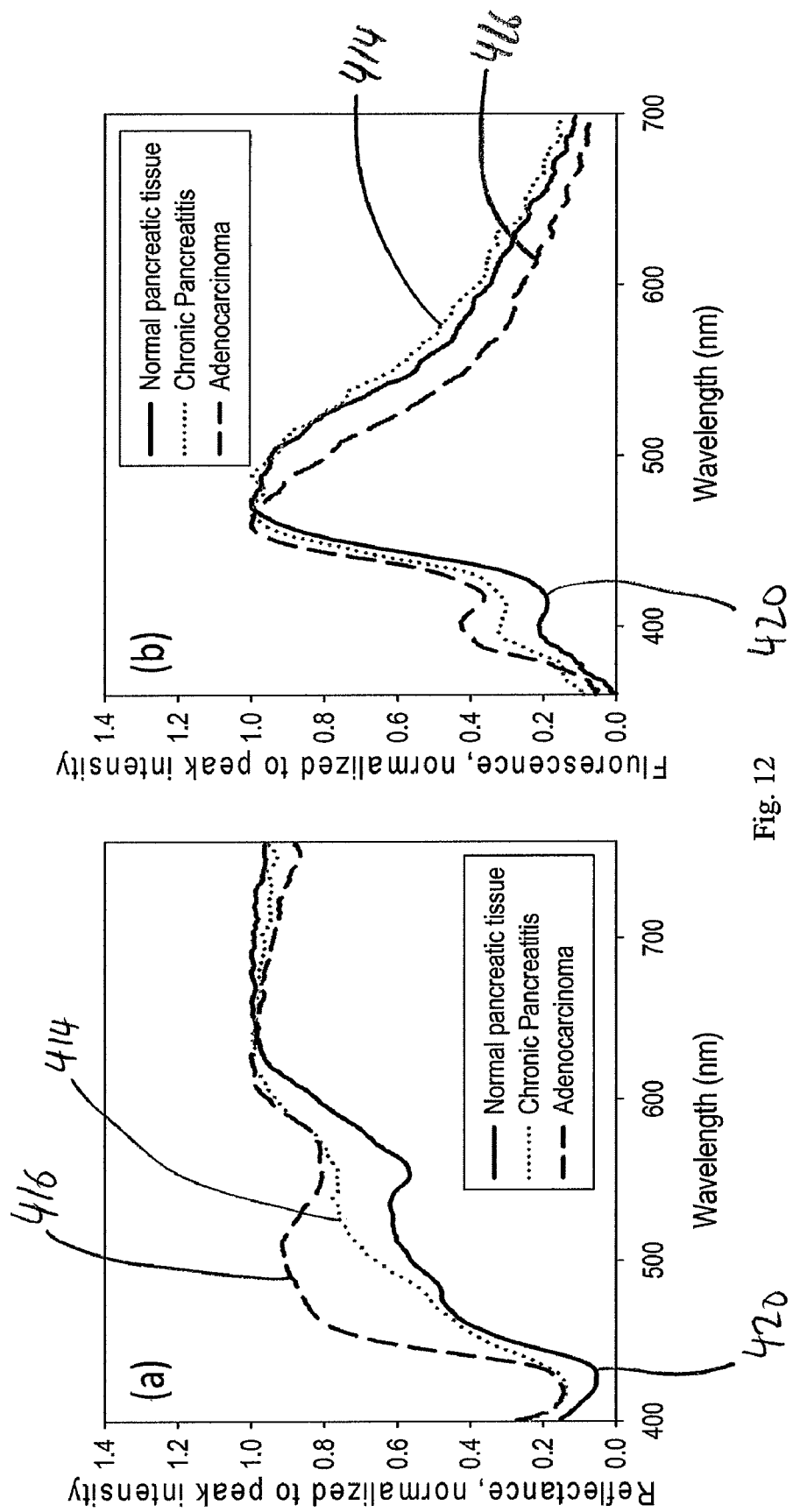
FIGS. 12a,b are graphs which are representative of reflectance (FIG. 12a) and fluorescence (FIG. 12b) spectra of normal pancreatic tissue, chronic pancreatitis, and pancreatic adenocarcinoma in connection with some embodiments of the invention and Illustration VI.
Figure 13:
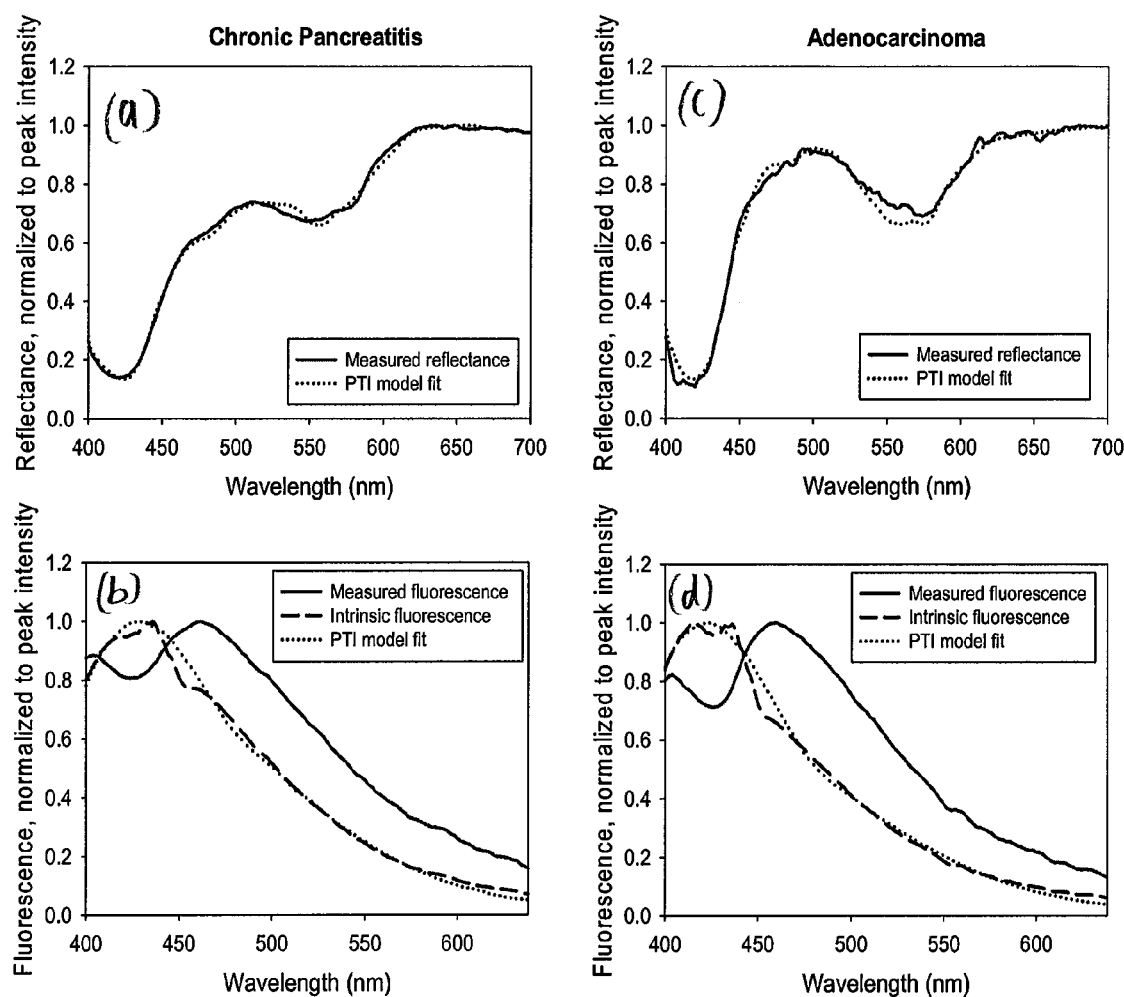
FIG. 13 includes graphs of the best fits of the PTI model to measured reflectance spectra and intrinsic fluorescence spectra for chronic pancreatitis (FIG. 13a and FIG. 13b, respectively) and adenocarcinoma spectra (FIG. 13c and FIG. 13d, respectively) in connection with some embodiments of the invention and Illustration VI.

FIG. 13 shows best fits of the PTI model to reflectance and fluorescence spectra from chronic pancreatitis (FIGS. 13a,b) and pancreatic adenocarcinoma (FIGS. 13c,d). The average error in fit of the PTI reflectance model to the 96 measured spectra was less than 15% in the wavelength range 450-530 nm. This spectral range is where significant differences in spectral amplitude were reported for adenocarcinoma, relative to normal pancreatic tissue and pancreatitis, as can be seen in FIG. 12(a). The average error in fit of the PTI fluorescence model to the 96 "intrinsic" fluorescence spectra was less than 6% in the wavelength range of 500-550 nm, in which key differences in spectral amplitude were reported for the different pancreatic tissue types (see FIG. 12(b)). When the 11 (out of 96) reflectance spectra with the highest cost functions were discarded, the average error in fit of the PTI reflectance model to the remaining 85 reflectance spectra fell below 10% in the 450-530 nm wavelength range, the average error in fit of the PTI fluorescence model to the 85 corresponding fluorescence spectra in the 500-550 nm wavelength range was nearly unchanged (remaining at less than 6%), and there was no significant change to the mean or standard error for the extracted parameters (see Sections 4.3 and 4.4 below in connection with this Illustration).

4.3 PTI Reflectance Model Extracts Cellular Nuclear Dilation Factor

Figure 14A:
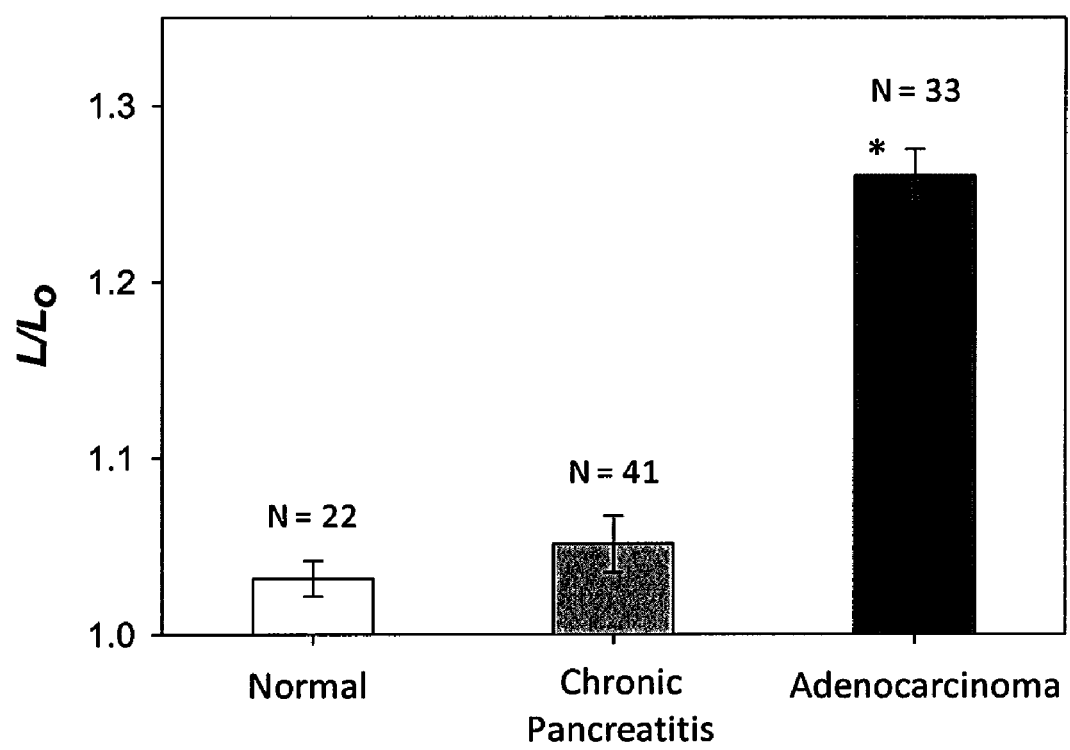
FIG. 14a is a bar graph depicting extracted nuclear dilation factor $L/L_o$ for normal pancreatic tissue (N=22 spectra), chronic pancreatitis (N=41 spectra), and pancreatic adenocarcinoma (N=33 spectra), which shows differences that were statistically significant (*, $p<2\times10^{-9}$ from Wilcoxon rank-sum tests) for distinguishing adenocarcinoma from normal pancreatic tissue as well as distinguishing adenocarcinoma from chronic pancreatitis, among other things, in connection with Illustration VI.

FIG. 14a shows the cellular nuclear dilation factor $L/L_o$ extracted from the PTI model for each pancreatic tissue type. The mean±standard error values of $L/L_o$ extracted for normal pancreatic tissue, chronic pancreatitis, and pancreatic adenocarcinoma were 1.03±0.01, 1.05±0.02, and 1.26±0.02, respectively. The extracted parameter $L/L_o$ can distinguish between adenocarcinoma and normal pancreatic tissue, as well as between adenocarcinoma and chronic pancreatitis ($p<2\times10^{-9}$ from Wilcoxon rank-sum tests). This result is consistent with the larger average cellular nuclear diameters found in histopathological analysis of pancreatic adenocarcinoma relative to normal pancreatic tissue and chronic pancreatitis.

Figure 14B:
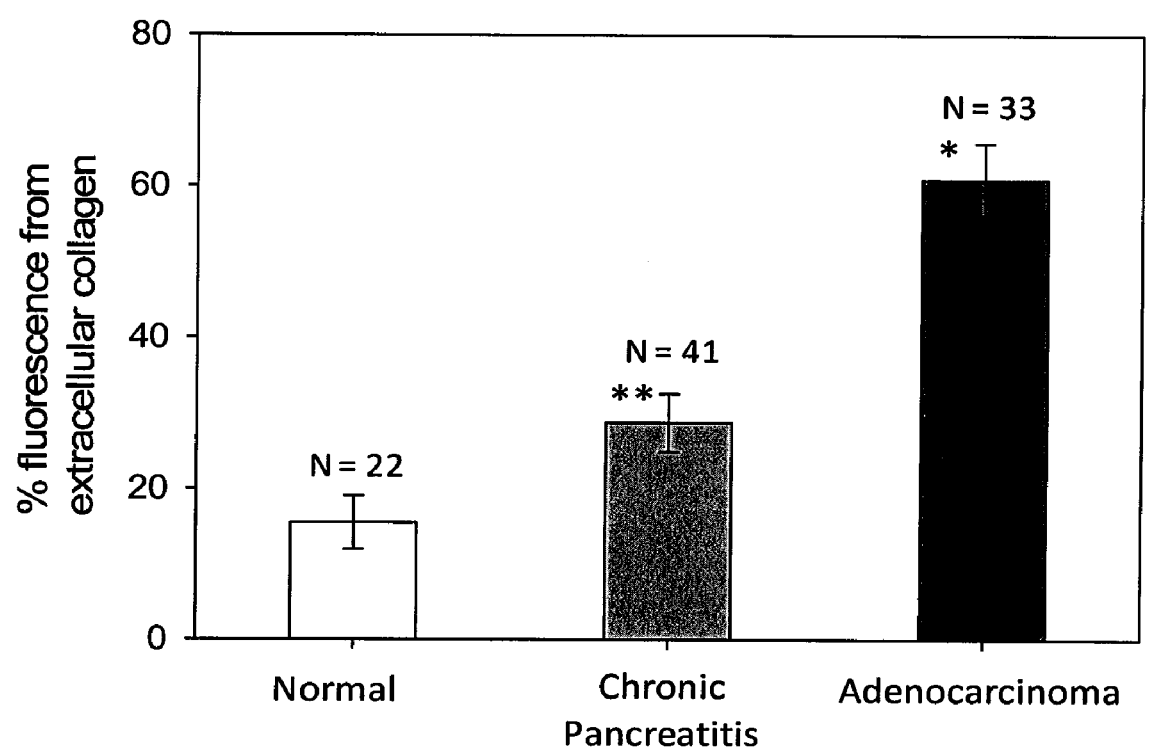
FIG. 14b is a bar graph depicting extracted percentage contributions of extracellular collagen to intrinsic fluorescence spectra of normal pancreatic tissue (N=22 spectra), chronic pancreatitis (N=41 spectra), and pancreatic adenocarcinoma (N=33 spectra) which shows differences that were statistically significant for distinguishing adenocarcinoma from normal pancreatic tissue as well as distinguishing adenocarcinoma from chronic pancreatitis (*, $p<2\times10^{-5}$ from Wilcoxon rank-sum tests) and differences were also statistically significant for distinguishing chronic pancreatitis from normal pancreatic tissue (**, $p<5\times10^{-2}$ from Wilcoxon rank-sum test), among other things, in connection with Illustration VI.
Figure 15:
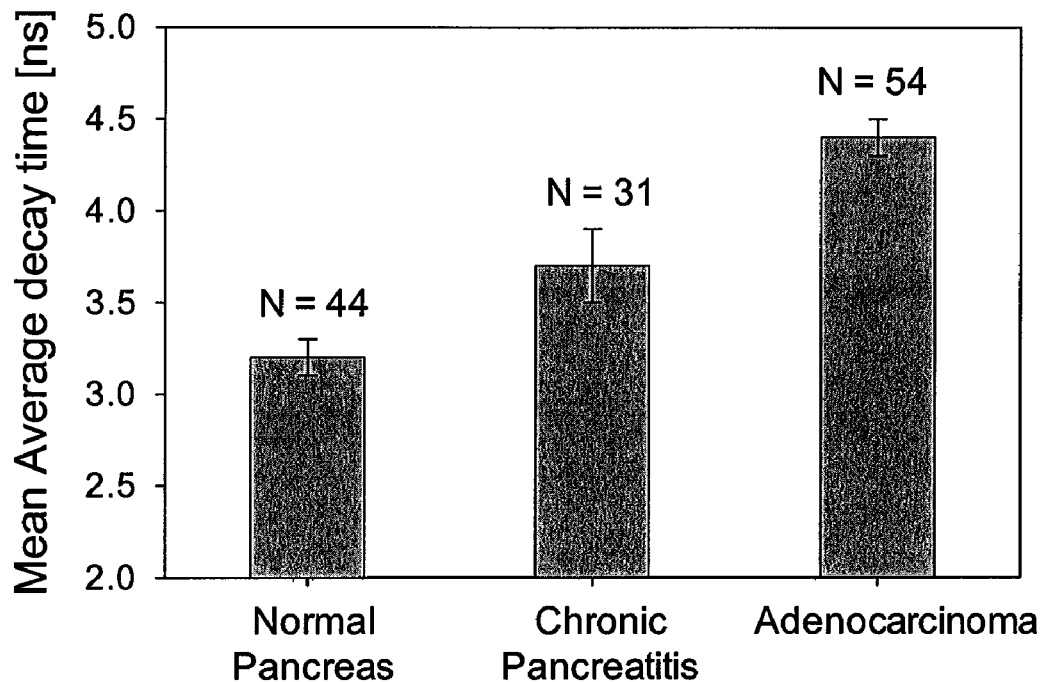
FIG. 15 is a bar graph depicting the mean average decay times for different pancreatic tissue types in connection with Illustration VII.

FIG. 14b shows the percentage contribution of extracellular collagen to the intrinsic fluorescence of normal pancreatic tissue, chronic pancreatitis, and pancreatic adenocarcinoma. The mean±standard error values of the percent contributions of extracellular collagen fluorescence to the spectra of normal pancreatic tissue, pancreatitis, and adenocarcinoma were 15.5±3.5, 28.7±3.8, and 60.9±4.8, respectively. The results shown in FIG. 15 suggest that the percentage contribution of extracellular collagen to the intrinsic fluorescence is potentially useful (*, $p<2\times10^{-5}$ from Wilcoxon rank-sum tests) for distinguishing adenocarcinoma from normal pancreatic tissue, as well as distinguishing adenocarcinoma from chronic pancreatitis. FIG. 15 also shows that the percentage contribution of extracellular collagen to the intrinsic fluorescence is potentially useful (**, $p<5\times10^{-2}$ from Wilcoxon rank-sum test) for distinguishing chronic pancreatitis from normal pancreatic tissue. These results agree with qualitative histopathological observation and hydroxyproline content analysis, both of which have revealed increases in the amount of collagen found in chronic pancreatitis and pancreatic adenocarcinoma, relative to normal pancreatic tissue.

5. Discussion

The results shown in FIGS. 13 and 14*a,b* suggest that reflectance and fluorescence spectrocopies have the potential to distinguish among pancreatic tissue types, including normal pancreatic tissues, chronic pancreatitis, and pancreatic adenocarcinoma, using biophysical tissue parameters extracted from the data via the PTI model of light propagation. The relevant biophysical parameters for distinguishing the different pancreatic tissue types were the nuclear dilation factor $L/L_o$ and the percentage contribution of extracellular collagen to the intrinsic fluorescence. The observed increase in the nuclear dilation factor $L/L_o$ for adenocarcinoma, relative to normal pancreatic tissue and chronic pancreatitis, is in agreement with the findings of histopathology that the mean cellular nuclear diameter is larger in pancreatic adenocarcinoma than in normal pancreatic tissue and chronic pancreatitis. The increased percentage contributions of extracellular collagen to the intrinsic fluorescence for adenocarcinoma and chronic pancreatitis (relative to normal pancreatic tissue) are in agreement with studies demonstrating that there is increased collagen content in both pancreatic adenocarcinoma and tumor-associated chronic pancreatitis, relative to normal pancreatic tissue.

Since different source fibers were used for reflectance and fluorescence measurements, the light paths of the detected reflectance and fluorescence photons likely interrogated slightly different regions of each tissue site. However, since the reflectance and fluorescence photons were both collected by the same detector fiber, and all three fibers were positioned adjacent to each other in a triangular geometry, we used Monte Carlo simulations to estimate that the majority of reflectance and fluorescence photons collected at a given tissue site visited roughly the same (~1 mm$^3$) region of tissue.

The PTI model reported here does not make use of the hemoglobin concentration and blood-oxygen saturation parameters extracted from the reflectance fits. Since the measurements used for training the PTI model in this study were all obtained ex vivo, much of the hemoglobin absorption information obtained from these measurements is likely most directly related to the amount of blood that drained from each tissue sample and the time that each sample was exposed to air prior to measurement. We note that the blood absorption features present in the measured reflectance spectra were likely similar for measurements made on patients who underwent either type of pancreatic surgery (Whipple procedure or distal pancreatectomy). This is a reasonable assumption because in the distal pancreatectomy procedure, the splenic artery was divided early, producing a level of ischemia that was likely similar to that associated with the Whipple surgery.

In an in vivo setting, we expect to see changes in the measured reflectance spectra that can be linked to differences in the vasculature and blood oxygenation (and hence, the hemoglobin absorption) of pancreatic adenocarcinoma, chronic pancreatitis, and normal pancreatic tissue. We also expect the PTI model to be capable of describing these changes in terms of the total hemoglobin concentration, blood-oxygen saturation, and mean blood vessel radius, as well as the possible addition of a variable to represent the packaging of hemoglobin into erythrocytes. In preparation for future in vivo studies, we are working to further refine the PTI model and examine in greater detail the effect of the hemoglobin absorption parameters on the modeled reflectance. We do not anticipate that the accuracy of the PTI model will be significantly affected by the transition to an in vivo setting, since the model can account for increased levels of absorption due to blood. Thus, the results reported in this study illustrate the potential of the PTI model to address the clinical need for accurate detection of pancreatic adenocarcinoma in the setting of chronic pancreatitis. An optical sensing technique involving the PTI model could potentially be employed in a clinical setting to guide EUS-FNA biopsy.

6. Conclusions

In this study, we demonstrate the first-ever use of a photon-tissue interaction (PTI) model to fit individual reflectance and fluorescence spectra from human pancreatic tissues, among other things. The best fits of the PTI model to the optical spectra extracted diagnostically-relevant biophysical parameters. The nuclear dilation factor was extracted from the PTI reflectance model, and the percent contribution of extracellular collagen to the intrinsic fluorescence was extracted from the PTI fluorescence model. Both of these parameters were statistically significant for distinguishing pancreatic adenocarcinoma from normal pancreatic tissue, as well as for distinguishing adenocarcinoma from chronic pancreatitis. Furthermore, the percent contribution of extracellular collagen to the intrinsic fluorescence was also statistically significant for distinguishing chronic pancreatitis from normal pancreatic tissue. These results indicate that optical spectroscopy involving a photon-tissue interaction model has the potential to quantitatively distinguish between different pancreatic tissue types and to provide an inroad toward addressing the clinical need for accurate detection of early-stage pancreatic cancer.

Illustration VII

1. Introduction

Data described herein were acquired with a RFLS constructed as described herein, such as the exemplary system 10. See also the following peer-reviewed publications: M. Chandra, J. Scheiman, D. Simeone, B. McKenna, J. Purdy, and M.-A. Mycek, "Spectral areas and ratios classifier algorithm for pancreatic tissue classification using optical spectroscopy," J. Biomed. Opt. 15, 010514 (2010); M. Chandra, J. Scheiman, D. Heidt, D. Simeone, B. McKenna, and M.-A. Mycek, "Probing Pancreatic Disease using Tissue Optical Spectroscopy," J. Biomed. Opt. 12, 060501 (2007); and M. Chandra, D. Heidt, D. Simeone, B. McKenna, J. Scheiman, and M.-A. Mycek, "Pancreatic tissue assessment using fluorescence and reflectance spectroscopy," Proc. SPIE 6628, 66281R (2007).

2. Methods

Overall, 231 measurements from 116 tissue sites (normal pancreas, chronic pancreatitis, adenocarcinoma) of 18 patients were acquired with RFLS. However, eight of these measurements were excluded, either because the ratio of the reflectance at 550 nm was less than 10% of that at 650 nm, or because the fluorescence signal-to-noise ratio was less than 25. The remaining wavelength-resolved reflectance and fluorescence data was subdivided into two main sets as described below.

A data set A for the first 9 patients consists of 50 sites (11 normal pancreas, 22 chronic pancreatitis, 17 adenocarcinoma) and 96 measurements (22 normal pancreas, 41 chronic pancreatitis, 33 adenocarcinoma).

A data set B for the remaining 9 patients consists of 66 sites (33 normal pancreas, 16 chronic pancreatitis, 17 adenocarcinoma) and 127 measurements (61 normal pancreas, 32 chronic pancreatitis, 34 adenocarcinoma).

2.1 Time-resolved Fluorescence Data

The time-resolved fluorescence data was divided into two different subsets. The first subset includes data acquired without the long-pass filter, in which all wavelengths from 360-700 nm were used, and consists of 8 patients, 29 sites (18 normal pancreas, 9 chronic pancreatitis, 2 adenocarcinoma) and 56 measurements (34 normal pancreas, 18 chronic pancreatitis, 4 adenocarcinoma). The second subset includes data acquired with the long-pass filter, in which only wavelengths from 500-760 nm were used, and consists of 10 patients, 66 sites (24 normal pancreas, 15 chronic pancreatitis, 27 adenocarcinoma) and 128 measurements (44 normal pancreas, 30 chronic pancreatitis, 54 adenocarcinoma).

A mean average decay time was extracted from each time-resolved fluorescence decay curve for the above subsets of the pancreatic tissue data, by fitting each decay curve to a tri-exponential decay function of the form $A_1 e^{-t/\tau_1} + A_2 e^{-t/\tau_2} + A_3 e^{-t/\tau_3}$, extracting the values of $A_1$, $A_2$, $A_3$, $\tau_1$, $\tau_2$, and $\tau_3$ from an optimal fit, and then calculating the mean average decay time $\tau_{avg}$ from the equation:

$$\tau_{avg} = [(A_1 \tau_1^2) + (A_2 \tau_2^2) + (A_3 \tau_3^2)] / [(A_1 \tau_1) + (A_2 \tau_2) + (A_3 \tau_3)]. \quad (16)$$

Figure 16:
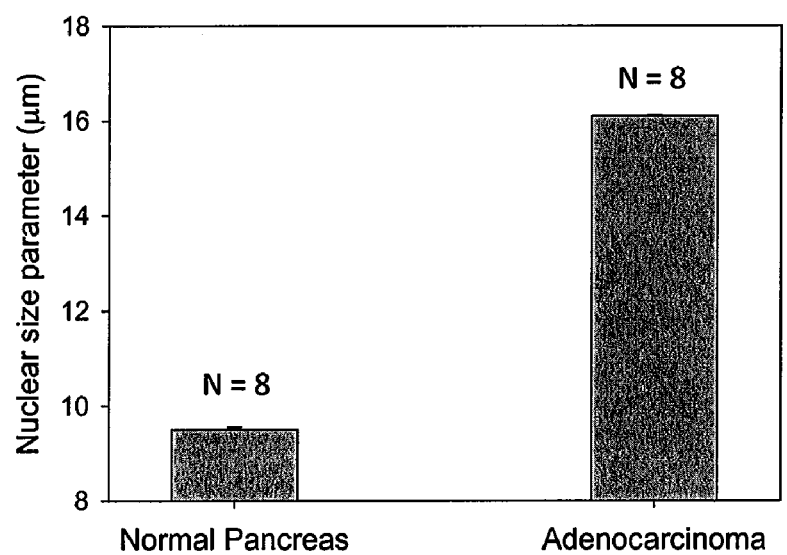
FIG. 16 is a bar graph illustrating the nuclear size parameter extracted from PTI2 reflectance model for normal pancreas (eight spectra) and adenocarcinoma (eight spectra) in connection with Illustration VII.
Figure 17:
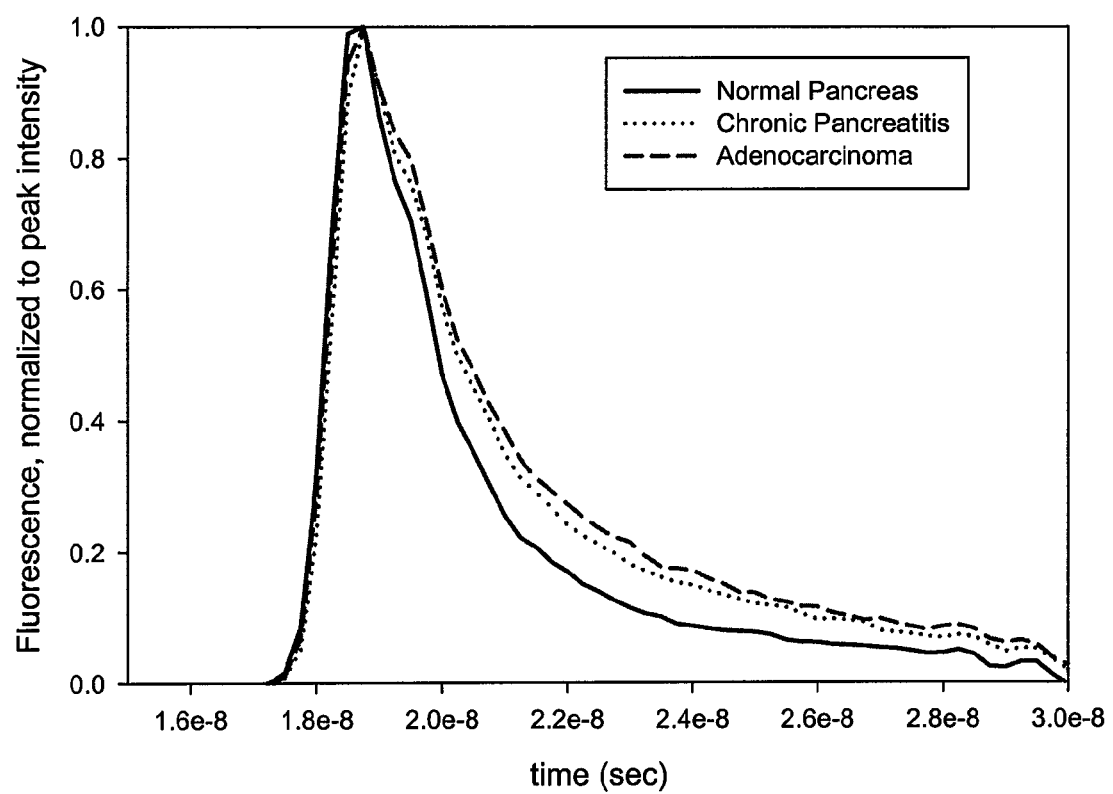
FIG. 17 illustrates representative time-resolved fluorescence decay curves from normal pancreatic tissue, chronic pancreatitis, and adenocarcinoma with respect to Illustration VII.

The value of the mean average decay time parameter was found to be significantly different ($p < 5 \times 10^{-2}$) for distinguishing between normal pancreas, chronic pancreatitis, and adenocarcinoma, as shown by the following Table 36 and bar graphs shown in FIGS. 15 and 16. FIG. 17 illustrates representative time-resolved fluorescence decay curves from normal pancreatic tissue, chronic pancreatitis, and adenocarcinoma.

TABLE 36 p-values for using mean average decay time to distinguish between pancreatic tissue types

| Classification | p-value from Wilcoxon rank-sum test |
|---|---|
| Malignant pancreatic tissue (adenocarcinoma) vs benign pancreatic tissue (normal pancreas and chronic pancreatitis) | $p = 1 \times 10^{-9}$ |
| Adenocarcinoma vs normal pancreas | $p = 4 \times 10^{-10}$ |
| Adenocarcinoma vs chronic pancreatitis | $p = 3 \times 10^{-4}$ |
| Chronic pancreatitis vs normal pancreas | $p = 4 \times 10^{-3}$ |

*All p-values reported here are statistically significant for classification

Illustration VIII

1. Introduction

Data described herein were acquired with a RFLS constructed as described herein, such as the exemplary system 10.

2. Methods for Tissue Classification

Principal Component Analysis (PCA) and Photon-Tissue Interaction algorithms were employed to extract classification parameters from the measured pancreatic tissue reflectance and fluorescence spectra.

PCA was undertaken on the fluorescence and reflectance spectral data separately. Two different sets of inputs were employed for classification. In the PCA 99% method, the first seven fluorescence and first five reflectance Principal Component (PC) scores were employed as classification variables that were input to a Generalized Estimating Equations (GEE) algorithm. These PCs explained 99% of the variance in the data. In the PCA 95% method, the first three fluorescence and first three reflectance PC scores were employed as classification variables that were input to the GEE algorithm. These PCs explained 95% of the variance in the data.

A Photon-Tissue Interaction model referred to as the "PTI1" model is described herein and in the following references: R. H. Wilson, M. Chandra, J. Scheiman, D. Simeone, B. McKenna, J. Purdy, and M. A. Mycek, "Optical spectroscopy detects histological hallmarks of pancreatic cancer," Opt. Express 17, 17502-17516 (2009) and R. H. Wilson, M. Chandra, L.-C. Chen, W. Lloyd, J. Scheiman, D. Simeone, J. Purdy, B. McKenna, and M.-A. Mycek, "Photon-tissue interaction model enables quantitative optical analysis of human pancreatic tissues" (submitted to Opt. Express).

The PTI1 model fits mathematical models of reflectance and fluorescence to individual measured wavelength-resolved spectra, and values of the nuclear diameter (L) and percentage contributions of collagen, NADH, and FAD to the fluorescence (% COLL, % NADH, % FAD) are extracted from the best fits. Another model, the "PTI1b" model, behaves in the same way as PTI1, except that an additional parameter is extracted from the best fit of the reflectance model to each measured wavelength-resolved reflectance spectrum. This additional parameter is the nuclear refractive index ($n_s$), which is then used along with L, % COLL, % NADH, and % FAD in the classification algorithms.

In order to classify a given spectrum as "normal," "chronic pancreatitis," or "adenocarcinoma," a GEE model was employed. The GEE model was chosen because it can correct the acquired data set for intra-patient correlations (classification algorithm errors caused by the fact that there were multiple spectra acquired from each patient).

Prior to analysis with the classification algorithms, the following tissue sites were flagged as "outliers" and removed from the data set: (1) sites where the reflectance at 550 nm was less than 20% of that at 650 nm, (2) sites where the fluorescence signal-to-noise ratio was less than 30, and (3) sites where the two measurements were very different from each other.

3. Results

For the data analysis reported here, the initial data set (Data Set (A+B)) consisted of 116 tissue sites from 18 patients, and the data set used for analysis (following outlier removal) contained 105 tissue sites from 18 patients (9% of the sites were removed). Preliminary results of the GEE algorithm with parameters extracted from the PCA and PTI models are shown in Table 37 below:

TABLE 37

GEE tissue classification results for PCA and PTI:

| Method | Sensitivity | Specificity | PPV | NPV |
|---|---|---|---|---|
| For distinguishing malignant pancreatic tissue (adenocarcinoma) from benign pancreatic tissue (normal and chronic pancreatitis): | | | | |
| PCA 99% | 87% | 88% | 74% | 94% |
| PCA 95% | 90% | 80% | 64% | 95% |
| PTI 1 | 83% | 87% | 71% | 93% |
| PTI 1b | 87% | 85% | 70% | 94% |

TABLE 37-continued

GEE tissue classification results for PCA and PTI:

| Method | Sensitivity | Specificity | PPV | NPV |
|---|---|---|---|---|
| For distinguishing pancreatic adenocarcinoma from chronic pancreatitis: | | | | |
| PCA 99% | 53% | 69% | 59% | 63% |
| PCA 95% | 80% | 60% | 63% | 78% |
| PTI 1 | 80% | 77% | 75% | 82% |
| PTI 1b | 90% | 74% | 75% | 90% |

*PCA 99% = Principal Component Analysis model using PCs that explain 99% of the variance in the data
*PCA 95% = Principal Component Analysis model using PCs that explain 95% of the variance in the data
*PTI 1 = Photon-Tissue Interaction model reported in manuscript submitted to Optics Express (Mycek_PTI_6-2010-OE.vf.doc)
*PTI 1b = same as PTI 1, except that an additional parameter (the nuclear refractive index) was extracted from the best fit of the model to each spectrum The previously-published PTI1 reflectance model (see above) uses an average measured "canonical normal" reflectance spectrum as a starting point. Another PTI reflectance model (referred to as "PTI2") has been developed and is disclosed herein. The PTI2 reflectance model employs a "direct fitting" approach in which each measured reflectance spectrum is fit directly with an empirical equation for the reflectance as a function of the tissue and probe properties. Therefore, the PTI2 reflectance model does not use a "canonical normal" spectrum as a starting point, so it does not require the use of parameters related to the "canonical normal" spectrum (such as for example, the hemoglobin concentration and blood oxygen saturation of the "canonical normal" spectrum). The PTI2 model also accounts for the packaging of hemoglobin into red blood cells; the PTI1 and PTI1b models did not account for this effect.

A version of the PTI2 model was run for eight normal pancreas reflectance spectra and eight adenocarcinoma reflectance spectra. The free parameters were the nuclear diameter, oxy-hemoglobin concentration, deoxy-hemoglobin concentration, beta-carotene concentration, and pigment packaging factor; the PTI1 and PTI1b models did not include the beta-carotene concentration or pigment packaging factor.

Figure 18:
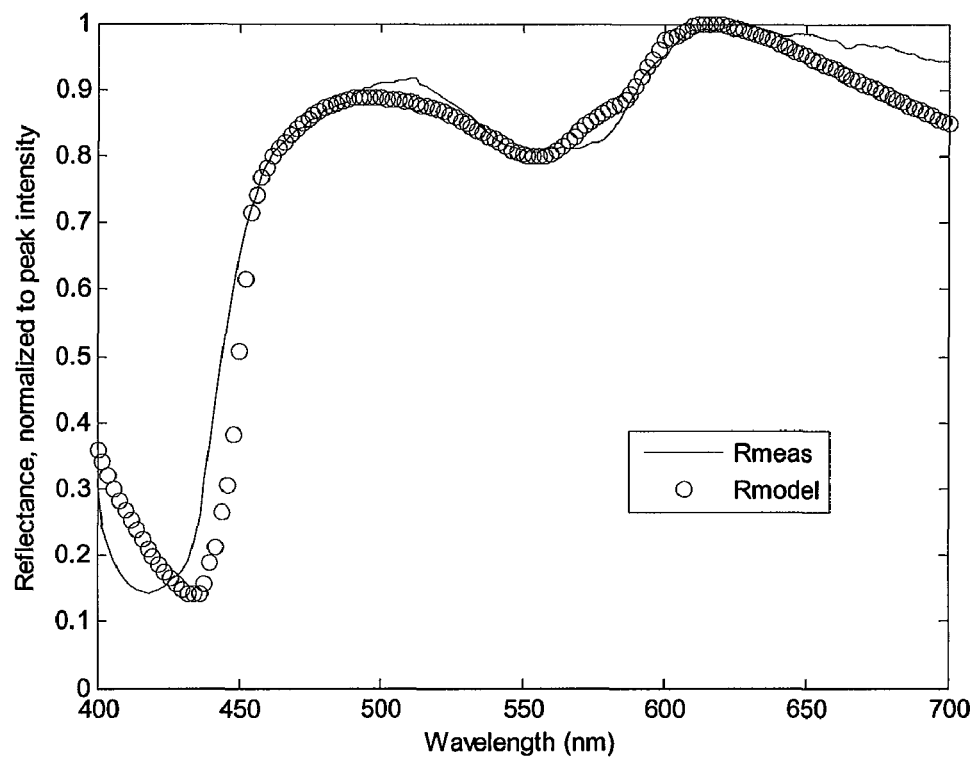
FIGS. 18 and 19 provide representative graphical plots fitting the PTI2 model to the adenocarcinoma spectrum (FIG. 18) and the normal pancreas reflectance spectrum (FIG. 19) in connection with some embodiments of the invention and Illustration VIII.
Figure 19:
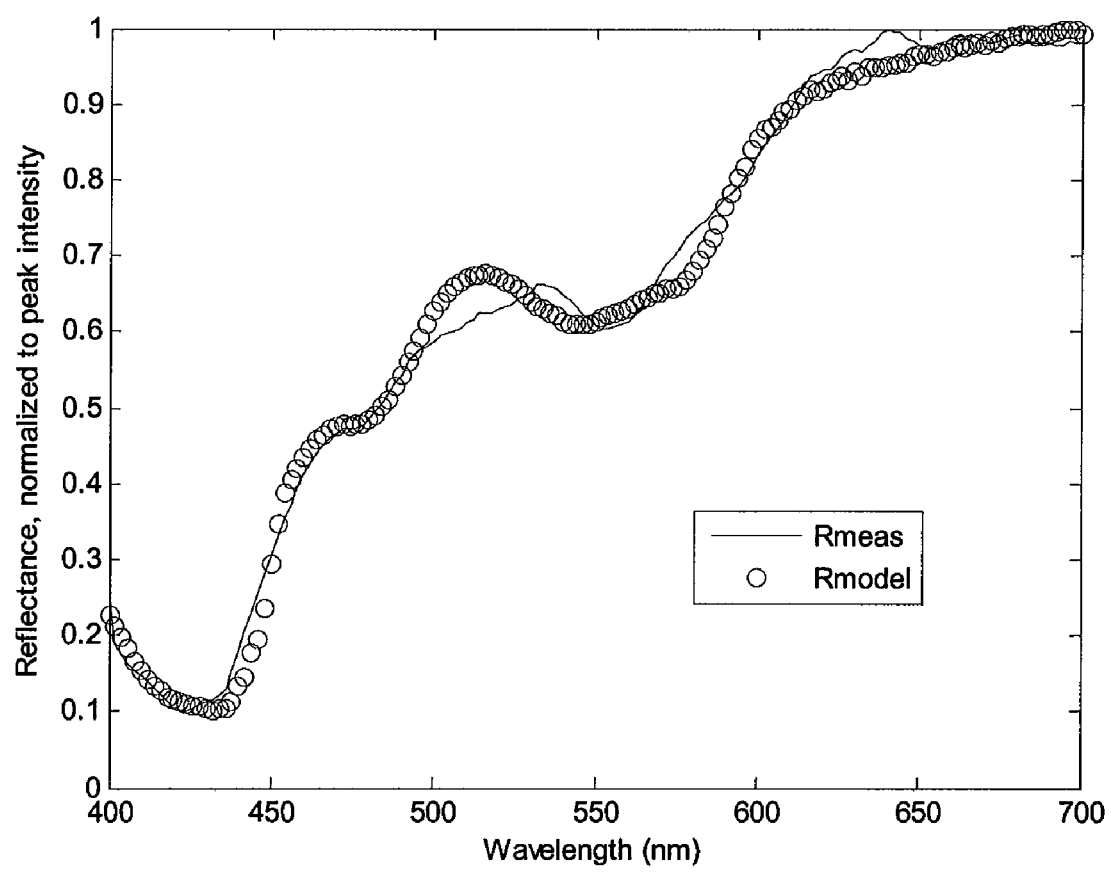

Representative fits of the PTI2 model, as shown in FIGS. 18 and 19, to the data show good agreement, and the extracted (mean±standard error) nuclear diameter was 16.1 µm±0.01 µm for pancreatic adenocarcinoma, as compared to 9.50 µm±0.05 µm for normal pancreas. These results suggest that the PTI2 model has the potential to provide accurate fits, including in the regions where hemoglobin absorption is high (near about 420 nm and near about 550 nm), which may be of importance for in vivo work, where the presence of blood will likely be more significant. These results also show that the PTI2 model can extract diagnostically important information about the changes in nuclear size associated with adenocarcinoma, relative to normal pancreatic tissue. The GEE tissue classification outcomes for Data Set (A+B) are summarized in Table 37 below.

TABLE 37

GEE tissue classification results including PTI2

| Method | Sensitivity | Specificity | PPV | NPV |
|---|---|---|---|---|
| For distinguishing malignant pancreatic tissue (adenocarcinoma) from benign pancreatic tissue (normal and chronic pancreatitis): | | | | |
| PCA 99% | 87% | 88% | 74% | 94% |
| PCA 95% | 90% | 80% | 64% | 95% |
| PTI 1 | 83% | 87% | 71% | 93% |
| PTI 1b | 87% | 85% | 70% | 94% |

TABLE 37-continued

GEE tissue classification results including PTI2

| Method | Sensitivity | Specificity | PPV | NPV |
|---|---|---|---|---|
| PTI 2 | 87% | 88% | 74% | 94% |
| PTI 2b | 87% | 87% | 72% | 94% |
| For distinguishing pancreatic adenocarcinoma from chronic pancreatitis: | | | | |
| PCA 99% | 53% | 69% | 59% | 63% |
| PCA 95% | 80% | 60% | 63% | 78% |
| PTI 1 | 80% | 77% | 75% | 82% |
| PTI 1b | 90% | 74% | 75% | 90% |
| PTI 2 | 87% | 74% | 74% | 87% |
| PTI 2b | 83% | 74% | 74% | 84% |

*PCA 99% = Principal Component Analysis model using PCs that explain 99% of the variance in the data
*PCA 95% = Principal Component Analysis model using PCs that explain 95% of the variance in the data
*PTI 1 = Photon-Tissue Interaction model reported in manuscript submitted to Optics Express (incorporated herein)
*PTI 1b = same as PTI 1, except that an additional parameter (the nuclear refractive index) was extracted from the best fit of the model to each spectrum
*PTI 2 = "Direct fit" Photon-Tissue Interaction model described herein and in references incorporated herein.
*PTI 2b = same as PTI 2, except that an additional parameter (the nuclear refractive index) was extracted from the best fit of the model to each spectrum Obviously, many modifications and variations of the embodiments of the invention are possible in light of the above teachings. The invention may be practiced otherwise than as specifically described within the scope of the appended claims.

What is claimed is:

1. A method of employing multimodal spectroscopy to classify tissue comprising the steps of:
   (a) illuminating a biological tissue sample to produce a measurable spectroscopic event;
   (b) collecting spectroscopic response data from the spectroscopic event, wherein the response data includes measurements derived from fluorescence and reflectance signals associated with the tissue sample including reflectance spectra, fluorescence spectra and time-resolved fluorescence decay measurements;
   (c) comparing the response data with an empirical equation for the reflectance as a function of the tissue and probe properties to determine one or more attributes of the tissue sample, wherein each attribute is at least partially indicative of a tissue classification; and
   (d) classifying the tissue sample according to the one or more attributes determined.

2. A method according to claim 1, wherein the step of illuminating the biological tissue sample is configured to produce a plurality of measurable spectroscopic events.

3. A method according to claim 2, wherein the illuminating step includes an event including illumination wavelengths of about 400 nm to about 750 nm to facilitate collecting reflectance signal measurements and an event including illumination wavelengths of about 355 to facilitate collecting fluorescence signal measurements.

4. A method according to claim 1, further comprising the step of developing the empirical equation by applying a photon-tissue interaction model to the fluorescence, reflectance and time-resolved spectroscopic measurements.

5. A method according to claim 1, wherein the one or more attributes of the tissue sample comprise one or more histological features.

6. A method according to claim 1, wherein the step of classifying the tissue sample further includes classifying the tissue as normal or abnormal.

7. A method according to claim 1, wherein the equation relates the deviation between the collected spectroscopic response data at a plurality of wavelengths for the tissue sample and spectroscopic response data at the plurality of wavelengths for normal tissue with one or more histological features associated with the tissue sample.

8. A method according to claim 1, wherein attributes of the tissue sample include the nuclear size of cells associated with the tissue sample, the collagen content associated with the tissue sample, the NADH content associated with the tissue sample, and the FAD content associated with the tissue sample.

9. A method according to claim 1, wherein the tissue sample is pancreatic tissue and the tissue sample classifications include normal, adenocarcinoma and pancreatitis.

10. A system for classifying biological tissue using multimodal optical spectroscopy, comprising:
    (a) a light source for generating light to illuminate a biological tissue sample;
    (b) a probe configured for directing the light generated by the light source onto the tissue sample to illuminate the tissue sample and generate a measurable spectroscopic event;
    (c) one or more detectors configured for collecting spectroscopic response data, wherein the spectroscopic response data includes measurements derived from fluorescence and reflectance signals associated with the tissue sample including reflectance spectra, fluorescence spectra and time-resolved fluorescence decay measurements; and
    (d) a data processor configured for:
        (i) analyzing the collected spectroscopic response data;
        (ii) comparing the response data with an empirical equation for the reflectance as a function of the tissue and probe properties to determine one or more attributes of the tissue sample, wherein each attribute is at least partially indicative of a tissue classification; and
        (iii) classifying the tissue sample according to the one or more attributes determined.

11. A system as recited in claim 10, wherein the probe further comprises a plurality of optical fibers for directing light onto the tissue sample, receiving fluorescence and reflectance signals from the tissue sample and directing the received fluorescence and reflectance signals to the one or more detectors.

12. A system as recited in claim 10, wherein the probe further comprises a first optical fiber configured for delivering reflectance illumination to the tissue sample, a second optical fiber configured for delivering fluorescence illumination to the tissue sample and a third optical fiber configured for detecting emitted reflectance and fluorescence from the tissue sample.

13. A system as recited in claim 12, wherein the first, second and third optical fibers are disposed in a generally triangular cross-sectional arrangement.

14. A system as recited in claim 10, wherein the one or more attributes determined include the nuclear diameter, the oxy-hemoglobin concentration, the deoxy-hemoglobin concentration and the beta-carotene concentration of the tissue sample.

15. A system as recited in claim 10, wherein the light source further comprises a light source configured for generating light at wavelengths of about 400 nm to about 750 nm to facilitate collecting reflectance signal measurements and a light source configured for generating light at wavelengths of about 355 to facilitate collecting fluorescence signal measurements.

16. A method employing multimodal optical spectroscopy to classify pancreatic tissue, comprising:
    (a) illuminating a pancreatic tissue sample to produce a measurable spectroscopic event;
    (b) collecting spectroscopic response data from the spectroscopic event, wherein the response data includes measurements derived from fluorescence and reflectance signals associated with the tissue sample including reflectance spectra, fluorescence spectra and time-resolved fluorescence decay measurements;
    (c) comparing the response data with an empirical equation for the reflectance as a function of the tissue and probe properties, wherein each measured reflectance spectrum is fit directly with an empirical equation for the reflectance to determine one or more histological features associated with the pancreatic tissue sample, and wherein the histological features are indicative of a tissue classification of either normal pancreatic tissue, adenocarcinoma or pancreatitis; and
    (d) classifying the tissue sample as either normal, adenocarcinoma or pancreatitis based on the one or more histological features based on the one or more attributes determined.

17. A method according to claim 16, further comprising comparing the response data at wavelengths ranging between about 360 nm to about 750 nm with the preset criteria.

18. A method according to claim 16, wherein the one or more histological features determined include the nuclear diameter, the oxy-hemoglobin concentration, the deoxy-hemoglobin concentration and the beta-carotene concentration of the tissue sample.

* * * * *